(12) United States Patent
Quintero Ortiz et al.

(10) Patent No.: US 11,883,424 B2
(45) Date of Patent: *Jan. 30, 2024

(54) METHODS OF MAKING NOVEL PHARMACEUTICAL COMPOSITIONS

(71) Applicant: HIGHLIGHT THERAPEUTICS, S.L., Valencia (ES)

(72) Inventors: Marisol Quintero Ortiz, Valencia (ES); Mercedes Pozuelo Rubio, Valencia (ES); Lourdes Planelles Carazo, Valencia (ES)

(73) Assignee: Highlight Therapeutics, S.L., Valencia (ES)

(*) Notice: Subject to any disclaimer, the term of this patent is extended or adjusted under 35 U.S.C. 154(b) by 618 days.

This patent is subject to a terminal disclaimer.

(21) Appl. No.: 17/084,995

(22) Filed: Oct. 30, 2020

(65) Prior Publication Data
US 2021/0069238 A1  Mar. 11, 2021

Related U.S. Application Data

(63) Continuation of application No. 16/614,439, filed as application No. PCT/EP2017/079688 on Nov. 17, 2017, now Pat. No. 10,849,921.

(30) Foreign Application Priority Data

May 17, 2017 (EP) ..................... 17171617
May 26, 2017 (EP) ..................... 17382301
Nov. 7, 2017 (EP) ..................... 17200469

(51) Int. Cl.
*A61K 31/713* (2006.01)
*A61K 9/00* (2006.01)
(Continued)

(52) U.S. Cl.
CPC .......... *A61K 31/713* (2013.01); *A61K 9/0019* (2013.01); *A61K 9/08* (2013.01);
(Continued)

(58) Field of Classification Search
CPC ...... A61K 31/713; A61K 9/0019; A61K 9/19; A61K 39/00; A61K 47/26; A61K 47/6929
(Continued)

(56) References Cited

U.S. PATENT DOCUMENTS 10,653,768 B2    5/2020  Mutzke et al.
10,869,881 B2 * 12/2020  Pozuelo Rubio ...... A61K 47/59
(Continued)

FOREIGN PATENT DOCUMENTS

CN    102988303    3/2013
CN    103599071    2/2014
(Continued)

OTHER PUBLICATIONS

U.S. Appl. No. 15/753,328 (Year: 2016).*
(Continued)

*Primary Examiner* — Jane J Zara
(74) *Attorney, Agent, or Firm* — Stacey J. Farmer; Grund IP Group

(57) ABSTRACT

The present invention relates to compositions comprising complexes that are formed by polyinosinic-polycytidylic acid with a polyalkyleneimine, such as polyethyleneimine, that present uniform structural and functional features, as well as to methods for preparing the compositions that comply with regulatory requirements. The present invention additionally relates to use of said compositions as medicaments (in particular for treating cancer), alone or in combination with other therapeutic agents and/or in specific medical methods. Moreover, the administration of these compositions is associated to changes in the expression of (Continued)

specific genes, in cell responses, and/or in composition of immune cell populations that can be used as specific biomarkers and/or as additional target for medical treatment.

19 Claims, 17 Drawing Sheets

(51) Int. Cl.
    *A61K 9/08*         (2006.01)
    *A61K 9/19*         (2006.01)
    *C07K 16/28*       (2006.01)
    *A61K 47/69*       (2017.01)
    *A61K 47/26*       (2006.01)
    *A61K 47/50*       (2017.01)
    *A61K 31/15*       (2006.01)
    *A61K 31/74*       (2006.01)

(52) U.S. Cl.
    CPC ............... *A61K 9/19* (2013.01); *A61K 31/15* (2013.01); *A61K 31/74* (2013.01); *A61K 47/26* (2013.01); *A61K 47/50* (2017.08); *A61K 47/6935* (2017.08); *C07K 16/2818* (2013.01); *C07K 16/2827* (2013.01)

(58) Field of Classification Search
    USPC ...... 424/9.1; 435/6.1, 91.1, 91.31, 455, 458; 536/23.1, 24.5
    See application file for complete search history.

(56) References Cited

U.S. PATENT DOCUMENTS

2009/0117306 A1     5/2009     Miyata et al.
2011/0003883 A1     1/2011     Lee et al.

FOREIGN PATENT DOCUMENTS

| WO | WO 2004/045491 | 6/2004 |
| --- | --- | --- |
| WO | WO 2005/102278 | 11/2005 |
| WO | WO 2008/057696 | 5/2008 |
| WO | WO 2011/003883 | 11/2011 |
| WO | WO 2013/040552 | 3/2013 |
| WO | WO 2013/063019 | 5/2013 |
| WO | WO 2013/087083 | 6/2013 |
| WO | WO 2013/164380 | 11/2013 |
| WO | WO 2014/057432 | 4/2014 |
| WO | WO 2014/165296 | 10/2014 |
| WO | WO 2015/067632 | 5/2015 |
| WO | WO 2015/173824 | 11/2015 |
| WO | WO 2016/178233 | 11/2016 |
| WO | WO 2017/085228 | 5/2017 |

OTHER PUBLICATIONS

U.S. Appl. No. 17/095,059 (Year: 2020).*
Rapoport, Aaron P. et al, Clinical Cancer Research, American Association for Cancer Research, 20(5), pp. 1355-1365, Mar. 1, 2014.
Salazar, Andres M. et al, Clinical Cancer Research, American Association for Cancer Research, 2(8), pp. 720-724, Aug. 2014.
Hafner A et al., "Particulate formulations for the delivery of poly (I: C) as vaccine adjuvant". Advanced Drug Delivery Rev. 2013; 65 (10): 1386-1399.
Schaffert D et al., "Poly (I: C)-mediated tumor growth suppression in EGF-receptor overexpressing tumors using EGF-polyethylene glycol-linear polyethylenimine as carrier". Pharm. Res. 2011; 28 (4): 731-741.
Kabilova T et al., "Immunotherapy of hepatocellular carcinoma with small double-stranded RNA". BMC Cancer. 2014; 14: 338.
Kübler K et al ., "Immunogenic cell death of human ovarian cancer cells induced by cytosolic poly(I:C) leads to myeloid cell maturation and activates NK cells". Eur. J. Immunol. 2011; 41 (10): 3028-39.
Palchetti S et al., "Structural characterization of cationic liposome/poly(I:C) complexes showing high ability in eliminating prostate cancer cells". RSC Adv. 2013; 3 (46): 24597-24604.
Saheki A et al., "Influence of preparation method on polynucleotide conformation and pharmacological activity of lipoplex". Int. J. Pharm. 2011; 406 (1-2): 117-21.
Chen L et al., "Codelivery of zoledronic acid and doublestranded RNA from core-shell nanoparticles". INt. J. Nanomed. 2013; 8: 137-145.
McBain S et al., "Polyethyleneimine functionalized iron oxide nanoparticles as agents for DNA delivery and transfection". J. Mater. Chem. 2007; 17 (24): 2561-2565.
Cobaleda-Siles M et al., "An Iron Oxide Nanocarrier for dsRNA to Target Lymph Nodes and Strongly Activate Cells of the Immune System". Small. 2014; 10 (24): 5054-67.
Kurosaki T et al., "Ternary complexes of pDNA, polyethylenimine, and v-polyglutamic acid for gene delivery systems". Biomaterials. 2009; 30 (14): 2846-2853.
Turin-Moleavin I et al., "Dynamic constitutional frameworks (DCFs) as nanovectors for cellular delivery of DNA.". Org. & Biomol. Chem. 2015; 13: 9005-9011.
Bilensoy E, "Cationic nanoparticles for cancer therapy". Expert Opin. Drug Deliv. 2010; 7 (7):795-809.
Germershaus O and Nultsch K, "Localized, non-viral delivery of nucleic acids: Opportunities, challenges and current strategies". Asi. J. Pharm. Sci. 2015; 10 (3): 159-175.
Islam M et al., "Major degradable polycations as carriers for DNA and siRNA". Journal of Controlled Release 2014; 193: 75-89.
Shabani M et al., "Optimization of Gene Transfection in Murine Myeloma Cell Lines using Different Transfection Reagents". Avicenna J. Med. Biotech. 2010; 2 (3): 123-130.
Pozuelo-Rubio M et al., "BO-110, a dsRNA-Based Anticancer Agent". Nano-Oncologicals in Adv. De. Sci. Tech. 2014, Springer, pp. 453-470.
Tormo D et al., "Targeted Activation of Innate Immunity for Therapeutic Induction of Autophagy and Apoptosis in Melanoma Cells". Cancer Cell. 2009; 16 (2): 103-114.
Bhoopathi P et al., "Pancreatic Cancer-Specific Cell Death Induced In Vivo by Cytoplasmic-Delivered Polyinosine-Polycytidylic Acid". Cancer Res. 2014; 74 (21): 6224-35.
Garcia-Pascual C and Gomez R., "Administration of compound BO-110 reduces neoangiogenesis and cellular proliferation and increases apoptosis in a heterologous mice model of enfometriosis". J. Endometr. 2013; 5 (suppl.1): S13 (SP-04).
Le U et al., "Tumor chemo-immunotherapy using gemcitabine and a synthetic dsRNA". Canc. Biol. Ther. 2008; 7 (3): 440-447.
Le U et al., "Localized irradiation of tumors prior to synthetic dsRNA therapy enhanced the resultant anti-tumor activity". Radiother. Oncol. 2009; 90 (2): 273-279.
Taura M et al., "TLR3 induction by anticancer drugs potentiates poly I:C-induced tumor cell apoptosis". Cancer Sci. 2013; 101 (70: 1610-7.
Matijevic T et al., "Antitumor Activity from the Combined Application of Poly(I:C) and Chemotherapeutics in Human Metastatic Pharyngeal Cell Lines". Chemotherapy 2011; 57: 460-7.
Levitzki A, "Targeting the immune system to fight cancer using chemical receptor homing vectors carrying polyinosine/cytosine (PolyIC)". Front. Oncol. 2012; 2: 4.
Yoshino H and Kashiwakura I, "Beneficial Effects Of Ionizing Radiation To Enhance Anti-Cancer Effects Of RIG-Like Receptor Stimulus". Blood 2013; 122:4721.
Zhou Y et al., "TLR3 activation efficiency by high or low molecular mass poly I:C". Innate Immun. 2013; 19 (2): 184-192.
Ammi R et al., "Poly(I:C) as cancer vaccine adjuvant: Knocking on the door of medical breakthroughs". Pharmacol. Ther. 2015; 146:1 20-31.
Nagato T and Celis E, "A novel combinatorial cancer immunotherapy". Oncoimmunology 2014; 3 (5): e28440.

(56) References Cited

OTHER PUBLICATIONS

Zhang Y et al., "Phosphorothioate modification of the TLR9 ligand CpG ODN inhibits poly (I: C)-induced apoptosis of hepatocellular carcinoma by entry blockade". Cancer Lett. 2014; 355: 76-84.
Ohashi T et al., "Dichloroacetate improves immune dysfunction caused by tumor-secreted lactic acid and increases antitumor immunoreactivity". Int. J. Cancer. 2013; 133 (5): 1107-18.
Chiba Y et al., "IL-27 Enhances the Expression of TRAIL and TLR3 in Human Melanomas and Inhibits Their Tumor Growth in Cooperation with a TLR3 Agonist Poly(I:C) Partly in a TRAIL-Dependent Manner". PLOSOne 2013; 8: e76159.
Ho V et al., "TLR3 agonist and Sorafenib combinatorial therapy promotes immune activation and controls hepatocellular carcinoma progression". Oncotarget 2015; 6 (29): 27252-27266.
Gupta S et al., "Poly (I:C) enhances the anti-tumor activity of canine parvovirus NS1 protein by inducing a potent anti-tumor immune response". Tumor Biol. 2016; 37 (9): 12089-12102.
Szabo A et al., "Temporally designed treatment of melanoma cells by ATRA and polyI: C results in enhanced chemokine and IFNβ secretion controlled differently by TLR3 and MDA5". Melanoma Res. 2012; 22 (5): 351-361.
Yu L et al., "Polyinosinic-polycytidylic acid inhibits the differentiation of mouse preadipocytes through pattern recognition receptor-mediated secretion of tumor necrosis factor-α". Immunol. Cell Biol. 2016; 94 (9): 875-885.
Cho K et al., "Poly I:C primes the suppressive function of human palatine tonsil-derived MSCs against Th17 differentiation by increasing PD-L1 expression". Immunobiology 2016; 222 (2): 394-398.
Vega-Letter A et al., "Differential TLR activation of murine mesenchymal stem cells generates distinct immunomodulatory effects in EAE". Stem Cell Res. & Ther. 2016; 7: 150.
Perrot I et al., "TLR3 and Rig-Like Receptor on Myeloid Dendritic Cells and Rig-Like Receptor on Human NK Cells Are Both Mandatory for Production of IFN-γ in Response to Double-Stranded RNA". J. Immunol. 2010; 185 (4): 2080-2088.
Bald T et al., "Immune Cell—Poor Melanomas Benefit from PD-1 Blockade after Targeted Type I IFN Activation". Cancer Discov. 2014; 4: 674-87.
Amos SM et al., "Adoptive immunotherapy combined with intratumoral TLR agonist delivery eradicates established melanoma in mice". Cancer Immunol. Immunother. 2011; 60 (5): 671-83.
Sajadian A et al., "Comparing the effect of Toll-like receptor agonist adjuvants on the efficiency of a DNA vaccine". Arch. Virol. 2014; 159 (8): 1951-1960.
Fujimura T et al., "Inhibitory effect of the polyinosinic-polycytidylic acid/cationic liposome on the progression of murine B16F10 melanoma". Eur. J. Immunol. 2006; 36 (12): 3371-80.
Storz U, "Intellectual property protection". MAbs. 2011; 3 (3): 310-7.
Keir M et al., "PD-1 and Its Ligands in Tolerance and Immunity". Annu. rev. Immunol. 2008; 26: 677-704.
Galluzzi L et al., "Classification of current anticancer immunotherapies". Oncotarget 2014; 5 (24): 12472-508.
Vacchelli E et al., "Trial Watch Toll-like receptor agonists for cancer therapy". Oncoimmunology 2013; 2 (8): e25396, e23510, e25595.
Van Der Jeught K et al., "Targeting the tumor microenvironment to enhance antitumor immune responses". Oncotarget 2015; 6 (3): 1359-81.
Ewel C et al., "Polyinosinic-Polycytidylic Acid Complexed with Poly-I-lysine and Carboxymethylcellulose in Combination with Interleukin 2 in Patients with Cancer: Clinical and Immunological Effects". Cancer Res. 1992; 52 (11): 3005-10.
Sanchez-Paulete AR et al., "Cancer Immunotherapy with Immunomodulatory Anti-CD137 and Anti-PD-1 Monoclonal Antibodies Requires BATF3-Dependent Dendritic Cells". Cancer Discov. 2015; pii: CD-15-0510.
Duewell P et al., "Targeted activation of melanoma differentiation-associated protein 5 (MDA5) for immunotherapy of pancreatic carcinoma". OnocoImmunol. 2015; 4 (10): e1029698.

\* cited by examiner

A)

B)

A)

B)

C)

D)

A)

B)

C)

A)

B)

C)

D)

A)

B)

A)

B)

C)

D)

A)

B)

C)

A)

B)

METHODS OF MAKING NOVEL PHARMACEUTICAL COMPOSITIONS

CROSS-REFERENCE TO RELATED APPLICATIONS

This application is a continuation application from U.S. application Ser. No. 16/614,439, filed on Nov. 18, 2019, which claims the benefit of International Patent Application PCT/EP2017/079688, filed Nov. 17, 2017, published as International Patent Publication WO 2018/210,439 on Nov. 22, 2018, which claims the benefit of European Patent Application EP 17171617.8, filed on May 17, 2017, European Patent Application EP 17382301.4, filed on May 26, 2017, and European Patent Application EP 17200469.9, filed on Nov. 7, 2017, the contents of each are hereby incorporated by reference.

FIELD OF THE INVENTION

The present invention relates to the field of pharmaceutical formulations comprising particles formed by polyribonucleotides and polymers, their production, and their medical use.

BACKGROUND OF THE INVENTION

The use of synthetic analogs of double-stranded RNA (dsRNA) that mimic viral dsRNA has been explored in recent years for specifically activating the immune system against tumors with the effect of inhibiting cancer cell growth and inducing cancer cell apoptosis. In particular, double-stranded polyinosinic-polycytidylic acid (known as poly(I:C) or pIC) has been characterized as a type of dsRNA with various effects of therapeutic interest against several types of cancers (such as melanoma, hepatoma, colon, gastric, and oral carcinoma, cervical cancer, breast cancer, ovarian cancer, urinary tract tumors, lung and prostate cancer) and their metastasis, in manners that may be dependent or independent from immune system activation, natural killer- and/or dendritic cell-mediated activities, and/or changes of tumor gene expression and microenvironment (Hafner A et al., 2013).

Unfortunately, these initial preclinical reports are poorly or not confirmed in clinical studies with naked poly(I:C) molecules, which have demonstrated their low stability, poor homogeneity, unpredictable pharmacokinetics, and limited anti-tumoral effects due to a variety of mechanisms, such as poor cellular uptake or degradation by cytosolic RNases (Hafner A et al., 2013). Indeed, in order to achieve an effective therapeutic or prophylactic effect, poly(I:C) molecules may need to be re-dissolved immediately prior or shortly before use, may be available in formulations at low concentrations, and/or must be frequently administered (e.g. every 2 hours).

During the last few years, there has been significant progress in formulating poly(I:C) molecules with immunomodulatory and/or therapeutic properties. Various methods of preparing and formulating poly(I:C) molecules as powder and/or integrated within polymer-based microparticles with or without targeting moieties and additional chemical linkers have been disclosed (CN103599071; CN102988303; WO2004045491; WO2008057696; WO2013164380; WO2015067632, WO2014057432; WO2014165296; Schaffert D et al., 2011; WO2015173824, Kabilova T et al., 2014; Kübler K et al., 2011; Palchetti S et al., 2013; Saheki A et al., 2011). Poly(I:C) molecules have been formulated with carrier polymers and in formats compatible for nasal administration (WO2013164380), stabilized with polylysine and carboxymethylcellulose (WO2005102278), encapsulated within cationic lipid-coated calcium phosphate nanoparticles, liposomes, or other vesicular structures (Chen L et al., 2013; US2009117306; US2011003883), or together with single stranded RNA and with cationic peptides like protamine (WO2013087083). Alternatively, poly(I:C) molecules have also been immobilized on solid particles and carriers such as iron oxide nanoparticles, with or without agents that would help targeting poly(I:C) molecules to specific cells or tissues (McBain S et al., 2007; Cobaleda-Siles M et al., 2014).

Some publications further disclose various ternary or quaternary complexes in the sub-micrometer range that are formed by polymers, poly(I:C) molecules, and/or double stranded DNA, with or without other components and gene-specific (Kurosaki T et al., 2009.; WO2013040552; WO2013063019; Tutin-Moeavin I et al., 2015). However, these approaches have the objective of providing agents that essentially administer DNA to the cells, while maintaining their viability, and not the selective killing of cancer cells.

The pitfalls that are limiting the clinical development of poly(I:C) molecules as a drug and its compliance with demanding regulatory requirements could be overcome by producing structurally complex anticancer complexes comprising poly(I:C) molecules together with drug delivery systems for cancer therapy that are often based on cationic polymers such as chitosan, polyethyleneimine (PEI), poly-L-lysine, polymethacrylates, imidazole- or cyclodextrin-containing polymers, poly(beta-amino ester)s, and related dendrimers. These polymeric systems (also called as Polyplex) are structurally and functionally distinct from lipid-based systems (also called as Lipoplex) and hybrid systems (also called as Lipopolyplex) that are similarly used for the local or systemic delivering of nucleic acids (Bilensoy E, 2010; Germershaus O and Nultsch K, 2015). Among Polyplex, PEI is a polyalkyleneimine being a cationic polymer of particular interest that can be modified at the level of linear/branched structure and size, chemical linkage, degradability, and derivatization (Islam M et al., 2014) and that, differently from lipoplex internalization by cells, is internalized both by clathrin-mediated and by caveolae mediated endocytosis (Shabani M et al., 2010).

This therapeutic approach involving the preparation and the administration of poly(I:C) molecules associated to PEI has been exemplified in the literature by the agent called BO-110 (Pozuelo-Rubio M et al., 2014; Tormo D et al., 2009; WO2011003883). This complex, also identified as [pIC]$^{PEI}$, not only engages a dual induction of autophagy and apoptosis in several cancer cell lines of melanoma and of other tumor types (such as gliomas or carcinomas) but also has no or limited effect on the viability of normal cells, such as melanocytes. BO-110 inhibits melanoma growth in animal models for demonstrating antitumoral and antimetastatic activity in vivo, even in severely immunocompromised mice. Moreover, a similar [pIC]$^{PEI}$-based agent stimulates the apoptosis in pancreatic ductal adenocarcinoma cells without affecting normal pancreatic epithelial cells and in vivo administration of [pIC]$^{PEI}$ inhibited tumor growth in tumor animal models (Bhoopathi P et al., 2014). A further effect of BO-110 administration is characterized in a model of endometriosis, wherein such agent reduces angiogenesis and cellular proliferation and increases apoptosis (Garcia-Pascual C and Gomez R, 2013). Thus, BO-110 and similar [pIC]$^{PEI}$ agents that comprise double-stranded polyribonucleotides represent a novel anticancer strategy with a broad spectrum of action, due to the combined activation of autophagy and apoptosis, autonomously and selectively in tumor cells, while maintaining the viability of normal cells of different lineages. However, BO-110, as for other double-stranded polyribonucleotide-based agents that have demonstrated efficacy in various pre-clinical models when associated with carriers, still needs to be provided in formulations that are stable in different storage conditions, uniformly manufactured and sized, and more readily adapted to medical uses (in particular those directed to cancer) with respect to most effective combinations, regimens, dosages, and clinical follow-up when using other drugs and therapies.

Indeed, prior art does not provide appropriate teaching for solving issues related to the most effective combination of structural and biophysical criteria that allow the production of poly(I:C)-containing compositions for treatment of cancer. Regulatory agencies also require being strictly compliant to the specifications on reproducibility, storage, and uniformity of the size and concentration of poly(I:C)-containing particles that are included within compositions for use in humans. The general features of formulations of double-stranded polyribonucleotide-based (such as poly(I:C) molecules) and related agents, compositions (collectively identified as BO-11X products), and related processes providing double-stranded polyribonucleotide molecules, at higher, and well-controlled, concentrations were described in the PCT application PCT/EP2016/078078. However, the pre-clinical and clinical characterization of BO-11X products are still needed to allow its effective medical use as a drug (in particular against cancer) in connection to specific indications, ongoing treatments, and/or regimens, while improving means for clinical evaluation and use together with patient compliance, and reducing the frequency of dosing double-stranded polyribonucleotide molecules with well-defined safety margin and therapeutic effects.

SUMMARY OF THE INVENTION

The present invention relates to a composition comprising particles wherein:
  (i) each of said particles comprises a complex of at least one double-stranded polyribonucleotide, or a salt or solvate thereof, and at least one polyalkyleneimine, or a salt and/or solvate thereof;
  (ii) at least 95%, or at least 90%, of said particles has a diameter of less than or equal to 600 nm, preferably, less than or equal to 300 nm (for example, between 140 and 250 nm); and
  (iii) said particles have a z-average diameter of less than or equal to 200 nm, preferably less than or equal to 150 nm, in particular, as measured according to ISO 22412:2017.

In a preferred embodiment, the present invention relates to an aqueous composition comprising particles wherein:
  (i) each of said particles comprises a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
  (ii) at least 90% of said particles has a mono-modal diameter distribution below 300 nm;
  (iii) said particles have a z-average diameter of less than or equal to 200 nm, as measured according to ISO 22412:2017; and
  (iv) said composition has a zeta potential equal or superior to 30 mV, preferably between 35 and 50 mV, according to ISO 13099-2:2012.

The present invention also relates to an aqueous composition comprising particles as disclosed herein wherein:
  (i) each of said particles is formed by making a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
  (ii) at least 90% of said particles has a mono-modal diameter below 300 nm;
  (iii) said particles have a z-average diameter of less than or equal to 200 nm, as measured according to ISO 22412:2017; and
  (iv) said composition has a zeta potential equal or superior to 30 mV, preferably between 35 and 50 mV, according to ISO 13099-2:2012;
wherein said particles are formed at the ratio of the number of moles of nitrogen of said polyalkyleneimine to the number of moles of phosphorus of said double-stranded polyribonucleotide in said composition being equal to or greater than 2.5.

The present invention also relates to a composition obtainable by lyophilisation of the aqueous composition as disclosed herein.

These compositions can be further defined on the basis of the features associated to the following criteria: a pH comprised between 2 and 4 and a concentration of one double-stranded polyribonucleotide equal or superior to 0.5 mg per mL of the total volume of said composition.

These compositions can be further defined on the basis of amount and size of the double-stranded polyribonucleotides, in particular:
  (i) at least 40% of the double-stranded polyribonucleotides comprised in said particles have at least 850 base pairs, and at least 50% of the double-stranded polyribonucleotides comprised in said particles have between 400 and 5000 base pairs; and/or
  (ii) between 5% and 60% of double-stranded polyribonucleotides having less than 400 base pairs, between 15% and 30% of double-stranded polyribonucleotides having between 400 and 850 base, between 10% and 70% of double-stranded polyribonucleotides having between 850 and 5000 base pairs, and between 0% and 10% of double-stranded polyribonucleotides having more than 5000 base pairs.

These compositions have been successfully optimized for pharmaceutical manufacturing and clinical use, in particular by identifying the optimal and more reproducible combinations of components, physical and/or chemical criteria, and related numerical ranges (applicable to either the particles or the compositions) for the desired uses and methods. Thus, a further preferred composition is an aqueous composition comprising particles wherein:
  (i) each of said particles comprises a complex of
    (a) polyinosinic-polycytidylic acid [poly(I:C)], or a salt or solvate thereof, wherein at least 40% of poly(I:C) molecules comprised in said particles have at least 850 base pairs, and at least 50% of poly(I:C) molecules comprised in said particles have between 400 and 5000 base pairs, and
  (b) a water-soluble, linear homo-polyalkyleneimine or hetero-polyalkyleneimine, or a salt and/or solvate thereof, wherein the average molecular weight of said linear polyalkyleneimine is between 17 and 23 kDa
(ii) at least 90% of said particles has a mono-modal diameter distribution below 300 nm (and preferably below 250 nm);
(iii) said particles have a z-average diameter of between 60 nm and 130 nm diameter (and more preferably of 80+/−20 nm), as measured according to ISO 22412: 2017, with polydispersity index of said particle diameter which is inferior to 1.5;
(iv) said composition contains poly(I:C) at a concentration of at least 0.5 mg/mL;
(v) said composition has: a pH of between 2 and 4 and osmolality of between 200 and 600 mOsm/kg; and
(vi) said composition has a zeta potential between 35 mV and 50 mV, according to ISO 13099-2:2012.

These ranges identified in aqueous composition and particles defined above can be further defined and/or limited to:
  (i) particles comprising at least 10% of poly(I:C) molecules have less than 400 base pairs, at least 40% of poly(I:C) molecules having at least 850 base pairs, at least 70% of poly(I:C) molecules having between 400 and 5000 base pairs, and between 20% and 45% of poly(I:C) molecules having between 400 and 850 base pairs;
  (ii) particles comprising between 5% and 60% of poly(I:C) molecules having less than 400 base pairs, between 15% and 30% of poly(I:C) molecules having between 400 and 850 base, between 10% and 70% of poly(I:C) molecules having between 850 and 5000 base pairs, and between 0% and 10% of poly(I:C) molecules having more than 5000 base pairs.
  (iii) said particles have a median diameter (D50%) of between 75 nm and 150 nm (and preferably at least have a median diameter of 85+/−20 nm);
  (v) the water-soluble, linear homo-polyalkyleneimine or hetero-polyalkyleneimine being a linear polyethyleneimine;
  (vi) the polydispersity index of said particle diameter is comprised between 0.2 and 0.3;
  (vii) the composition having a pH 3.0+/−0.2 and an osmolality of between 300 and 310 mOsm/kg.

In addition, the present invention relates to a composition, i.e. BO-11X formulations or compositions as disclosed herein, for use as a medicament, alone in combination with other therapeutic agents. These compositions may further comprise at least one pharmaceutically acceptable carrier, organic solvent, excipient and/or adjuvant, either included in the particles themselves or added in the aqueous composition, for example glucose added in a concentration of between 1 and 10% (weight/volume). Moreover, the composition may further comprise at least one compound, and in particular a therapeutic compound, selected from an organic compound, an inorganic compound, a nucleic acid (for example, non-coding RNA or RNA coding for proteins), an aptamer, a peptide or a protein, either included in the particles themselves or added in the aqueous composition.

Moreover, this composition can be administered for medical uses using regimens that combine different routes of administration (e.g. one or more intra-tumoral injections that are followed by one or more sub-cutaneous or intra-muscular injections over a period of 1 or more weeks) and/or the ex vivo exposure of human cells to the composition, prior to re-administering the cells to the patient. In this latter case, such regimen involves the induction of specific activities within the cells of the patient that are exposed to the composition, for instance, the induction of interferon production by said cells in vitro. Otherwise, in vitro and/or ex vivo studies with respect to immune response to such composition show that BO-11X compositions trigger other biological mechanisms (interferon-independent and/or targeting immune cells, for example) that can be exploited for promoting therapeutically relevant events such as tumor cell death, enhanced local and/or systemic T cell immune response either directly (within injected tumors) or in distant tumors, and other mechanisms that may be useful for treating cancers that are recurrent, unresponsive or refractory to other therapies.

The dose of the composition, in particular with respect to the content of double-stranded polyribonucleotides, can be adapted consequently to each type of administration, regimen (e.g. highest for intra-tumoral injection, lower for sub-cutaneous or intra-muscular injection, and even lower for treating cells ex vivo, and/or other drugs (when administered in combination therapies). The present invention also relates to a composition, as disclosed herein, for use in treatment or prevention of a cell growth disorder characterized by abnormal growth of human or animal cells, preferably cancer, and most preferably solid cancers or lymphomas. Furthermore, this composition can be administered for supporting vaccines, cytokines, antigens, antibodies, chemical compounds, and other compounds having immunomodulatory activities for treating or preventing cancers (solid or not) or infection, for instance as adjuvant and/or for rescuing patients poorly responding or resistant to a drug, including agents for cancer immunotherapy, for altering cell metabolism and/or functions (preferably, in immune and/or cancer cells), for modulating DNA expression, replication and/or repair (including drugs that target epigenetic mechanisms), or for standard-of-care therapies (such as chemo- or radiotherapy, or vaccine-based therapies involving cancer or viral antigens).

Other objects of the present invention are related to the methods related to the composition, as disclosed herein, for evaluating the efficacy, the most appropriate regimen, the most appropriate therapeutic combination with another anti-cancer drug or standard-of-care protocol, and/or subjects presenting the best response to the treatment with a BO-11X treatment. These methods involve measuring the up- and down regulation in the expression of panels of genes in selected cell types (such as immune cells and cancer cells) following to the exposure to a BO-11X composition and consequently applying appropriate means for improving therapeutic efficacy (e.g. for stratifying or selecting patients for further treatments, administering or not drugs targeting specific biological targets, and/or reducing or increasing the dosage of BO-11X and/or other compositions). Furthermore, the present invention relates to a process of manufacturing a composition, i.e. BO-11X formulations or compositions as disclosed herein, which comprises:
  (i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;

(ii) independently filtering each solution through a filter having a pore diameter of less than or equal to 500 nm to form sterilized solutions;
(iii) mixing the resulting sterilized solutions in a mixing chamber to form an aqueous composition by addition of one of said solutions into the other solution in said mixing chamber, optionally by injection, at a rate of greater than or equal to 1 mL/min, or by simultaneous addition of each of said solutions into said mixing chamber, optionally by injection, at a rate of greater than or equal to 1 mL/min; and optionally
(iv) filtering the resulting aqueous composition through a filter having a pore diameter of less than or equal to 600 nm to form a filtrate, or centrifuging the resulting aqueous composition at greater than or equal to 22480 m/s$^2$ to form a supernatant.

The present invention also relates to the aqueous composition obtainable by said process (including the compositions that can be defined as light suspensions), as well as the compositions that can be optionally obtained by lyophilising the resulting aqueous composition, filtrate or supernatant and then provided and/or used separately (or in kits) with other medical compounds or devices (such as buffers, diluents, catheters, needles, filters, or devices adapted for intratumoral administration).

Preferably, the present invention also relates to a composition comprising particles wherein:
(i) each of said particles comprises a complex of at least one double-stranded polyribonucleotide, or a salt or solvate thereof, and at least one polyalkyleneimine, or a salt and/or solvate thereof, wherein
  (a) said double-stranded polyribonucleotide is polyinosinic-polycytidylic acid [poly(I:C)] or polyadenylic-polyuridylic acid [poly(A:U)], wherein at least 10% of double-stranded polyribonucleotides have less than 400 base pairs, at least 40% of said double-stranded polyribonucleotides have at least 850 base pairs, at least 70% of said double-stranded polyribonucleotides have between 400 and 5000 base pairs, and between 20% and 45% of said double-stranded polyribonucleotides have between 400 and 850 base pairs; and
  (b) said polyalkyleneimine comprises at least 95% polyethyleneimines, wherein the weight average molecular weight of said polyalkyleneimine is between 17 and 23 kDa and the polydispersity index is <1.5, and wherein the ratio of the number of moles of nitrogen of said polyalkyleneimine to the number of moles of phosphorus of said double-stranded polyribonucleotide in said composition is between 2.5 and 5.5;
(ii) at least 99% of said particles has a diameter of less than or equal to 600 nm; and
(iii) said particles have a z-average diameter of between 30 nm and 150 nm.

More preferably, the present invention also relates to an aqueous composition which comprises particles wherein:
(i) each of said particles comprises a complex of at least one double-stranded polyribonucleotide, or a salt or solvate thereof, and at least one polyalkyleneimine, or a salt and/or solvate thereof, wherein
  (a) said double-stranded polyribonucleotide is polyinosinic-polycytidylic acid [poly(I:C)], wherein at least 10% of double-stranded polyribonucleotides have less than 400 base pairs, at least 40% of said poly(I:C) has at least 850 base pairs, at least 70% of said poly(I:C) has between 400 and 5000 base pairs, and between 20% and 45% of said poly(I:C) has between 400 and 850 base pairs; and
  (b) said polyalkyleneimine is polyethyleneimine (PEI), wherein the weight average molecular weight of said PEI is between 17.5 and 22.6 kDa and the polydispersity index is <1.5, and wherein the ratio of the number of moles of nitrogen of said polyalkyleneimine to the number of moles of phosphorus of said double-stranded polyribonucleotide in said composition is between 2.5 and 4.5;
(ii) at least 99% of said particles has a diameter of less than or equal to 500 nm;
(iii) said particles have a z-average diameter of between 60 nm and 130 nm; and
(iv) said particles have a median diameter (D50%) of between 75 nm and 150 nm.

Any of the compositions as defined above can be further defined with respect to features of the manufacturing process, including compositions obtainable by lyophilisation of the aqueous composition defined above. For example, the particles are formed at the ratio of the number of moles of nitrogen of said water-soluble, linear homo-polyalkyleneimine or hetero-polyalkyleneimine to the number of moles of phosphorus of poly(I:C) molecules between 2.5 and 4.5. Preferably, the particles are formed by injecting separately the solution containing said poly(I:C) molecules and the solution containing said water-soluble, linear homo-polyalkyleneimine or hetero-polyalkyleneimine in a mixing chamber. The aqueous compositions can be formed by adding glucose in a concentration of between 1 and 10% (weight/total volume of said composition), preferably by adding glucose to the solution containing poly(I:C). Moreover, wherein the solution containing said poly(I:C) molecules and the solution containing said water-soluble, linear homo-polyalkyleneimine or hetero-polyalkyleneimine are injected separately, wherein the flow speed for injecting either solution is between 1 mL/min and 50 mL/min, and/or mixed at a speed between 50 rpm and 600 rpm.

The more preferred ranges that are identified above within (i)-(vii) above with respect to the sizes of poly(I:C) molecules contained in the particles, the mono-modal diameter distribution of particles the linear polyalkyleneimine being polyethyleneimine, the polydispersity index of particle diameter, the osmolality of composition, and/or pH of composition (as well the presence one pharmaceutically acceptable carrier, organic solvent, excipient and/or adjuvant, or the presence of at least one compound, and in particular a therapeutic compound) also apply to the aqueous compositions which comprises particles that are formed as indicated above.

Further embodiments related to the preparation of such compositions in form of BO-11X formulations, their features, their analysis, and their uses (alone or in combination with other agents, as well as in specific regimens) are provided in the Detailed Description and in the Examples below, in particular for obtaining improved or optimized therapeutic responses for specific indications and/or in combination with other drugs and therapies (such as chemotherapy, radiotherapy, agents that target immune checkpoint molecules, T cell-mediated responses, DNA repair and/or replication, or inhibitors of kinases and other enzymes that modulate activities in immune cells and/or cancer cells, including metabolic activities). BO-11X formulations can be used in methods for treating a cell growth disorder characterized by abnormal growth of human or animal cells (and in particular cancer) in combination with a second therapeutic agent selected from anti-CTLA4, anti-PD1, anti- PDL1, CAR-T cells, cancer antigen vaccines, or agents that target regulatory T cells, metabolic enzymes, DNA repair and/or replication, or a protein expressed by any of the genes of Table I (see Example 4). More particularly, BO-11X formulations can used for obtaining a synergistic therapeutic effect when administered with this second therapeutic agent, including the possibility of reducing the regular dosage and/or frequency of administration of said second therapeutic agent (thus potentially reducing medical interventions, resistance to drugs, and/or patient's discomfort). Moreover, BO-11X formulations when administered with this second therapeutic agent, may allow treating patients that are resistant, insensitive, or poorly (or not) responding to said second therapeutic agent, overcoming any specific tumor resistance or escape mechanism (including mutations that alter specific genes, pathways, and/or response to drugs or endogenous compounds such as cytokines). Thus, BO-11X formulations can be used in the form of a drug-rescuing or drug-sensitizing combination treatment, in particular for treating cancer.

all groups but G1, received intraperitoneal (i.p.) administration of an anti-PD-L1 murine antibody (150 μg/dose) in addition to the intratumoral administration of BO-112 formulation at the same concentration of day 7. Survival was monitored daily, and mice were scored as dead upon finding them deceased, or when the tumor volume reached the maximum allowed size. Monitoring continued after last treatment until day 45, when the last mouse died and the experiment was terminated. (B) Survival curve comparing the control groups G1 and G5 with the three groups in which BO-112 formulation was administered at the indicated three concentrations. When comparing the groups, there was a statistical difference (p<0.0001, Log-rank Mantel-Cox test) between the control groups and the test groups, with G4 showing the strongest increase of survival relative to vehicle or anti-PD-L1 alone. (C) Therapeutic effect of BO-112 as single agent in a further B16-F10 model for human melanoma; B16-F10 melanoma cells ($5 \times 10^5$ cells) are injected sub-cutaneously and BO-112 is administered intratumorally as described in A (8-9 mice/group; control group, vehicle only; treatment group, BO-112; BO-112 dose/mouse: 2.5 mg/Kg in 100 μl). (D) The size of tumors was measured by calliper weekly and volume calculated (length×width$^2$/2) for each animal. Spider plots show individual tumor growth curves for control (vehicle) and BO-112 treated mice and indicate that BO-112 formulation reduces tumor growth compared to vehicle.

Figure 7:
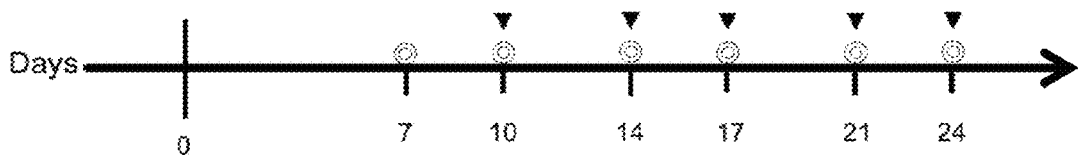
FIG. 7: Effect of BO-112 administration in an animal model for human melanoma. (A) Timeline showing the schedule of treatment. All mice were injected sub-cutaneously with B16-F10 murine melanoma cells at day 0. After randomizing mice into five groups presenting tumors of similar average size (80-100 mm³) on day 7, animals were treated with BO-112 formulation (double circles) by injection straight into the tumor tissue (i.t. treatment) at 3 different concentrations in groups 2, 3, and 4 (G2, G3, G4) or, in the two remaining groups (G1 and G5), with vehicle only. On the following treatment days (10, 14, 17, 21 and 24)
Figure 7:
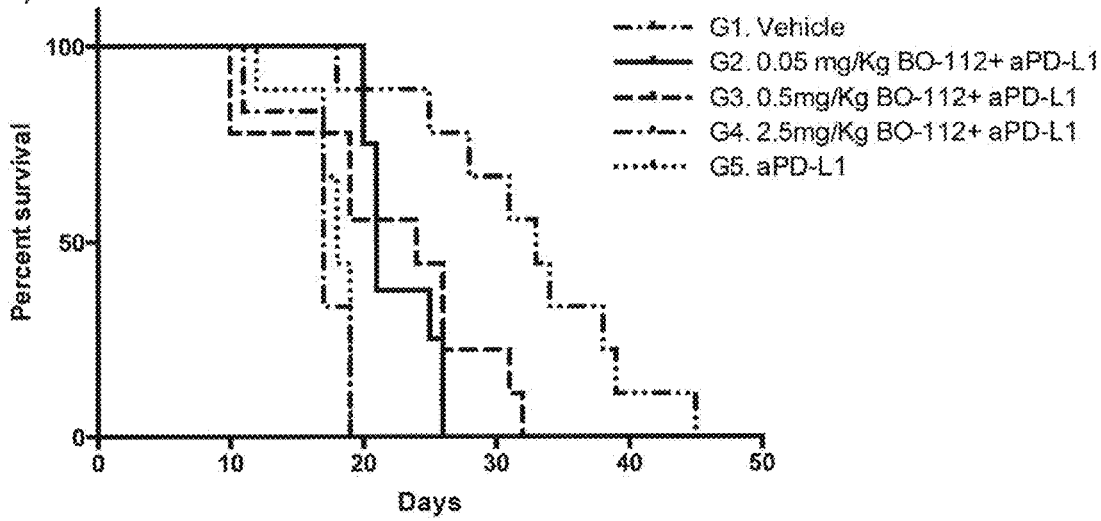
Figure 7:
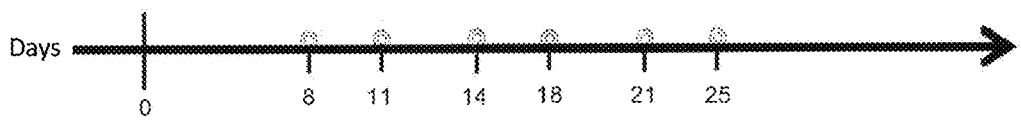
Figure 7:
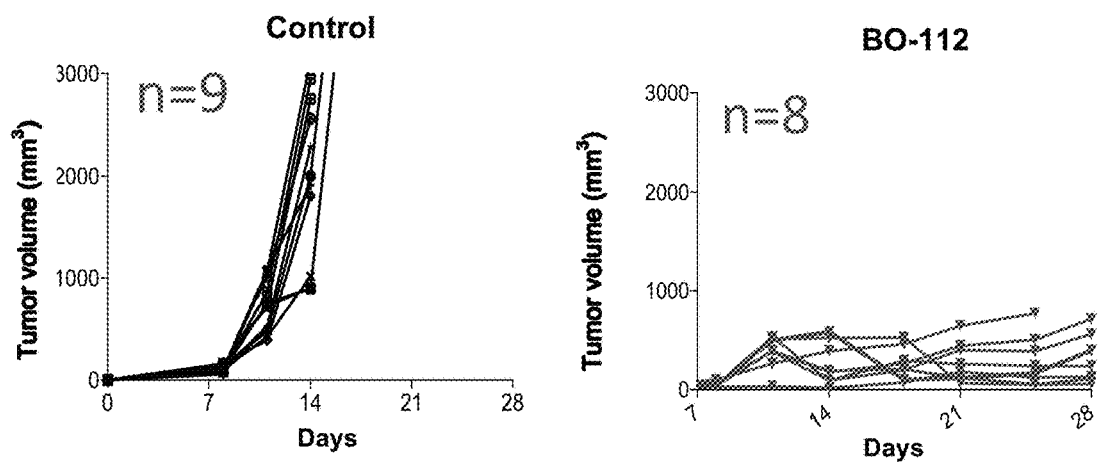
Figure 8:
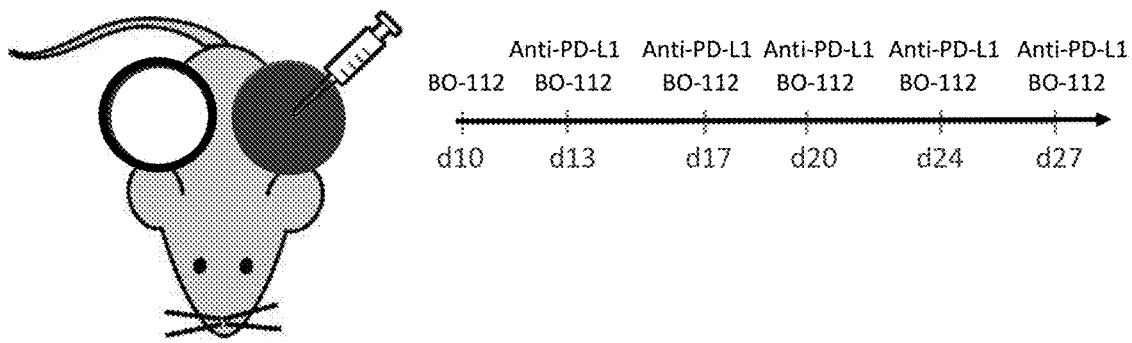
Figure 8:
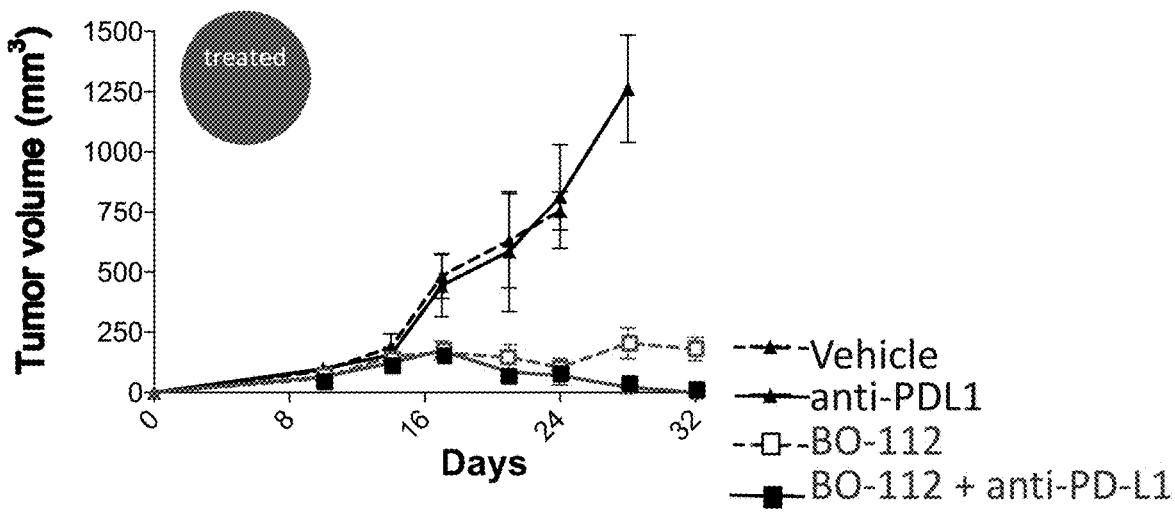
Figure 8:
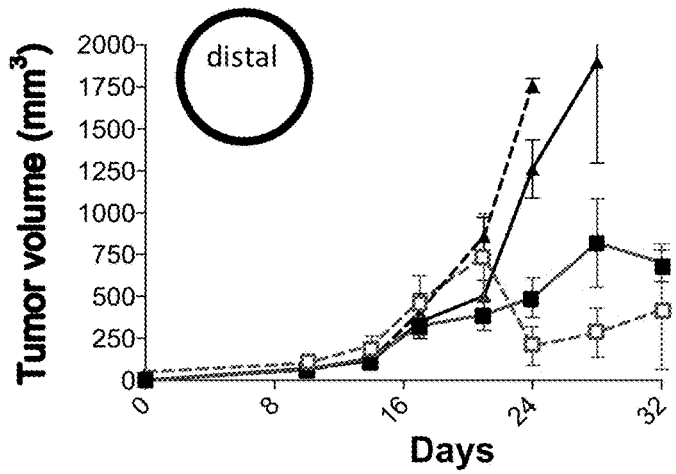

FIG. 8: Abscopal effect of BO-112 administration in an animal model for human melanoma. (A) Mice in which two cancers are induced by transferring melanoma B16-F10-OVA are treated in only one one tumor mass by intratumoral administration (for BO-112) and/or systemically by intraperitoneal administration (for anti-PD-L1), using a regimen and dosage similar to those of the experiment shown in FIG. 7 (n=10 mice/group). (B) The growth of tumor volume was measured in both the treated and untreated, distal tumor masses in the four groups: control, single treatment, or combined treatment. Tumors were measured by calliper weekly and volume calculated (length×width$^2$/2) for each animal in a group.

Figure 9:
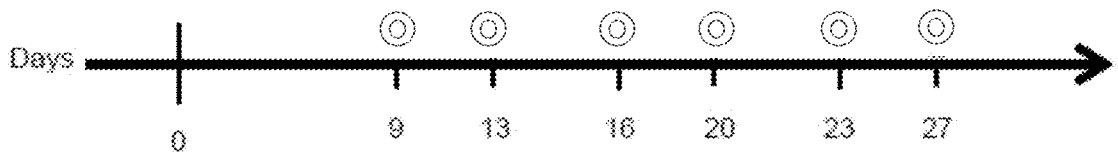
Figure 9:
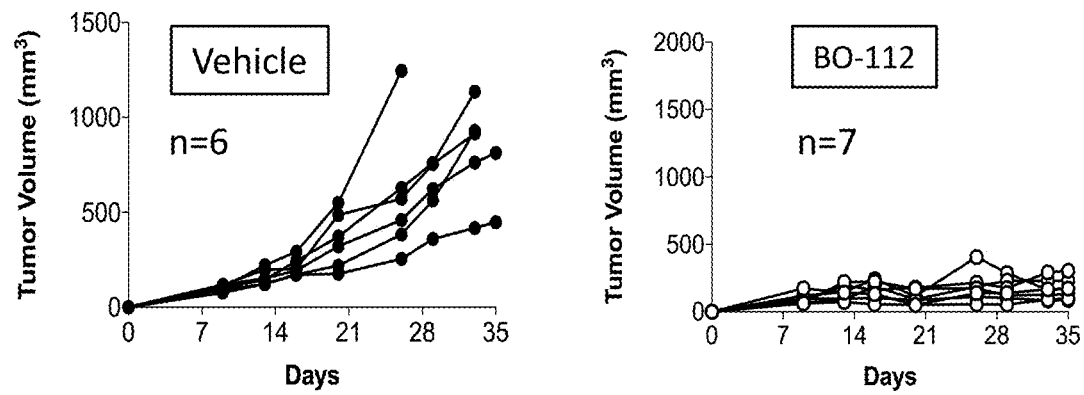
Figure 9:
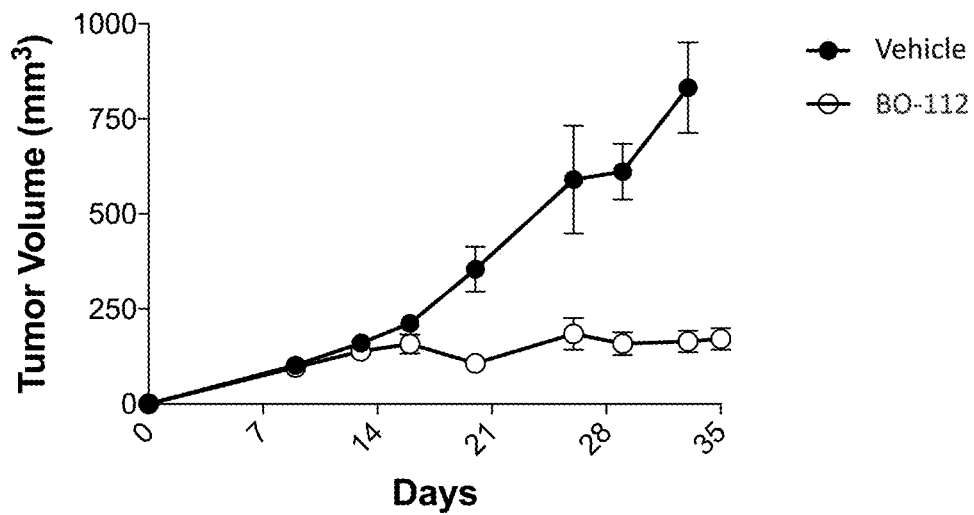

FIG. 9: Effect on BO-112 administration in an animal model for human breast cancer. (A) Model and treatment scheme using 4T1 breast carcinoma cells ($5 \times 10^5$ cells) that were injected sub-cutaneously (s.c.) in the right flank of 8- to 10-week-old female BALB/c mice (6-7 mice/group; control group, vehicle only; treatment group, BO-112). Treatments started when tumor volume was 80-100 mm$^3$ (on day 9). BO-112 administration and vehicle was performed intratumorally via a single direct injection into the tumor mass of the right flank (dose/mouse: 2.5 mg/Kg in 100 μl) at the indicated days. Tumors were measured by calliper weekly and volume calculated (length×width$^2$/2) for each animal in a group, obtaining data that are shown separately for each of such animals (the number of animals for each group is indicated (B), or in consolidated for each group (C), observing a statistically relevant decrease of tumor volume in the BO-112 treated group.

Figure 10:
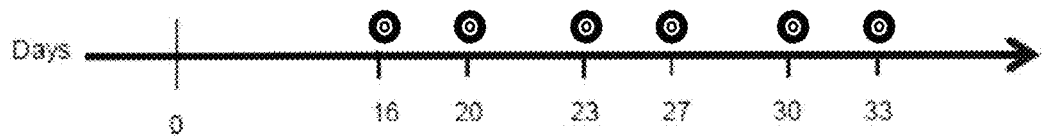
Figure 10:
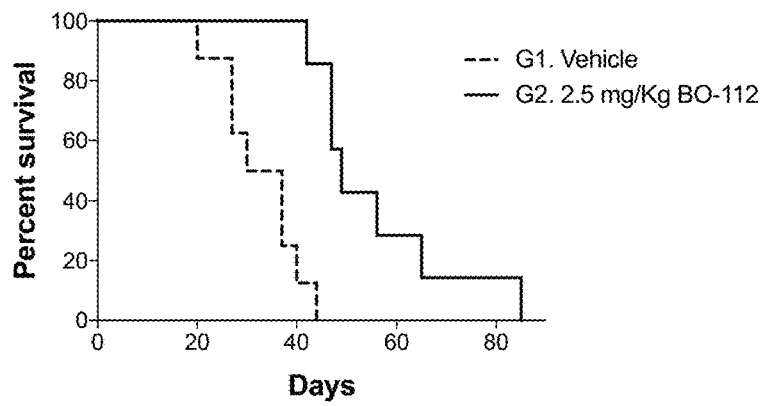
Figure 10:
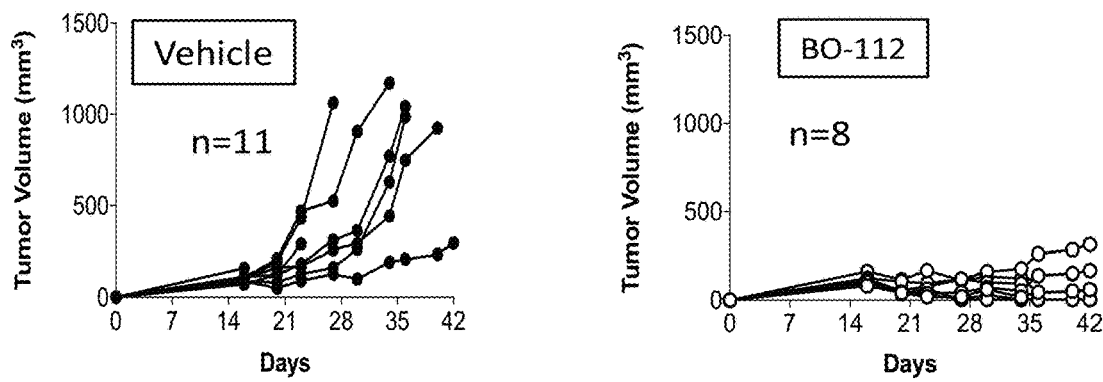
Figure 10:
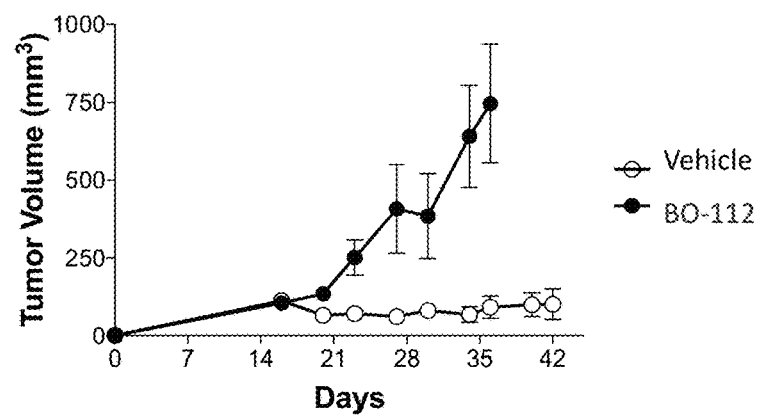

FIG. 10: Effect on BO-112 administration in an animal model for human colorectal cancer. (A) In a first model and treatment scheme, MC38 colon carcinoma cells ($5 \times 10^5$ cells) were injected s.c in the right flank of 8- to 10-week-old female C57BL/6 mice (7-8 mice/group; G1 control group, vehicle only; G2 treatment group). Treatments started when tumor volume was 80-100 mm$^3$ (on day 16). BO-112 administration and vehicle was performed intratumorally via a single direct injection into the tumor mass of the RIGHT flank (dose/mouse: 2.5 mg/Kg in 100 μl) at the indicated days. (B) Mouse survival in this first model was evaluated using Kaplan-Meier analysis. Tumors were also measured by calliper weekly and volume calculated (length×width$^2$/2) for each animal in a group obtaining data that are shown separately for each of such animals (C) or in consolidated for each group (D), observing a statistically relevant decrease of tumor volume in the BO-112 treated group.

Figure 11:
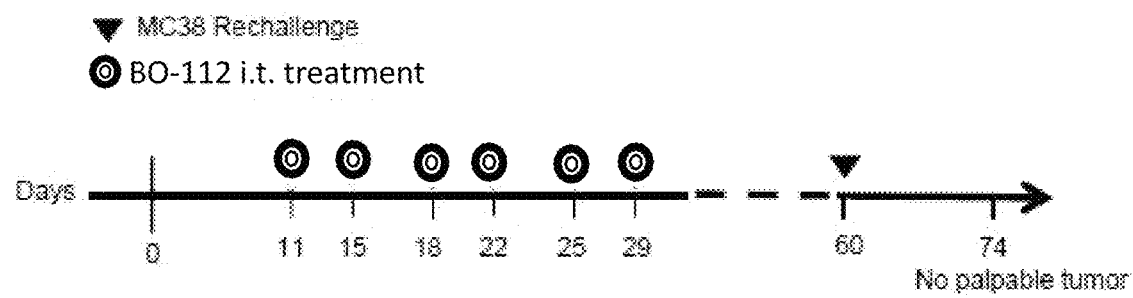
Figure 11:
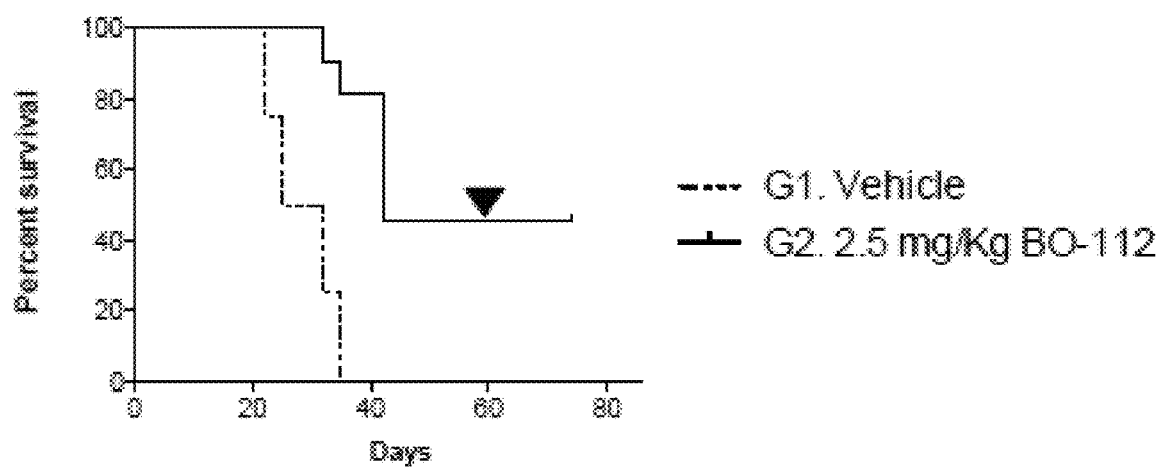

FIG. 11: Effect on BO-112 administration in a second model for human colorectal cancer using a different treatment scheme. (A) MC38 colon carcinoma cells ($1 \times 10^6$ cells) were injected s.c in the right flank of 8- to 10-week-old female C57BL/6 mice (4-11 mice/group; G1 control group, vehicle only; G2 treatment group). Treatments started when tumor volume was 80-100 mm$^3$ (on day 11). BO-112 administration and vehicle was performed intratumorally via a single direct injection into the tumor mass of the right flank (dose/mouse: 2.5 mg/Kg in 100 μl) at the indicated day. In those remaining mice that were tumor-free after BO-112 treatment, a re-challenge was done on day 60 using MC38 cells ($2.5 \times 10^5$ cells) that were injected s.c in the left flank, following tumor growth and mouse survival. (B) Mouse survival in this second model was also evaluated using Kaplan-Meier analysis, with the four animals that were re-challenged at day 60 and still alive at day 80, suggesting that BO-112 can both trigger apoptosis of cancer cells and drive immune memory against them.

Figure 12:
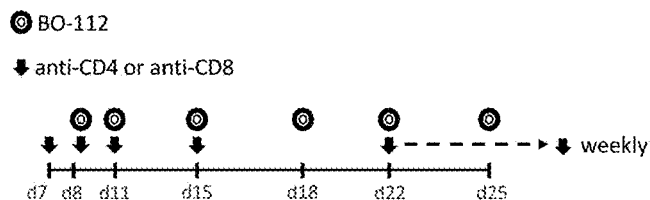
Figure 12:
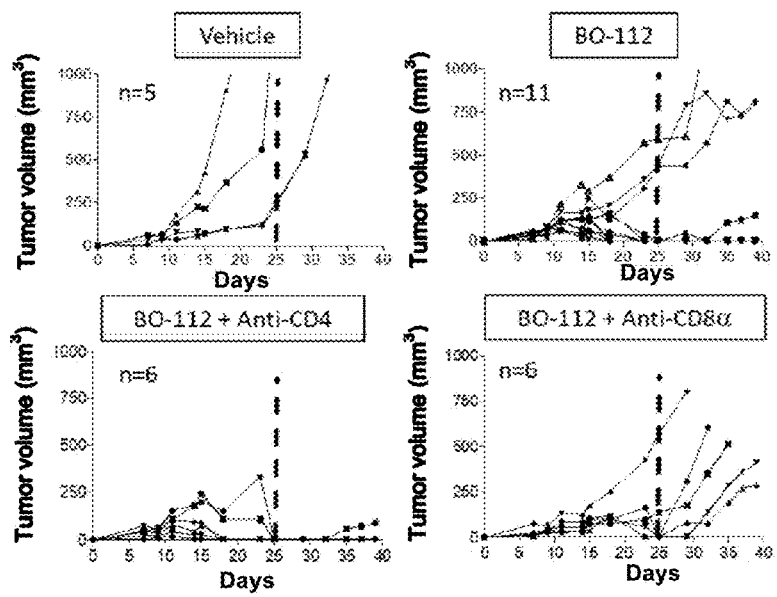
Figure 12:
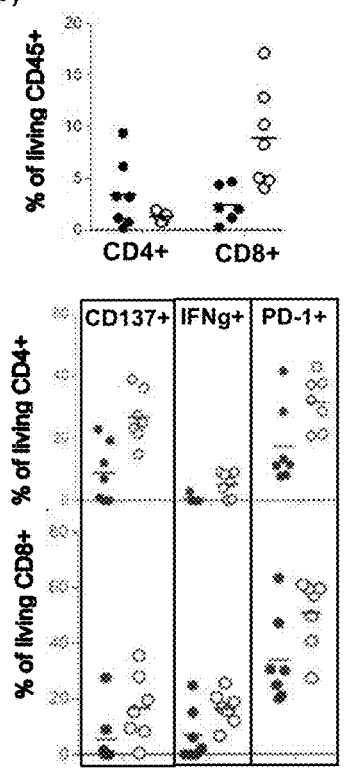
Figure 12:
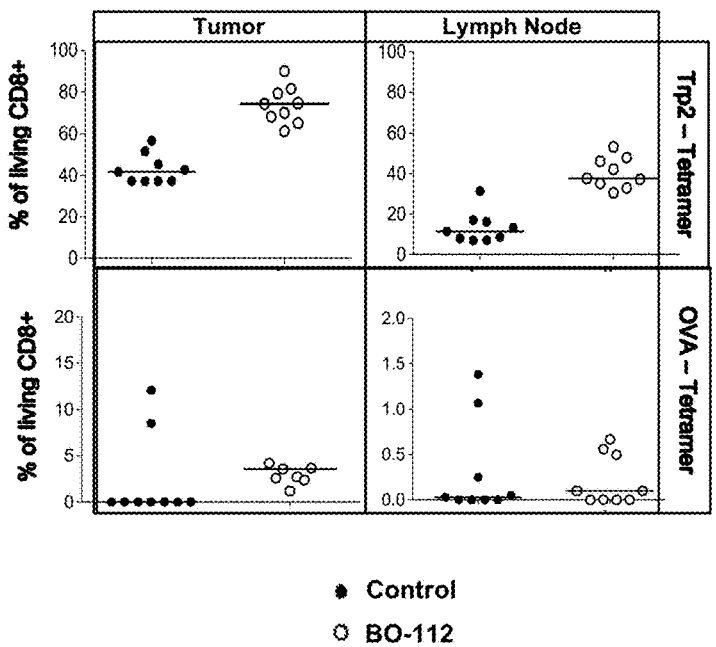

FIG. 12: BO-112 therapeutic effect in models for adaptive immune response activation in human cancers. (A) The MC38-based model for human colon carcinoma is established as previously described but integrating two further groups in which an antibody for depleting either CD4positive or CD8positive T cells is also administered (treatment schedule: B0112: d8, d11, d15, d18, d22, d25; anti-CD4 or anti-CD8: d7, d8, d11, d15, d22, d29). (B). Analysis of the tumor growth curves of MC38 tumor-bearing mice treated with BO-112, showing that only the depletion of CD8positive T cells diminishes the therapeutic properties of BO-112 formulation (tumor volume is shown in parallel for the different groups, N for the number of mice per group and with a dotted line indicating the end of BO-112 treatment at d25). (C) Effect of BO-112 therapy on T cell recruitment and activation into the tumor, and on the priming of antigen specific CD8+ T cells. Frequency of different cell markers for T cell subsets (CD8 positive or CD4 positive) ad T cell activation (CD137, IFN-γ and PD-1) is measured in B16-F10-OVA tumors (and in draining lymph nodes for tetramer analysis) from mice treated with vehicle or BO-112 formulation 24 hours after the second BO-112 administration by flow cytometry. The graphs show that BO-112 therapy significantly increases CD8+ T cells and promotes CD4+ and CD8+ T cell activation in the tumor infiltrate in this model. (D) Frequency of different cell markers for T cell subsets (CD8 positive or CD4 positive) for T cell priming (OVA and Trp2 tetramers), showing that BO-112 also enhances significantly the frequency of Antigen-specific CD8+ T cells in the tumor (against OVA and endogenous Trp2 Antigens) and in the draining lymph node (particularly for Trp2 Antigen) with significant. All data (even originate from different experiments) consistently indicate that BO-112 formulation activates the anti-tumor adaptive immune response with the potential to induce systemic immunity.

Figure 13:
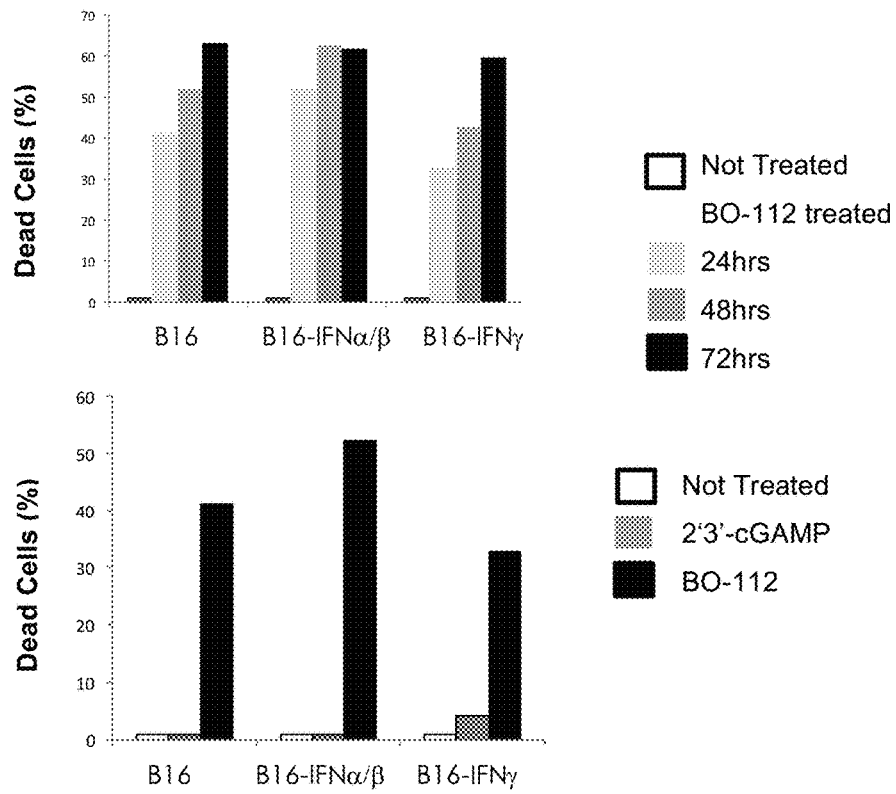
Figure 13:
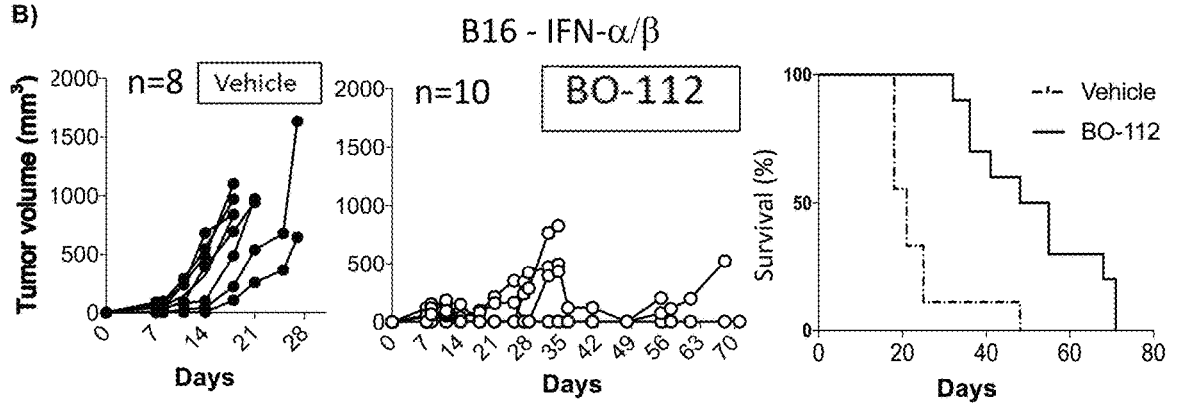
Figure 13:
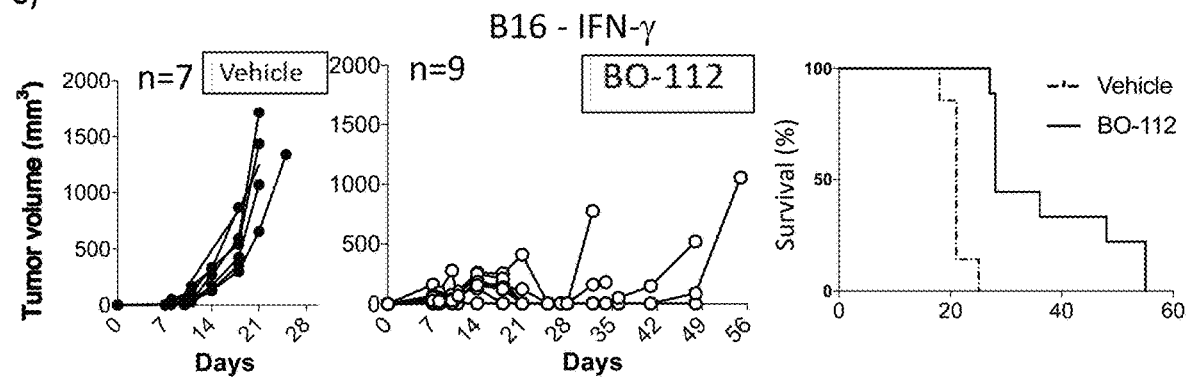

FIG. 13: BO-112 therapeutic effect in models for evaluating dependency from interferons expression in human cancers. (A) The in vitro tumor cell cytotoxicity independent of IFNs is evaluated in terms of cell viability at 24, 48 and 72 h by MTS assay. Briefly, cells from each cell line: B16, B16-IFN α/β (do not respond to IFNγ; from InvivoGen) and B16-IFNγ (do not respond to IFNα/β; from InvivoGen) were cultured ($5 \times 10^3$ cells/well, 96 flat-well plates): alone or with BO-112 at 0.5 µg/ml for 24, 48, and 72 hours alone or alternatively with BO-112 (0.5 µg/ml), or with 2'3'cGAMP STING agonist (7 µg/ml) for 24 hours (showing BO-112 superiority in efficacy to a reference STING agonist). Two independent assays were performed, with at least 8 wells per condition. The In vivo therapeutic effect of BO-112 on IFNs resistant B16-based model for human melanoma were tested in the above described B16-IFN α/β (B) and B16-IFNγ (C) cancer cells were injected s.c in the RIGHT flank ($5 \times 10^5$ cells) of 8- to 10-week-old female C57BL/6 mice (7-10 mice/group). Treatments started when tumor volume was 80-100 mm$^3$ (on day 8). BO-112 administration and vehicle was performed intratumorally via a single direct injection into the tumor mass of the RIGHT flank (BO-112 dose/mouse: 2.5 mg/Kg in 100 µl; 2 doses/week, 3 weeks). Tumors were measured by caliper weekly until sacrificed and volume calculated. Graphs show that BO-112 reduces tumor volume (individual spider plots) and improves significantly survival (Kaplan-Meier curves) in BO-112 treated mice compared to vehicle, indicating that BO-112 formulation has a potent therapeutic effect in IFNs-resistant cancer cells.

Figure 14:
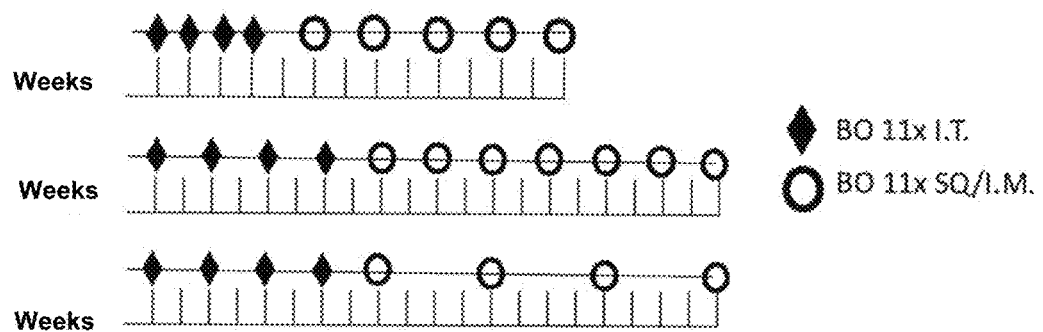
Figure 14:
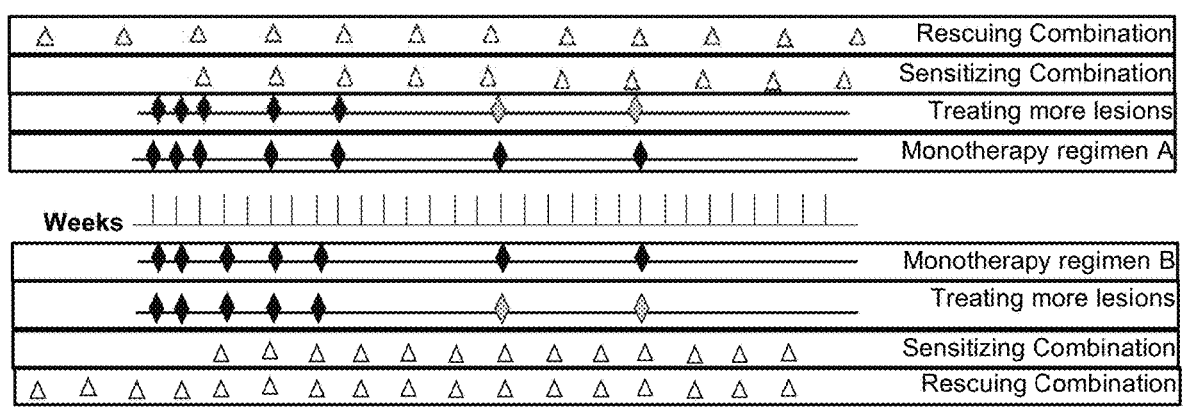
Figure 14:
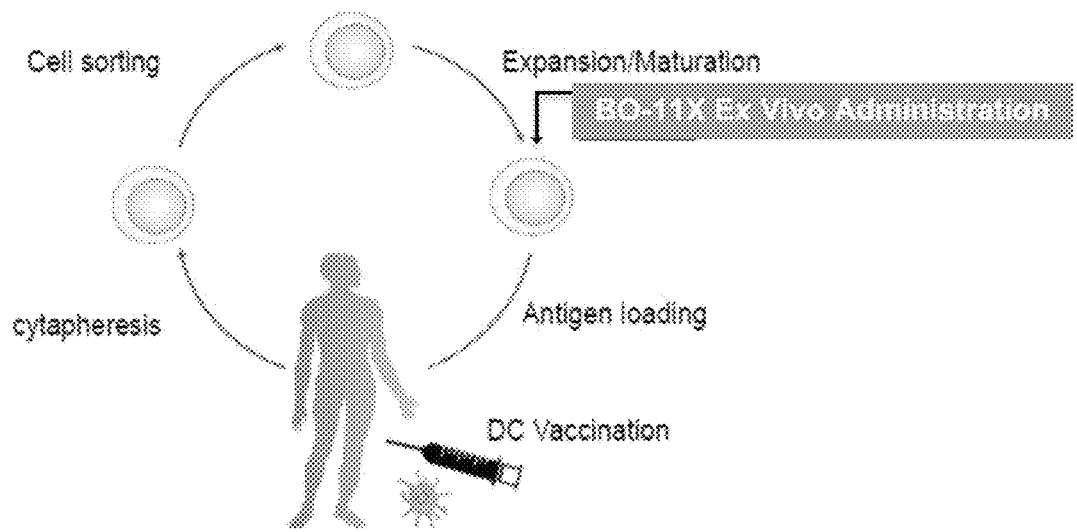

FIG. 14: Alternative means and regimens for BO-11X administration. (A) the administration of a BO-11X formulation such as BO-112 may start with 1-4 doses of intratumoral injections (BO-11XI.T.) to be made every week, every two weeks, or every three weeks (0,4-2.4 mg/dose; or with a larger interval of up to every 6 weeks, as it can be done in responding or stable patients during clinical studies). The initial doses can be followed by a number of sub-cutaneous or intramuscular injections of BO-11X (BO-11XSQ/I.M.; 0.2-2 mg dose). As for other intra-tumoral treatments, this regimen may involve the injection of same lesion (if still present) or other lesion if original lesion is no longer present or if the initial intratumoral injections have not reduced such lesions (through systemic immune activation or other response) or other evidences of tumor burden, stage, persistence, metastasis, and/or recurrence. (B) Alternatively, BO-112 administration can be pursued by intratumoral injections that are progressively spaced (every week, every two, four, six or more weeks) during 20 or weeks, alternating I.T. administration in the same (black diamonds) and other cancer lesions (grey diamonds), with or without administering in parallel treatments such as chemotherapy, radiotherapy, small molecule, checkpoint inhibitor, antibody (triangles, administered once every 2 weeks or once every 3 weeks as examples) in other regimens and/or administrations that are started before or after the BO-11X treatment. In the former case, the initial BO-11X monotherapy regimen A can be combined (for example, with pembrolizumab or ipilimumab) or BO-11X monotherapy regimen B can be combined (for example, with nivolumab) for rescuing or supporting the treatment of this second therapeutic agent which otherwise would be poorly (or not) effective. In the latter case, either BO-11X monotherapy regimen A or initial BO-11X monotherapy regimen B (each of two regimens combined with the antibodies previously cited) allows sensitizing the tumor (or the patient) to the additional therapeutic agent (in particular, an immunotherapy). (C) As an adjuvant to be used ex vivo on cells obtained from patients (such as a vaccine adjuvant for ex vivo maturation of dendritic cells, DCs), the treatment may start by obtaining a blood sample from a patient for isolating relevant cell types by cytapheresis, a procedure for separating cells by positive selection and cell sorting such a subset of Dendritic Cells (DCs), for example monocyte-derived dendritic cells (Mo-DCs), BDCA3-positive and other subsets of dendritic cells that are major producers of Type I Interferon in response to stimuli such as poly(I-C) molecules, or CD34+–derived dendritic cells. These cells can be then expanded and/or matured ex vivo for a given number of days, during which cells are exposed to BO-112 formulations for variable number of hours (e.g. 1 hour, 3 hrs, 8 hrs, 24 hrs or more), and then used for antigen loading to complete the preparation of a DCs-based vaccination. Such an activation of DCs can be also followed and completed (or directly achieved) through intra-muscular or sub-cutaneous injection of BO-112, the induction of immunogenic cell death in tumors by intra-tumoral injection of BO-112, and/or by in vivo delivery of tumor antigens.

Figure 15:
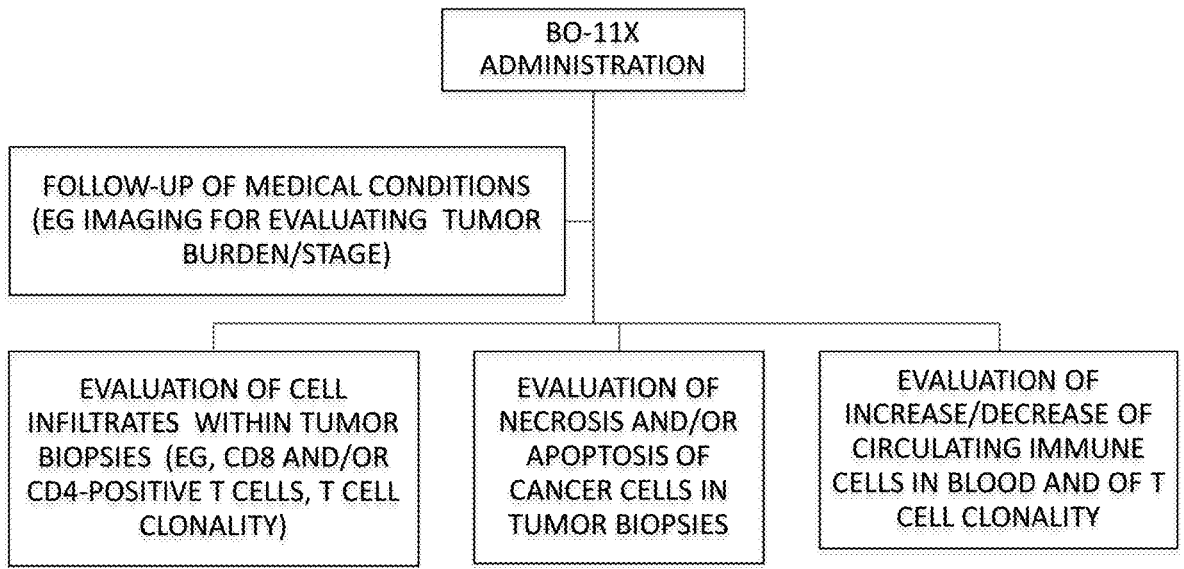
Figure 15:
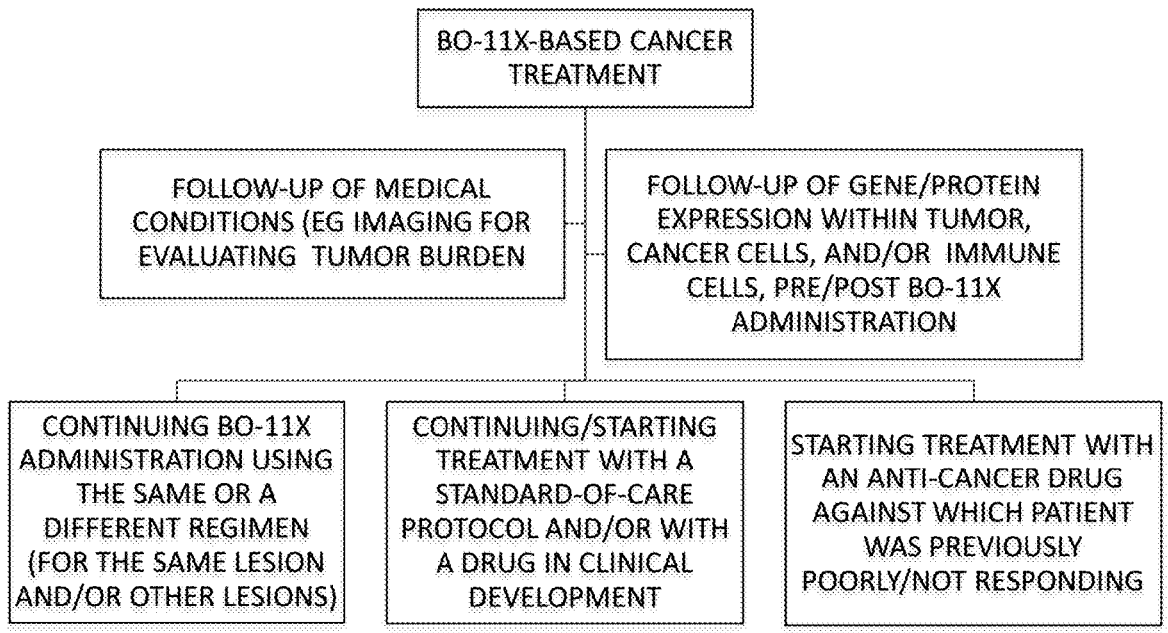

FIG. 15: Alternative means for evaluating and using BO-11X in patients. (A) Flowchart summarizing medically relevant readouts to evaluate administration of a BO-11X formulation such as BO-112. Follow-up of medical conditions can be performed by means of, for example, physical examination and imaging techniques for identifying and measuring tumor burden, and/or monitoring cancer-specific biomarkers in blood to evaluate response to treatment, or recurrence. A series of sub-criteria can be associated to each of the three main evaluation criteria (i.e. boxes in the bottom of the flowchart), involving the evaluation of specific parameters in tumor tissue obtained via biopsy and/or in blood samples, including the modification in the expression of and/or response to cytokines (such as interferons or interleukins, individually or in specific combinations, see Example 4) or circulating/infiltrating immune cells. (B) Flowchart summarizing therapeutic opportunities that are available following (but possibly started even before in concurrently with) the administration of a BO-11X formulation such as BO-112, involving the readouts as defined in the previous flowchart and additional readouts (such as those coming from the analysis of gene expression, protein expression, mutational burden status, or T cell clonality in specific cells or tissues before and after BO-112 administration). This analysis provides BO-112-induced molecular signatures that may indicate continuation with the same or a different regimen of BO-11X treatment or a different type of medical follow-up, including the possibility to use treatments (e.g., radiotherapy, chemotherapy, anti-PD-1 or other immunomodulating therapy, cancer vaccination, cell-based therapies, etc.) against which the tumor in the patient was identified as being poorly responding, resistant or insensitive prior to the administration of a BO-11X formulation (i.e. boxes in the bottom of the flowchart).

Figure 16:
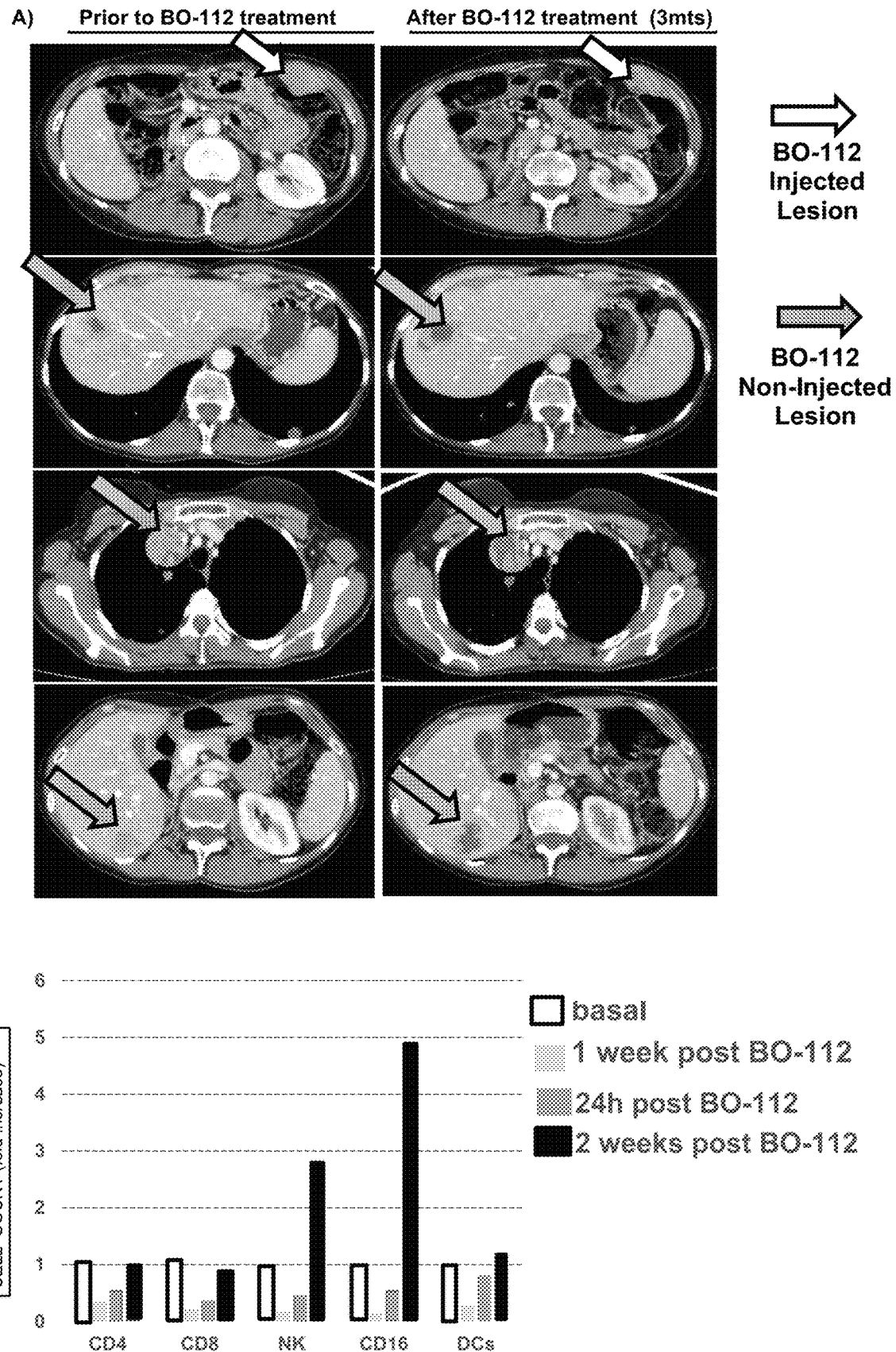

FIG. 16: Clinical data generated in metastatic lesions in a patient. A 46 years-old female with metastatic leiomyosarcoma developed progressive disease after receiving several lines of treatment (chemotherapy and anti PD-1/anti LAG-3 combination, in particular). She had an abdominal wall cancer lesion that was suitable for injection and with informed consent received intra-tumoral injections of BO-112. After three doses of 0.6 mg BO-112, the patient received no further systemic treatment, and only palliative radiation to a femoral (bone) metastasis. (A) Arrows indicate relevant lesions, showing increase in radiological signs of tumoral necrosis, as established in 4 different locations by imaging analysis (left column) that was repeated in similar positions 3 months later (right column), showing improvement in both BO-112 injected and non-injected lesions. (B) Before and after BO-112 treatment, populations of Circulating Immune cells (defined on the basis of specific or combined cell surface markers such as CD4, CD8, or CD8) were evaluated in peripheral blood of this patient, indicating that (after an initial reduction) BO-112 treatment may increase the amount of specific cell subpopulations in circulation, in particular NK cells and CD16-positive cells.

Figure 17:

FIG. 17: Clinical data generated in a 72 year-old female patient presenting metastatic melanoma (stage IV) with progressive disease. She previously underwent multiple surgeries including phalanx amputation and inguinal lymphadenectomies, as well as radiotherapy. Previous systemic treatment included interferon, after pembrolizumab and fotemustin treatments. She was evaluated with a lesion in the inguinal region measuring 9 cm which was suitable for intra-tumoral injection. With informed consent, the inguinal lesion was injected under ultrasound guidance with a single dose 0.6 mg BO-112 and followed by imaging analysis that was repeated in similar position in the following weeks. One week after this single dose administration, the target lesion had decreased in size to 8 cm. The patient then was treated with ipilimumab (anti-CTLA4 antibody, 3 mg/kg every 3 weeks for 4 cycles), resulting in a further improvement in cancer lesions.

DETAILED DESCRIPTION OF THE INVENTION

The present invention discloses compositions, including those defined in the composition claims of PCT/EP2016/078078, defined therein as BO-11X, and exemplified in Examples 1 and 2 thereof therein, wherein X is a whole number. A group of features of BO-11X composition disclosed in PCT/EP2016/078078 is comprised in a BO-112 composition. In particular, the BO-112 composition can be further defined by combining specific features that apply either to the particles that are comprised in the BO-112 composition or to the physical-chemical features that are associated to the aqueous composition.

A preferred BO-112 composition is an aqueous composition comprising particles wherein:
  (i) each of said particles comprises a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
  (ii) at least 90% of said particles has a mono-modal diameter distribution below 300 nm;
  (iii) said particles have a z-average diameter of less than or equal to 200 nm, as measured according to ISO 22412:2017;
  (iv) said composition contains polyinosinic-polycytidylic acid [poly(I:C)] at a concentration of at least 0.5 mg/mL;
  (v) said composition has: a pH of between 2 and 4; and
  (vi) said composition has a zeta potential between 35 mV and 50 mV, according to ISO 13099.

In a preferred embodiment, a BO-112 composition is a composition according to the foregoing, wherein at least 90% of said particles have a mono-modal diameter distribution between 30 nm and 150 nm.

In a more preferred embodiment, a BO-112 composition is a composition according to the foregoing, wherein at least 40% of the double-stranded polyribonucleotides comprised in said particles have at least 850 base pairs, and at least 50% of the double-stranded polyribonucleotides comprised in said particles have between 400 and 5000 base pairs.

In an even more preferred embodiment, a BO-112 composition is a composition according to the foregoing, wherein said composition has a zeta potential comprised between 38 and 45 mV.

In a still more preferred embodiment, a BO-112 composition is a composition according to the foregoing, wherein said linear polyalkyleneimine is a water-soluble, linear homo-polyalkyleneimine or hetero-polyalkyleneimine.

In an even still more preferred embodiment, a BO-112 composition is a composition according to the foregoing, wherein said linear polyalkyleneimine is a linear polyethyleneimine.

In a yet more preferred embodiment, a BO-112 composition is a composition according to the foregoing, wherein the polydispersity index of said particle diameter is inferior to 1.5.

In a furthermore preferred embodiment of the foregoing, a BO-112 composition is a composition according to the foregoing, wherein polyinosinic-polycytidylic acid [poly(I:C)] contains between 5% and 60% of double-stranded polyribonucleotides having less than 400 base pairs, between 15% and 30% of double-stranded polyribonucleotides having between 400 and 850 base, between 10% and 70% of double-stranded polyribonucleotides having between 850 and 5000 base pairs, and between 0% and 10% of double-stranded polyribonucleotides having more than 5000 base pairs.

In a furthermore more preferred embodiment, a BO-112 composition is a composition according to the foregoing, wherein said composition further comprises at least one pharmaceutically acceptable carrier, organic solvent, excipient and/or adjuvant.

In a furthermore still more preferred embodiment, a BO-112 composition is a composition according to the foregoing, wherein said composition further comprises at least one compound selected from an organic compound, an inorganic compound, a nucleic acid, an aptamer, a peptide or a protein.

In a furthermore even more preferred embodiment, a BO-112 composition is a composition according to the foregoing, wherein said composition further comprises glucose or mannitol in a concentration of between 1 and 10% (weight/volume).

In a furthermore even still more preferred embodiment, a BO-112 composition is a composition according to the foregoing, wherein said composition is an aqueous composition that has an osmolality of between 200 and 600 mOsm/kg.

In a furthermore much more preferred embodiment, a BO-112 composition is a composition according to the foregoing, wherein:
  (i) each of said particles is formed by making a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
  (ii) at least 90% of said particles has a mono-modal diameter distribution below 300 nm;
  (iii) said particles have a z-average diameter of less than or equal to 200 nm, as measured according to ISO 22412:2017;

(iv) said composition contains polyinosinic-polycytidylic acid [poly(I:C)] at a concentration of at least 0.5 mg/mL;
(v) said composition has: a pH of between 2 and 4; and
(vi) said composition has a zeta potential equal or superior to 30 mV, according to ISO 13099;
wherein said particles are formed at the ratio of the number of moles of nitrogen of said polyalkyleneimine to the number of moles of phosphorus of said double-stranded polyribonucleotide in said composition being equal to or greater than 2.5.

In a preferred embodiment of the furthermore much more preferred embodiment, a BO-112 composition is a composition according to the foregoing, wherein said polyinosinic-polycytidylic acid [poly(I:C)] are formed by annealing:
(i) polyinosinic acid [poly(I)] preparation containing between 80% and 99% of molecules having less than 400 bases, between 0% and 20% of molecules having between 400 and 850 bases, between 0% and 5% of molecules having between 850 and 5000 bases, and between 0% and 5% of molecules having more than 5000 bases; and
(ii) polycytidylic acid [poly(C)] preparation containing between 20% and 85% of molecules having less than 400 bases, between 10% and 40% of molecules having between 400 and 850 bases, between 0% and 50% of molecules having between 850 and 5000 bases, and between 0% and 5% of molecules having more than 5000 bases.

In a more preferred embodiment of the furthermore much more preferred embodiment and preferred embodiment thereof, a BO-112 composition is a composition according to the foregoing, wherein said composition is formed by additionally adding glucose or mannitol in a concentration of between 1 and 10% (weight/total volume of said composition).

In a more preferred embodiment of the foregoing, said polyinosinic-polycytidylic acid [poly(I:C)] are formed by annealing:
(i) polycytidylic acid [poly(C)] preparation containing between 20 and 82% of molecules having less than 400 bases, between 15 and 40% having 400-850 bases, between 3 and 50% having 850-5000 bases, and less than 1% of molecules having more than 5000 bases; and
(ii) polyinosinic acid [poly(I)] preparation containing between 80 and 99% of molecules having less than 400 bases, between 1 and 20% of molecules having 400-850 bases, between 0 and 5% of molecules having 850-5000 bases, and less than 1% of molecules having more than 5000 bases.

More preferably polyinosinic-polycytidylic acid [poly(I:C)] are formed by annealing:
(i) polycytidylic acid [poly(C)] preparation containing between 33% and 73% of molecules having less than 400 bases, between 20 and 37% of molecules having 400-850 bases, between 5 and 48% of molecules having 850-5000 bases, and less than 1% of molecules having more than 5000 bases; and
(ii) polyinosinic acid [poly(I)] preparation containing between 81 and 98% of molecules having less than 400 bases, between 6 and 17% of molecules having 400-850 bases, between 0 and 3% of molecules having 850-5000 bases, and less than 1% of molecules having more than 5000 bases.

In an even more preferred embodiment of the foregoing, the BO-11X and BO-112 compositions comprise poly(I:C) molecules having a size distribution whereby said poly(I:C) contains between 7 and 57% of molecules having less than 400 bases, between 20 and 45% of molecules having 400-850 bases, between 20 and 70% of molecules having 850-5000 bases, and between 0 and 9% of molecules having more than 5000 bases. More preferably, the BO-11X and BO-112 compositions comprise poly(I:C) molecules having a size distribution whereby said poly(I:C) contains between 10 and 30% of molecules having less than 400 bases, between 20 and 30% of molecules having 400-850 bases, between 40 and 60% of molecules having 850-5000 bases, and between 0 and 5% of molecules having more than 5000 bases. Even more preferably, the BO-11X and BO-112 compositions comprise poly(I:C) molecules having a size distribution whereby said poly(I:C) contains between 11 and 28% of molecules having less than 400 bases, between 23 and 27% of molecules having 400-850 bases, between 42 and 55% of molecules having 850-5000 bases, and between 0 and 3% of molecules having more than 5000 bases.

A BO-112 composition is also a composition obtainable by lyophilisation of the aqueous composition according to any of the foregoing embodiments. These lyophilised BO-112 compositions may be then reconstituted using appropriate solutions to provide formulations that present one or more of features defined above, in particular composition comprising particles wherein:
(i) each of said particles comprises a complex of at least one double-stranded polyribonucleotide, or a salt or solvate thereof, and at least one polyalkyleneimine, or a salt and/or solvate thereof;
(ii) at least 95%, or at least 90%, of said particles has a diameter of less than or equal to 900 nm, preferably, less than or equal to 500 nm (for example, between 140 and 400 nm or between 140 and 250 nm); and
(iii) said particles have a z-average diameter of less than or equal to 300 nm, preferably less or equal to 200 nm, more preferably less than or equal to 150 nm, in particular, as measured according to ISO 22412:2017.

Furthermore, the present invention also relates to a formulation obtainable by treating a cell or tissue from a subject ex vivo with a BO-11x composition, preferably a BO-112 composition, as defined herein. Preferably, said formulation comprises a cell or tissue from a subject which has been treated ex vivo with a composition as disclosed herein. More preferably, said cell or tissue is a cell or tissue in a sample from a subject, such as a blood sample, lymph sample or tissue biopsy. The present invention also provides means for generating an aqueous solution of poly(I:C) molecules (already containing or not an excipient such as glucose or mannitol) and have appropriate features for being mixed with aqueous solution of a polyalkyleneimine (such as polyethyleneimine) for producing the BO-11X formulations. The poly(I:C)-containing formulation resulting from mixing these two aqueous solutions is then maintained as a batch preparation (preferably still as an aqueous solution or in a lyophilized form) or can be directly prepared in aliquots, each contained in a single-use vials, syringes, or other appropriate container for storage, single use of such aliquots, and/or lyophilisation. BO-11X formulations (in a liquid or lyophilized form) can be stored at room temperature, at a temperature comprised between 8° C. and 2° C., or at a temperature below 0° C. or below −20° C.

In such preferred embodiment, further compounds (such as one or more antibody, hormone, peptide, excipient, carrier, inhibitor of an enzymatic activity, chemotherapeutic agent, antibiotic, stabilizing agent, labelling agent, organic solvent, preservatives, carriers, or other drug) can be either added in each of the two aqueous solutions (if not altering the correct formation of the particles or any other of the features listed above for BO-11X formulations) prior to their mixing or after that BO-11X formulation has been produced by mixing the two aqueous solutions (of double-stranded polyribonucleotide and polyalkyleneimine). Such additional components that are consequently administered at the same time with BO-11X components can provide a composition with improvements in the bioavailability, efficacy, pharmacokinetic/pharmacodynamic profiles, stability, metabolization, or other property of pharmaceutical interest that are not observed when each of initial BO-11X formulation or the additional component (another compound of pharmaceutical interest, for instance) is administered alone, or each of initial BO-11X formulation or the additional component are administered separately.

In a further preferred embodiment, the BO-11X formulation is for use as a medicament, such as a pharmaceutical composition that is formulated (e.g. as an injectable, aqueous composition, optionally comprising a pharmaceutically acceptable carrier, excipient and/or adjuvant) and administered for the delivery of double-stranded polyribonucleotides to an organ or a tissue in a healthy state, presenting a disease related to a exogenous pathogenic agent (such a bacteria or a virus), or presenting an alteration due to a cell growth disorder characterized by abnormal growth of human or animal cells for instance, due to cancer (that is, involving tumorogenic transformation, metastasis, toxic compound), or a gynaecological disorder characterized by abnormal growth of cells of the female mammal reproductive organs). Thus, in a preferred embodiment, the present invention relates to a method of treatment of a disease comprising administering the composition of the present invention to a human or animal. In a further preferred embodiment, the present invention relates to a method of treatment of a cell growth disorder characterized by abnormal growth of human or animal cells, as defined herein, comprising administering the composition of the present invention to a human or animal.

Preferably, the BO-11X formulation is used in methods for inducing (directly or indirectly) the death of the tumor cell or suppress growth of the tumor cell, at scope of treating, reducing, ameliorating, or preventing cancer growth, survival, metastasis, epithelial-mesenchymal transition, immunologic escape or recurrence. More preferably, BO-11X formulations are used in methods for treating solid tumors, such as carcinomas, gliomas, melanomas, or sarcomas. In particular, the BO-11X formulation is administered either systemically or more directly within or in a location near to the tumor such as at the margin of the tumor mass, in the surrounding epithelial cells, lymphatic or blood vessels (e.g. by intratumoral or peritumoral injection), or the abnormally growing cells of female mammal reproductive organs. A further preferred embodiment of the present invention relates to a BO-112 composition as defined in the foregoing, for use as a medicament. A further preferred embodiment of the present invention relates to a BO-112 composition for use, as defined in the foregoing, wherein said medicament is an injectable, aqueous composition, optionally comprising a pharmaceutically acceptable carrier, excipient and/or adjuvant.

Another embodiment of the present invention relates to a BO-112 composition, as defined in the foregoing, for use in treatment of a cell growth disorder characterized by abnormal growth of human or animal cells. A preferred embodiment relates to the BO-112 composition for use according to the foregoing, wherein said cell growth disorder is cancer or a gynaecological disorder characterized by abnormal growth of cells of the female mammal reproductive organs. A more preferred embodiment of the aforementioned embodiment relates to the BO-112 composition for use according to the foregoing, wherein the composition is for use for intratumoral or peritumoral injection. Alternatively, a more preferred embodiment of the aforementioned embodiment and preferred embodiment thereof relates to the BO-112 composition for use according to the foregoing, wherein the composition is for use for injection at the level of skin or of an internal organ or tissue.

Another embodiment of the present invention relates to a BO-11X composition, preferably a BO-112 composition, for use as a vaccine, as defined in the foregoing. Analogously, the present invention also relates to a method of treatment in a subject (patient) of a disease using said vaccine. Preferably said BO-11X or BO-112 composition is for use as a vaccine in treatment of a cell growth disorder characterized by abnormal growth of human or animal cells, more preferably in treatment of cancer. Alternatively, said BO-11X or BO-112 composition is for use as an infection-related vaccine.

In some embodiments, the BO-11X formulation is produced according to the manufacturing methods, and then defined structurally and functionally, as described in the Examples as BO-112 formulations. The BO-11X formulation can further exhibit the biological activities that were characterized for BO-110 as described in WO2011003883, namely activation of a family helicase MDA-5 or the level of NOXA expression, in combination with the induction of autophagy in cancer cells or in a cell line derived from cancer cells, preferably from a human origin, albeit to an improved degree. Independently from the process for characterizing the properties and mechanism of action for BO-110 that is described in WO2011003883, examples of cell lines for validating BO-11X formulations are human SK-Mel-19, SK-Mel-28, SK-Mel-103 and SK-Mel-147 cells, and the murine B16 cells, said melanoma cell lines presenting an increased expression of molecules such as Interferon Beta when exposed to a BO-11X formulation. Additionally, the BO-11X formulation presents no toxicity at the doses that promote tumor cell death in cancer cells lines against normal cells that are used as controls, such as melanocytes or other skin cells, as well as cells of the immune system, which usually represent sites of secondary toxicity in cancer treatment. The BO-11X formulation may also, following the autophagy and apoptosis of cancer cells (or any other effect of therapeutic interest that this formulation may induce in such cells), induce the release of cancer cell antigens that may act as inducers of a tumor-specific immunological response, in particular when BO-11X formulation is administered locally to cancerous cells or tumors (e.g. by peritumoral or intratumoral injection, administering BO-11X at the margin of tumor mass, in surrounding epithelial cells, lymphatic or blood vessels, or directly within the tumor mass), with or without the simultaneous or sequential administration of another drug or other treatment for same indication.

The BO-11X formulation may, following the administration in location distant or independent from tumor mass (for example, by intra-muscular or sub-cutaneous injection, or in by ex vivo administration to cells obtained from the patient and then re-injected) provide effect of therapeutic interest upon targeting also cells other than cancer cells (including immune cells or other cells in blood circulation or located nearby the cancer). Such an effect may be due to the induction of the release of a tumor-specific effector, or the migration of cells towards cancer cells or within tumors, even when peritumoral or intratumoral injection is not possible (such as in non-solid tumors such as leukemia or other haematological cancer).

The present invention also relates to a process to manufacture the composition, as disclosed herein, which comprises:
(i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
(ii) independently filtering each solution through a filter having a pore diameter of less than or equal to 500 nm to form sterilized solutions;
(iii) mixing the resulting sterilized solutions in a mixing chamber to form an aqueous composition by addition of one of said solutions into the other solution in said mixing chamber, optionally by injection, at a rate of greater than or equal to 1 mL/min, or by simultaneous addition of each of said solutions into said mixing chamber, optionally by injection, at a rate of greater than or equal to 1 mL/min; and optionally
(iv) filtering the resulting aqueous composition through a filter having a pore diameter of less than or equal to 600 nm to form a filtrate, or centrifuging the resulting aqueous composition at greater than or equal to 22480 m/s$^2$ to form a supernatant; and, optionally
(v) lyophilising the resulting aqueous composition, filtrate or supernatant.

Thus, in one preferred embodiment, the present invention may relate to a process to manufacture the composition, as disclosed herein, which comprises:
(i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
(ii) independently filtering each solution through a filter having a pore diameter of less than or equal to 500 nm to form sterilized solutions; and
(iii) mixing the resulting sterilized solutions in a mixing chamber to form an aqueous composition by addition of one of said solutions into the other solution in said mixing chamber, optionally by injection, at a rate of greater than or equal to 1 mL/min, or by simultaneous addition of each of said solutions into said mixing chamber, optionally by injection, at a rate of greater than or equal to 1 mL/min; and
(iv) optionally lyophilising the resulting aqueous composition.

In addition, in another preferred embodiment, the present invention may relate to a process to manufacture the composition, as disclosed herein, which comprises:
(i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
(ii) independently filtering each solution through a filter having a pore diameter of less than or equal to 500 nm to form sterilized solutions;
(iii) mixing the resulting sterilized solutions in a mixing chamber to form an aqueous composition by addition of one of said solutions into the other solution in said mixing chamber, optionally by injection, at a rate of greater than or equal to 1 mL/min, or by simultaneous addition of each of said solutions into said mixing chamber, optionally by injection, at a rate of greater than or equal to 1 mL/min; and
(iv) filtering the resulting aqueous composition through a filter having a pore diameter of less than or equal to 600 nm to form a filtrate, or centrifuging the resulting aqueous composition at greater than or equal to 22480 m/s$^2$ to form a supernatant; and
(v) optionally lyophilising the resulting filtrate or supernatant.

More preferably, the process of the present invention does not comprise a final step of lyophilisation. In the process (or method) of the present invention, said double-stranded polyribonucleotide, said polyalkyleneimine and said pharmaceutically acceptable carrier, organic solvent, excipient and/or adjuvant are as disclosed herein. Sterilizing each solution to form sterilized solutions takes place by independently filtering said solutions through a filter having a pore diameter of less than or equal to 500 nm, preferably by independently filtering said solutions through a filter having a pore diameter of less than or equal to 300 nm, more preferably by filtering said solutions through a filter having a pore diameter of less than or equal to 200 nm. Preferably the mixing of the resulting filtrates takes place through the large-scale convective transport of eddies and subsequently through elimination of concentration differences through purely diffusive transport. The mixing chamber may be any chamber or vessel in which the mixing of said solutions begins, such as a flask, reactor or mixer, and having any appropriate shape (such as cylindrical, spherical, or other shape that allows the correct mixing within the chamber) in which the mixing is performed in a controlled manner within a confined space. More preferably, said mixing chamber has a fixed volume of between 0.1 and 20 mL (or even bigger volumes such as 25, 50, 100 mL or more, allowing the continuous, higher yield of product, especially in GMP conditions), furthermore preferably between 0.2 and 10 mL, much more preferably between 0.5 and 8 mL. More preferably, mixing takes place by addition, optionally by injection, at a rate of between 1 mL/min and 2000 mL/min, still more preferably at between 10 and 1000 mL/min, furthermore preferably at between 20 and 500 mL/min. Optional filtering of the resulting aqueous composition to form or collect a filtrate may subsequently be performed through a filter having a pore diameter of less than or equal to 600 nm, preferably not exceeding the diameter of 500 nm, more preferably not exceeding the diameter of 400 nm, yet more preferably not exceeding the diameter of 300 nm. Alternatively, optional centrifuging of the resulting aqueous composition to form or collect a supernatant may subsequently be performed at greater than 22480 m/s$^2$ (5000 rpm on a rotor having a radius of 0.082 m), preferably at greater than 27202 m/s$^2$ (5500 rpm on a rotor having a radius of 0.082 m), more preferably at greater than 32372 m/s$^2$ (6000 rpm on a rotor having a radius of 0.082 m), yet more preferably 44062 m/s$^2$ (7000 rpm on a rotor having a radius of 0.082 m). In one especially preferred embodiment step (iv) is obligatory when the composition of the present invention is not achieved by steps (i) to (iii) of the process of the present invention, namely when addition is carried out at such that a rate that less than 95% of the particles comprised in said aqueous composition has a diameter of less than or equal to 600 nm; and/or said particles have a z-average diameter of greater than 200 nm, more preferably when said particles do not have a mono-modal diameter distribution. This may be the case when addition is performed at a rate of between 1 mL/min and 20 mL/min, particularly in a mixing (reaction) chamber of between 0.5 and 20 mL. Finally, the resulting aqueous composition, filtrate or supernatant may be subjected to lyophilisation to afford the composition of the present invention as a particulate solid.

Thus, in one much more especially preferred embodiment of the process of the present invention, said process comprises
 (i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
 (ii) independently filtering each solution through a filter having a pore diameter of less than or equal to 200 nm to form sterilized solutions;
 (iii) mixing the resulting sterilized solutions in a mixing chamber to form an aqueous composition by addition of one of said solutions into the other solution in said mixing chamber, optionally by injection, at a rate between 20 mL/min and 100 mL/min, or by simultaneous addition of each of said solutions into said mixing chamber, optionally by injection, at a rate between 20 mL/min and 100 mL/min, wherein said mixing chamber has a volume of between 0.2 and 10 mL;
 (iv) filtering the resulting aqueous composition through a filter having a pore diameter of less than or equal to 500 nm to form a filtrate, or centrifuging the resulting aqueous composition at greater than or equal to 32372 m/s$^2$ (6000 rpm on a rotor having a radius of 0.082 m) to form a supernatant; and
 (v) optionally lyophilising the resulting filtrate or supernatant.

In another even much more especially preferred embodiment of the process of the present invention, said process comprises
 (i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
 (ii) independently filtering each solution through a filter having a pore diameter of less than or equal to 200 nm to form sterilized solutions;
 (iii) mixing the resulting sterilized solutions in a mixing chamber to form an aqueous composition by addition of one of said solutions into the other solution in said mixing chamber, optionally by injection, at a rate between 30 mL/min and 100 mL/min, or by simultaneous addition of each of said solutions into said mixing chamber, optionally by injection, at a rate between 30 mL/min and 100 mL/min, wherein said mixing chamber has a volume of between 0.5 and 8 mL; and
 (iv) optionally lyophilising the resulting aqueous composition.

In a further embodiment, the BO-11X formulation is produced according to a manufacturing process that involves the mixing of two aqueous solutions, a first one comprising the double-stranded polyribonucleotides (or a salt or solvate thereof) and a second one comprising the polyalkyleneimine (or a salt or solvate thereof) so that the resulting particles present the features defined above, in particular with respect to the diameter and the mono-modal diameter distribution as well the appearance as an essentially clear colloidal solution.

In a further optional step, an additional compound (being an immune-related adjuvant or therapeutic compound, such as CD40L, IL12, viral or tumor antigens, or anti-cancer drug) can be added during step (i), or after of any of the steps (i)-(v) or the steps (i)-(iv) in the process to manufacture the composition defined above. The resulting compositions (that can be named as BO-11Xm and more specifically as BO-112m, when presenting the combination of features as described above) can be used in accordance to any of the embodiments that are herein disclosed for using BO-11X compositions, and specifically BO-112 compositions.

As described in further details in the Examples, the BO-11X formulations can be provided by filtering and/or centrifuging pharmaceutical composition comprising particles formed by double-stranded polyribonucleotides and a water-soluble, polycationic homo- or hetero-polymer, providing the BO-11X formulations as bulk or single use liquid compositions without visible aggregates. Such a process to manufacture the composition comprises:
 (i) preparing an aqueous solution of at least one double-stranded polyribonucleotide, or a salt or solvate thereof, and an aqueous solution of at least one polyalkyleneimine, or a salt or solvate thereof, optionally together with a pharmaceutically acceptable carrier, organic solvent, excipient and/or adjuvant present in either solution;
 (ii) mixing said solutions; and
 (iii) filtering the resulting mixture through a filter having a pore diameter of less than or equal to 600 nm, or centrifuging at greater than 22480 m/s$^2$.

This process can be further adapted for the actual components of the composition (double-stranded polyribonucleotides, the polyalkyleneimine, and optional further components) as well as the desired methods of using, storing, shipping, packaging, and/or administering the composition, in particular if the composition requires to be manufactured immediately prior to the use or, as is more common for pharmaceutical compositions, manufactured for long-term storage and/or in the form of multiple containers each one for a single-use (e.g. in sterile vials or syringes), and containing particles having the most uniform size, poly(I:C) content, stability, solubility, and, finally, biological effects when administered.

The mixing and filtering steps (ii) and (iii) above can be adapted at the level of order of filtering and/or mixing, method of mixing, the mixing speed, and/or the amount of solutions that is mixed. in a further preferred embodiment, the process to manufacture BO-11X formulations comprises:
 (i) preparing an aqueous solution of at least one double-stranded polyribonucleotide, or a salt or solvate thereof, and an aqueous solution of at least one polyalkyleneimine, or a salt or solvate thereof, optionally together with a pharmaceutically acceptable carrier, organic solvent, excipient and/or adjuvant present in either solution;

(ii) sterilizing each solution by filtering them independently;

(iii) mixing said solutions in the container for storing, lyophilising, and/or using the composition by adding either solution first and then adding the other solution at an injection speed superior to 50 rpm at a flow speed between 1 mL/min and 50 mL/min; and (iv) sealing the container.

In a further optional step, another compound (being an immune-related adjuvant or therapeutic compound, such as CD40L, IL12, viral or tumor antigens, or being an adjuvant or therapeutic compound, such an anti-cancer drug) can be added during step (i), or after of any of the steps (i)-(v) or the steps (i)-(iv) in the process to manufacture the composition defined above. The resulting compositions (that can be named as BO-11Xm and more specifically as BO-112m, when presenting the combination of features (i)-(vi) as described above) can be used in accordance to any of the embodiments that are herein disclosed for using BO-11X compositions, and specifically BO-112 compositions.

Depending on how the aqueous composition of the present invention is to be administered (e.g. by sub-cutaneous or intratumoral injection), the BO-11X composition or BO-112, as defined in the foregoing, can be provided in containers and/or in amount that are the most appropriate for single use or multiple dose.

Combinations

A composition according to the present invention can be used in combinations including other compounds or treatments with which it is known to be compatible, if not providing an additive or even synergistic effect. Moreover, the compositions that are be named as BO-11Xm (and specifically as BO-112m) can be produced as described above providing new products in which the combination of a BO-11X composition, such as a BO-112 compositions, with another compound provides improved therapeutic effects or other pharmaceutically relevant effects (including stability or efficacy at lower doses, in general or with respect to specific indications or routes of administration) when compared to combinations wherein the BO-11X composition and the other compound are simply mixed before use.

For instance, poly(I:C) molecules can be used in combination with different anti-cancer drugs, antibodies, radiotherapy, or chemotherapy (Le U et al., 2008; Le U et al., 2009; Taura M et al., 2010; Matijević T et al., 2011; Levitzki A, 2012; Yoshino H and Kashiwakura I, 2013; Hafner A et al., 2013) or different length of poly(I:C) molecules (Zhou Y et al., 2013). Poly(I:C) molecules have also been used as an adjuvant or synergistiically-acting agent when combined with other agents such as in vaccination with cancer antigens or cell lysates (Ammi R et al., 2015), agents blocking PD-1/PD-L1 pathway (Nagato T and Celis E, 2014), other TLR agonists, such as TLR9 agonist CpG ODN (Zhang Y et al., 2014), dichloroacetate (Ohashi T et al., 2013), IL27 (Chiba Y et al., 2013), kinase inihibitors such as sorafenib (Ho V et al., 2015), proapoptotic proteins such as NS1 (Gupta S et al. 2016), Zoledronic acid (Chen L et al., 2013), or all-trans retinoic acid (Szabo A et al., 2012). Other uses of BO-11X formulations may become apparent in view of activities of poly(I:C) molecules towards specific cell types recently demonstrated, at least using in vitro assays, such as on pre-adipocytes, inhibiting differentiation and differentiation in adipocytes (Yu L et al., 2016), mesenchymal stem cells, enhancing immunosuppressive effects (Cho K. et al., 2016; Vega-Letter A et al., 2016), or activation of NK cells (Perrot I et al., 2010).

In some aspects, the present invention relates to a pharmaceutical composition comprising an effective amount of a BO-11X formulation and an effective amount of one or more immune-modulating agents, in particular agents that target immune checkpoint molecules (such as PD-1, PD-L1, PD-L2, CTLA-4, CD134, CD134L, CD137, CD137L, CD80, CD86, B7-H3, B7-H4, B7RP1, LAGS, ICOS, TIM3, GAL9, CD28, AP2M1, SHP-2, PPP2R5A or OX-40), said compounds commonly named as checkpoint inhibitors (CPIs). Alternatively the immune-modulating agent blocks the immunosuppressive effect of T regulatory cells such as an inhibitor of drug targets such IDO, TGF-$\beta$, STAT3, or CSFR1.

Accordingly, the present invention provides compositions and methods that are useful in combination therapies and regimens comprising the administration of BO-11X formulations (or BO-11Xm formulations) and another therapeutic agent or treatment (including radiotherapy, chemotherapy, cryotherapy, tumor ablation, or photodynamic therapy). In particular, the present invention relates to a method for treating, ameliorating, or preventing cancer growth, metastasis, ulceration, immunologic escape or recurrence in a subject, comprising administering a BO-11X formulation and one or more anticancer drug, preferably an immune-modulating agent, wherein the administration is simultaneous (as separate formulations or in the context of a co-formulation) or sequential (in any order or in consecutive cycles of administration). In some aspects, the present invention relates to a method for treating cancer, comprising administering an effective amount of BO-11X formulation agent and an effective amount of one or more immune-modulating agents to a subject in need thereof, in particular wherein the subject is undergoing cancer therapy with one or more immune-modulating agents.

In some embodiments, the immune-modulating agent is preferably an antibody including a monoclonal antibody and other antibody formats, or any other pharmaceutically available agent that binds a cell surface protein that control immune response, thus acting as a CPI, which can block, reduce and/or inhibit PD-1 and PD-L1 or PD-L2 and/or the binding of PD-1 with PD-L1 or PD-L2. Alternatively, this CPI can block, reduce and/or inhibit reduces and/or inhibits the activity of other immune checkpoint molecules such as CTLA-4, AP2M1, CD80, CD86, SHP-2, and/or PPP2R5A As a further alternative, the CPI increases and/or stimulates CD137 (4-1BB) and/or the binding of CD137 (4-1BB) with one or more of 4-1BB ligand and TRAF2.

In some embodiments, the methods involving combination therapies and regimens for the treatment of cancer comprising the administration of BO-11X formulations (or BO-11Xm formulations) may further defined with respect to a specific administration method, wherein the BO-11X formulation is administered by a route different form the one of the other therapeutic compound, such as an immune-modulating agent, and preferably a CPI. This method may involve administering the BO-11X formulation by intratumoral or peritumoral injection (within the tumor, at the margin of the tumor mass, in the surrounding epithelial cells, lymphatic or blood vessels) or other means that allow administering the BO-11X formulation directly within or in proximity of cancer cells or organ comprising the cancer cells (and not indirectly, for instance through bloodstream) and the systemic administration of CPI or other immunostimulatory agent). The BO-11X formulation by intratumoral or peritumoral injection may be performed at the level of skin, i.e. into the skin (e.g. for treating melanoma or in connection to the combination with a vaccine) or of an internal organ or tissue, i.e. into said internal organ or tissue (e.g. by intra-hepatic injection for treating liver cancer or intravesicular administration for bladder cancer). Such local administration of BO-11X formulation preferably follows or (preferably) is followed by the administration of the immunostimulatory agent.

The BO-11X formulation (or a BO-11Xm formulation) can be also administered in combination to cell-based therapies, wherein the BO-11X is either co-administered with the cell-based therapy directly to the patient, or is used for treating cells that are obtained from a patient (from the blood or from a biopsy including cells twithin the tumor mass, at the margin of tumor mass, in surrounding epithelial cells, lymphatic or blood vessels). These cells, with or without positive or negative selection for specific cell types, can be exposed to BO-11X formulation in an appropriate laboratory setting for generating cells that, following this treatment, present markers, secrete proteins and/or expose antigens useful for further cancer treatment. Such autologous cells, again with or without further negative or positive selection, can be administered to the patient. During later phases of the treatment, BO-11X formulation can be further administered to the patient by any appropriate mean (by intratumoral or, preferably, intra-muscular or sub-cutaneous injection). The ex vivo treatment of cells from patients can be performed for a period of time of greater than 1 hour, preferably greater than 3 hrs, more preferably greater than 8 hrs, even more preferably greater than 24 hrs, or more, at a concentration that lower to the one intra-muscular or sub-cutaneous injection (preferably at 50%, more preferably at 25%, even more preferably at 10%, furthermore preferably at 5% or much more preferably at 1% of such dose).

Additional Effects and Uses

In a further embodiment, the present invention provides pharmaceutical uses and methods involving the administration of a BO-11X formulation (or a BO-11Xm formulation) for increasing immune response against a pathogen or undesirable biological agent and in particular for enhancing an anti-tumor immune response, potentially acting itself as an immune-modulating agent. Such an effect can be monitored by measuring tumor-related immune response into the tumor site and tumor microenvironment (or in the bloodstream, other biological fluids, and tissues) at the level of relevant cell types or subpopulations (e.g. dendritic cells, T regulatory cells, T cells and/or NK cells) and/or of immunological biomarkers (e.g. chemokines, growth factors, cytokines, and their receptors).

In particular, when the BO-11X formulation (or a BO-11Xm formulation) is clinically administered by intratumoral injection, apoptosis and/or necrosis is observed in the tumor, thus potentially promoting the presentation of tumor antigens to resident dendritic cells. A signaling cascade may lead also to the recruitment of immune cells, in particular CD4+ and CD8+ T cells into the tumor mass promoting an immune effect against the tumor, contributing to the cytotoxic effect of BO-11X. Another embodiment relates to a method for inducing interferon production in a cell or tissue in vitro, comprising the step of contacting a cell or tissue with a composition, wherein said cell or tissue exhibits a cell growth disorder characterized by abnormal growth of human or animal cells, wherein said composition is BO-11X, more preferably BO-112. Thus, the invention relates to a method for inducing interferon production in cells from a subject in vitro, comprising:
 (i) obtaining the cells from the subject;
 (ii) contacting said cells with a composition of BO11X, preferably BO-112.

Pharmaceutical Compositions

Also provided are methods for making a pharmaceutical composition of BO-112 (and/or other BO-11X formulations, such as a BO-11Xm or BO-112m formulation) by mixing a BO-11X formulation and one or more pharmaceutically acceptable adjuvant, diluent, carrier, or excipient thereof. Such components can be adapted for the specific medical indication (e.g. a solid cancer or a haematological cancer) and/or the administration means e.g. by injection (peri-tumoral, intra-tumoral, intra-hepatic, intra-pancreatic, intra-muscular, or sub-cutaneous injection), by inhalation, topically, or orally.

BO-11X formulation-based combination treatments may involve the same or different administration routes for BO-11X formulation and the other compound. In particular, the BO-11X formulation can be administered, as for other immunostimulatory RNA agents, by intratumoral or peritumoral injections that may activate the immune system prior to the systemic administration of a therapeutic antibody acting as CPI such a PD-1/PD-L1 pathway inhibitors (Bald T et al., 2014) or activated T cells (Amos S M et al., 2011). Alternatively, the BO-11X formulation together with other therapeutic compounds being TLR agonist or ligands such as CpG molecules or Resiquimod for enhancing the effect of anticancer vaccination (Sajadian A et al., 2014) or dendritic cells (Fujimura T et al., 2006).

Immune-Modulating Agents

The BO-11X formulation (including a BO-11Xm formulation) may be combined with one or more immune-modulating agents. In some embodiments, the immune-modulating agent is a co-stimulatory or co-inhibitory molecule (e.g. of one or more immune cells, such as, by way of non-limitation, T cells and NK cells). In some embodiments, the immune-modulating agent is an agent that modulates a CD4 and/or CD8 T cell, for instance by acting as agonist or antagonist with respect to CD3, CD4, CD8, PD-1, PD-L1, PD-L2, CTLA-4, CD137, CD96, CD73, CD90, CD47, CD69, CD26, TIM3, and LAG3. In other embodiments, the immune-modulating agent is an agent that modulates NK cells, for instance by acting as agonist or antagonist with respect to CD3, NKp46, CD16, NKG2D, NKp44, and NKp30. In other embodiments, the immune-modulating agent is an agent that modulates tumor stroma and endothelium biomarkers, for instance by acting as agonist or antagonist with respect to CD45, PD-L1, PD-L2, PTEN, and CD31, or combinations thereof. Combination of immune-modulating agents may be used to target different immune populations, whereby the combined agents target cells expressing different immune cell populations.

The immune-modulating agent is provided as a further compound in form of a chemical organic or inorganic compound, a nucleic acid, an aptamer, a peptide, a protein, and more particularly an antibody that binds the relevant target in the biological fluids or on cell surface. The antibody may be polyclonal or monoclonal; intact or truncated (e.g., F(ab')$_2$, Fab, Fv); bispecific or multispecific; xenogeneic, allogeneic, syngeneic, or modified forms thereof (e.g., a chimeric antibody or a humanized antibody). When the immune-modulating agent is a monoclonal antibody, it may be a non-human mammal-derived monoclonal antibody, a recombinant chimeric monoclonal antibody, a recombinant humanized monoclonal antibody, or a human monoclonal antibody.

The antibody that acts as immune-modulating agent can further comprise the structural elements normally required for exerting the required biological activity, such as four polypeptide chains, two heavy (H) chains and two light (L)

chains inter-connected by disulphide bonds that are capable of binding one or more antigens (e.g. bi-specific or multi-specific antibodies) and presenting an Fc region of an immunoglobulin (e.g. IgA, IgG, IgE, IgD or IgM) which may interact with Fc receptors and activate an immune response leading to depletion and/or cell death of immune cells or other cells. Each heavy chain is comprised of a heavy chain variable region ($V_H$) and a heavy chain constant region. The heavy chain constant region is comprised of three domains, $CH_1$, $CH_2$ and $CH_3$. Each light chain is comprised of a light chain variable region ($V_L$) and a light chain constant region. The light chain constant region is comprised of one domain, CL. The $V_H$ and $V_L$ regions can be further subdivided into regions of hypervariability, termed complementarity determining regions (CDRs), interspersed with regions that are more conserved, termed framework regions (FR). Each variable region ($V_H$ or $V_L$) contains 3 CDRs, designated CDR1, CDR2 and CDR3. Each variable region also contains 4 framework sub-regions, designated FR1, FR2, FR3 and FR4. The term antibody includes all types of antibodies, including, for example, IgA, IgG, IgD, IgE and IgM, and their respective subclasses (isotypes), e.g., IgG-1, IgG-2, IgG-3, and IgG-4; IgA-1 and IgA-2. An antibody, in some embodiments, also refers to antibody fragments and antigen-binding fragments. Antibodies suitable for practicing the methods described herein can be of various antibody formats, for example, monoclonal, polyclonal, bispecific, multispecific, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain at least two antigens or target binding sites against at least two targets described herein. The immunoglobulin molecules described herein can be of any type (e.g. IgG, IgE, IgM, IgD, IgA and IgY), class (e.g. IgG1, IgG2, IgG3, IgG4, IgA1 and IgA2) or subclass of immunoglobulin molecule. In addition, antibodies (e.g. mono-, bi-, and/or multi-specific) suitable for practicing the invention described herein can be provided in any of the alternative formats that are disclosed in the literature, for example Diabodies; Flexibodies; Camelid Antibodies, Immunobodies; Triomabs, Pepbodies, Vaccibodies, minibodies, Fcabs, UniBodies, or DuoBodies (Storz U, 2011).

PD-1 (also known as CD279 or Programmed cell death protein 1) is a member of the B7 family of receptors. In some embodiments, PD-1 refers to the human PD-1 sequence (see, e.g. NCBI Reference Sequence: NP_005009) and any naturally occurring allelic, splice variants, and processed forms thereof (Keir M et al., 2008; UniProt: Q15116). PD-1 binds PD-L1 (also known as CD274 or B7-H1) and PD-L2 (also known as CD273 or B7-DC), which are also members of the B7 family. In some embodiments, PD-L1 refers to human PD-L1 (see, e.g. GenBank: AF233516), PD-L2 refers to human PD-L2 (e.g. NCBI Reference Sequence: NM_025239), together with and any naturally occurring allelic, splice variants, and processed forms thereof.

In some embodiments, the immune-modulating agent targets one or more of PD-1, PD-L1, and PD-L2. In particular, the immune-modulating agent is PD-1 inhibitor. In some embodiments, the immune-modulating agent is an antibody specific for one or more of PD-1, PD-L1, and PD-L2. Such immune-modulating agent is an antibody such as, by way of non-limitation, nivolumab, (ONO-4538/BMS-936558, MDX1106, OPDIVO), pembrolizumab (KEYTRUDA), pidilizumab (CT-011), MK-3475, BMS 936559, MPDL3280A, and others recently reviewed (Tan S et al. 2016).

In some embodiments, the BO-11X formulation (or a BO-11Xm formulation) is combined with one or more of BMS-936559 and MEDI4736 for treatment of, for example, advanced solid tumors. In some embodiments, the BO-11X formulation is combined with one or more MPDL3280A (optionally with vemurafenib) and MEDI4736 (optionally with one or more of dabrafenib and trametinib) for the treatment of melanoma. In some embodiments, the BO-11X formulation is combined with one or more MPDL3280A (optionally with erlotinib) and MEDI4736 (optionally with tremelimumab) for the treatment of NSCLC. In some embodiments, the BO-11X formulation is combined with MPDL3280A (optionally with one or more of bevacizumab and sunitinib) for the treatment of RCC. In some embodiments, the BO-11X formulation is combined with MPDL3280A for the treatment of solid or hematological malignancies. In some embodiments, the BO-11X formulation is combined with one or more MPDL3280A (optionally with one or more of bevacizumab, chemotherapy and cobimetinib); MEDI4736 (optionally with tremelimumab) and MSB0010718C for the treatment of solid tumors. In some embodiments, the BO-11X formulation is combined with AMP-224 for the treatment of advanced cancer. In some embodiments, the BO-11X formulation is combined with nivolumab (optionally with iliolumbar (anti-KIR)) for the treatment of advanced solid tumors. In some embodiments, the BO-11X formulation is combined with nivolumab for the treatment of castration-resistant prostate cancer, melanoma, NSCLC, and RCC. In some embodiments, the BO-11X formulation is combined with pembrolizumab for the treatment of colon cancer. In some embodiments, the BO-11X formulation is combined with pembrolizumab for the treatment of gastric cancer, head and neck cancer, TNBC, and urothelial cancer. In some embodiments, the BO-11X formulation is combined with nivolumab (optionally with ipilimumab) for the treatment of gastric cancer, pancreatic cancer, small-cell lung cancer, and TNBC. In some embodiments, the BO-11X formulation is combined with nivolumab (optionally with ipilimumab) for the treatment of glioblastoma. In some embodiments, the BO-11X formulation is combined with nivolumab for the treatment of hepatocellular cancer. In some embodiments, the BO-11X formulation is combined with pembrolizumab for the treatment of Hodgkin lymphoma, myeloma, myelodysplastic syndrome, and non-Hodgkin lymphoma. In some embodiments, the BO-11x formulation is combined with pidilizumab for the treatment of malignant gliomas. In some embodiments, the BO-11X formulation is combined with one or more of nivolumab (optionally with one or more of ipilimumab, and multiple class 1 peptides and montanide ISA 51 VG; and optionally sequentially with ipilimumab) and pembrolizumab for the treatment of melanoma. In some embodiments, the BO-11X formulation is combined with pembrolizumab for the treatment of melanoma and NSCLC. In some embodiments, the BO-11X formulation is combined with one or more of nivolumab (optionally with one or more of gemcitabine/cisplatin, pemetrexed/cisplatin, carboplatin/paclitaxel, bevacizumab, erlotinib, and ipilimumab) and pembrolizumab for the treatment of NSCLC. In some embodiments, the BO-11X formulation is combined with pidilizumab (optionally with gemcitabine) for the treatment of pancreatic cancer. In some embodiments, the BO-11X formulation is combined with pidilizumab (optionally with one or more of sipuleucel-T and cyclophosphamide) for the treatment of prostate cancer. In some embodiments, the BO-11X formulation is combined with one or more of nivolumab (optionally with one or more of sunitinib, pazopanib, and ipilimumab), pembrolizumab (optionally with pazopanib), and pidilizumab (optionally with dendritic cell/RCC fusion cell vaccine) for the treatment of RCC. In some embodiments, the BO-11X formulation is combined with one or more of anti-LAG3 (BMS-986016, optionally with nivolumab), nivolumab (optionally with interleukin-21), and AMP-554 for the treatment of solid tumors. In some embodiments, the BO-11X formulation is combined with pembrolizumab for the treatment of solid tumors.

In some embodiments, the immune-modulating agent targets one or more of CD137 or CD137L. In some embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the BO-11X formulation is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an antibody such as, by way of non-limitation, ipilimumab (MDX-010, MDX-101, Yervoy, BMS) and/or tremelimumab (Pfizer). In some embodiments, the BO-11X formulation is combined with ipilimumab(optionally with bavituximab) for the treatment of one or more of melanoma, prostate cancer, and lung cancer.

In some embodiments, the immune-modulating agent targets CD20. In some embodiments, the immune-modulating agent is an antibody specific CD20. For instance, in some embodiments, the immune-modulating agent is an antibody such as, by way of non-limitation, Ofatumumab, obinutuzumab (GAZYVA), AME-133v, Ocrelizumab, TRU-015, and veltuzumab.

Validation of BO-11X Formulations

The pre-clinical validation of therapeutic efficacy of a BO-11X formulation (in accordance to the present invention, including a BO-11Xm formulation, and as exemplified by BO-112 in the Examples) can be performed in cell-based assays and, most interestingly, in animal models where different experimental criteria can be tested and compared to establish the most appropriate conditions to achieve therapeutic effects effectively, using the BO-11X formulation alone or in combination with a candidate or approved anti-cancer drug, These criteria include the doses, administration route, the order and/or the frequency of administration of either compound at the scope to identify which are the better conditions for therapeutic use of a BO-11X formulation (alone, as a BO-11Xm formulation, or synergistically with a candidate or approved anti-cancer drug) in terms of efficacy, safety, and/or clinical use. When using animal and/or ex vivo models, BO-11X formulations can be validated using one or more of the following criteria: cancer cell cytotoxicity, PARP activation, immunogenic cell death, therapeutic efficacy (in particular through apoptosis and/or necrosis of cancer cells, either directly or indirectly by abscopal effect), increased expression of markers on immune cell populations, increased populations of immune cells, and the other assays shown in the Examples.

The effects of different dosages of a BO-11X formulation (or a BO-11Xm formulation), number of and/or site of administration (in particular, by injecting it in one or more sites), each compound, route of administration, frequency, and/or time point for administration can be associated to relevant end-points and physiological parameters that are measured in biological samples obtained from cells or (preferably) animals that are exposed to the tested compounds, alone or in combination with other drugs. A non-limiting list of such parameters includes regression of tumor size, block of tumor growth and/or proliferation of tumor cells, apoptosis, reduced tumor vascularization or metastasis, overcoming resistance to a common anti-cancer drug (or otherwise improving the response to such a drug in the treated population), reduced treatment related-adverse events on normal tissues and functions, modulation of immune response and/or of immune cells having specific activities and features, identification of biomarkers or specific cell populations in biological materials (e.g. present in cancer cell preparations, tumor biopsies or biological fluids) whose increase (or decrease) is known in the literature as being associated to anti-cancer effect in general, and in particular to survival of animal models and possibly of cancer patients. Whenever possible, such end-points are measured at intermediate and final time-points following the administration of each test compound, or a test combination of compounds at a given dose and/or regimen, by using a specific route of administration and/or pharmaceutical formulations.

The therapeutic, anti-cancer efficacy of BO-11X formulation (or BO-11Xm formulations) can be tested alone or in combination with standard-of-care, conventional treatments (such as radiotherapy, chemotherapy, inhibitors of cellular kinases, drugs having epigenetic effects, etc.) or treatments involving novel mechanisms and/or novel candidate anti-cancer drugs. Indeed, a category of novel anti-cancer compounds that can be tested in combination with a BO-11X formulation are those improving the anti-tumor immune responses within tumor microenvironment, by providing a systemic antitumor immunity that targets disseminated tumor cells are eliminated. This approach has been proven successful in animal models and patients and can improve the outcome of conventional therapies such as radiotherapy or chemotherapy (see, for example, Galluzzi L et al., 2014; Vacchelli E et al., 2013; Van der Jeught K et al., 2015).

This growing panel of new cancer drugs targets the mechanisms by which cancer cells escape from immune detection and destruction by human body. Cancer-specific immunotherapies may provide a series of advantages when compared to other cancer therapies (e.g. tumor cell specificity). Indeed, the identification of a series of molecular targets for cancer immunotherapies is allowing major advances in defining the mechanisms and compounds that can provide an appropriate co-stimulatory (or co-inhibitory) effect on immune responses against tumors with respect to their plasticity, heterogeneity, resistance, or microenvironment.

A non-limiting list of cancer passive or active immunotherapies, each acting on different molecular targets and/or mechanisms, includes tumor-targeting or other immunomodulatory monoclonal antibodies, oncolytic viruses, immunostimulatory cytokines, adoptive cell transfer and other cell-based therapies, DNA- or peptide-based vaccines, inhibitors of immunosuppressive metabolism, or agonists of pattern recognition receptors. Among these mechanisms, molecular targets against which antibodies or other compounds having either agonistic or antagonistic activity (depending on their role in immune response or cancer escape from immune response) include a series of cell membrane proteins such as PD-1, PD-L1, PD-L2, CTLA-4, CD137, CD38, OX-40, CD26, TIM3, and LAG3 that are checkpoints for tumor development and against which different agonistic or antagonistic antibodies are available commercially or in scientific repositories for characterizing their specificity and/or level of anti-cancer effect against the human antigen or (when dealing with animal models) the corresponding rodent antigen.

Despite impressive patient responses to agents targeting these co-stimulatory or co-inhibitory molecules (e.g. therapies that are based on an anti-PD-1 or anti-PD-L1 antibody) the clinical response to immune checkpoint inhibitors is still incompletely or inefficiently achieving the desired therapeutic effect in too many cancer patients. A BO-11X formulation in an appropriate combination with a compound such as an anti-PD-1, anti-CTLA4, or anti-CD137 antibody may enhance the reduction of tumor growth and metastasis (or increase the number of subjects presenting such reduction), when compared to the effect of the administration of one of those two anti-cancer agents alone, possibly beyond the additive effects that may be expected.

The therapeutic effects of BO-11X formulations (or BO-11Xm formulations) can be evaluated in one of the several cell-based models that are based on isolated or mixed cell culture including primary cancer cells or established cancer cell lines, preferably from a human origin. Examples of cancer cell lines for validating BO-11X formulations can be defined according to cancer type such as melanoma (human SK-Mel-19, SK-Mel-103 and UACC62 cells; murine B16 cells), carcinoma (mouse Hepa 1-6 cells; rat FAO cells), breast cancer (human BT483, HCC1143, HCC1937, MDA-MB-231, MDA-MB-415, MDA-MB-468, and BT549 cells), pancreatic cancer (human MiaPaCa2, IMIM-PC2, Panc1, Panc0203, Panc 3.27, or BxPc3 cells), or other relevant cell lines that are available through ATCC, other official or academic repositories, or commercial providers. The anticancer effects of BO-11X formulations can be evaluated using a plurality of metrics, including period of time, frequency, and/or dose that is required to have a block of proliferation, the death, the expression of biomarkers, and/or the release of signaling molecules (such as chemokines or Interferon Beta) that indicate a potentially relevant effect of the BO-11X formulation to be confirmed under a variety of physiological conditions.

Accordingly, the effects of BO-11X formulations (or BO-11Xm formulations) can be evaluated in tumor animal models in which the anti-tumor response due to the administration of an exemplary formulation such as BO-112 is assessed in different protocols for both monotherapy and combination treatment (e.g. together with a CPI such as an anti-PD-1 antibody) throughout a shorter or longer period of time after administration. The study may be pursued by administering BO-112 and/or anti-PD-1 antibody in animals at a given time of tumor development due to proliferation of injected cells, that is after a specific number of days following the injection of cancer cells or (preferably) that present the desired tumor size (e.g. an average size of 80-100 mm$^3$), or even following its disappearance (for evaluate any effect of each drug or drug combination on tumor relapse). The study would also involve control compounds that are either negative (e.g. vehicle alone) or positive controls, such as chemotherapeutic or other anti-cancer drugs that are indicated in the literature as standard for drug effectiveness for a specific tumor and/or in a given animal model. These activities of validation in animal models and animal cell may also lead to the development of BO-11X formulation for veterinary use.

The animal model is typically a mouse model in which the cancer appears following either the transfer and engraftment of human cancer cells (derived from an immortalized cell line or a cancer biopsy that is obtained from a patient) or the induction (or transfer) of mouse tumor cells in the animals. Cells can originated from different types of tumor (e.g. lung carcinoma, melanoma, or lymphoma) and can be injected sub-cutaneously in the flank of each respective mouse for the detection of a tumor and for analyzing tumor size and/or composition throughout the study. Mice are then treated by randomizing them into groups each of a size allowing statistical analysis of results (e.g. 3, 5, 10, 12, 15, 20 or more animals for each control or treatment group).

Possible improvements afforded by that a BO-11X formulation such as BO-112 and a checkpoint inhibitor such as an anti-PD-1 antibody may induce improvements in cancer animal models (in particular when appropriately combined in terms of amount, order, or other administration criteria), increased animal survival after treatment and/or tumor disappearance, reduced tumor relapse, limited or delayed toxicity and/or resistance effects, and an improvement in the response to re-challenge of tumor inoculation after termination of the treatment with BO-112 and/or anti-PD-1 antibody.

The exemplary BO-11X formulation that is identified structurally and functionally above as BO-112 formulation and an anti-PD-1 antibody can be administered (alone or in combination, in single or multiple doses) at different locations with respect to tumor cells and/or in different amount. Typically, BO-112 and the monoclonal antibody specific for mouse PD-1 (e.g. clone RMP1-14 from BioLegend or similar ones available from other providers) are injected sub-cutaneously, intravesicularlly, intraperitoneally, peritumorally or intratumorally (depending on the model and tumor molecular and pathological features) at a concentration that is determined with respect to animal weight (e.g. between 0.01 and 2.5 mg/kg), concentration in the injected volume (e.g. between 0.01 and 0.5 mL, and/or content in each dose (e.g. between 0.01 and 250 µg per dose). In particular, the dose-response of BO-112 at different concentrations, combined with a fixed anti-PD-1 antibody dose (or vice versa), may permit determination of any advantageous effect following the significant reduction in the amount of either compound that is administered due to the combination with the other compound (e.g. unaffected or even improved efficacy and/or safety profile; abscopal effects in tumors that are in different, untreated locations).

BO-112 composition (or a BO-112m composition) can be injected in one or multiple cycles (e.g. 2, 3, 4, or more) that are separated by a fixed, desired number of days (1, 2, 3, 5, 7, or more). Alternatively, when BO-112 is co-administered with the anti-PD1 antibody, BO-112 can be injected immediately before (or after) the antibody (or in a single injectable preparation), again in one or multiple cycles (that are separated by given number of days. Still alternatively, the two agents may be formulated, or administered in any sequential order, but separated by a variable period of time (e.g. 1 hour, 3 hours, 6 hours, 12 hours, 18 hours, 24 hours, 36 hours, 2 days or more). In particular, when BO-112 is administered after the anti-PD-1 antibody, its subsequent administration (alone or further in combination with the anti-PD-1 antibody) may provide an anti-tumor rescue effect in animals in which anti-PD-1 antibody was ineffective against tumor cells, overcoming any specific tumor resistance or escape mechanism. At the end of the period of treatment, all surviving animals can be left untreated for 1, 2, 3, or more consecutive weeks to monitor if and how tumors reappear, with or without re-challenging animals that had a complete regression of tumor with a further sub-cutaneous injection of cancer cells.

The effects of BO-112 compositions (or a BO-112m compositions), alone or in combination with the anti-PD1 antibody as described above, can be assessed as interim results that are reported during the study without sacrificing the animals (e.g. by measuring tumor size, percentage of mice still alive, bodyweight, or behavioural criteria) or after sacrificing the animal (or in already dead mice) for determining molecular features of tumor and/or normal cells (including total number and/or specific sub-populations of NK cells, tumor-infiltrated lymphocytes, splenocytes, incorporation of radiolabeled precursors, and other cells that may be involved in the anti-tumor local or systemic immune responses, such as. Myeloid-derived suppressor cells (MD-SCs), regulatory T cells (Tregs); tumor associated neutrophils (TANs), M2 macrophages, and tumor associated macrophages (TAMs). I parallel, the presence/absence of relevant biomarkers can be determined by PCR amplification of relevant RNAs, or at protein level on the surface of cells within tissues or circulating in blood, such as cytokines or chemokines by using standard immunological assays and kits. This global phenotype analysis can be performed by using cells isolated from tumors, blood, spleen, lymph nodes, or other relevant tissues and locations, for detecting any statistically and/or therapeutically relevant change in the number of cells expressing cell surface markers that are detected by flow cytometry and described in the literature such as CD3, CD4, CD25, FoxP3, CD8, PD-1, PD-L1, PD-L2, PTEN, CTLA-4, CD137, CD96, CD73, CD90, CD47, CD69, CD26, TIM3, LAG3, Gr1, CD11b, Ly6C, Ly6G, NKp46, CD16, NKG2D, NKp44, NKp30, CD45, and CD31. Such cells can be also evaluated at the level of tumor antigen-specific immune response, expression of relevant transcription factors, cytokines or chemokines (e.g. IFN-gamma, IFN-beta, TNFalpha, HIF1a, HIF2a, p53), or by using other cell-based assays.

Additionally, macroscopic examination of organs and skin and microscopic, pathological analysis in either immune-deficient fully immune competent animal models can further indicate about the efficacy of the study compounds (alone or in the combination) or of their toxicity, such as organ inflammation and necropsy. The quantitative data that are generated in similar studies can be compared among the different experimental groups by using the appropriate statistical tests, with and without corrections for multiple testing, at the scope to evaluate which therapeutic (in particular anti-tumor) effects are provided by the administration of a BO-11X formulation, alone or in combination with another anti-cancer agent.

Methods of Treatment and Patient Selections

In some embodiments, the present invention relates to a method for treating, reducing, ameliorating, or preventing cancer growth, survival, metastasis, epithelial-mesenchymal transition, immunologic escape or recurrence, comprising administering by administering a BO-11X formulation (or a BO-11Xm formulation) and one or more immune-modulating agents. The cancer may be an oncological disease. The cancer may be a dormant tumor, which may result from the metastasis of a cancer. The dormant tumor may also be left over from surgical removal of a tumor. The cancer recurrence may, for example, be tumor regrowth, a lung metastasis, or a liver metastasis.

In some embodiments, the cancer is one or more of basal cell carcinoma, biliary tract cancer; bladder cancer; bone cancer; brain and central nervous system cancer; breast cancer; cancer of the peritoneum; choriocarcinoma; connective tissue cancer; cancer of the digestive system (including esophageal, stomach, colon, rectal or other gastrointestinal cancer); eye cancer; cancer of the head and neck; glioblastoma; hepatic carcinoma; hepatoma; intra-epithelial neoplasm; kidney, adrenal, or renal cancer; leukemia; liver cancer; lung cancer (e.g. small-cell lung cancer, non-small cell lung cancer, lung adenocarcinoma, and lung squamous carcinoma); melanoma; myeloma; neuroblastoma; oral cavity cancer (lip, larynx, tongue, mouth, and pharynx); pancreatic cancer; prostate cancer; retinoblastoma; rhabdomyosarcoma; cancer of the respiratory system; salivary gland carcinoma; skin cancer; squamous cell cancer; testicular cancer; thyroid cancer; uterine, endometrial, cervical, vulval, ovarian or other gynecological cancer; cancer of the urinary system; lymphoma including B-cell lymphoma, Hodgkin's and non-Hodgkin's lymphoma (NHL; including specific types such as low grade/follicular, small lymphocytic, intermediate grade/follicular, intermediate grade diffuse, high grade immunoblastic, high grade lymphoblastic, high grade small non-cleaved cell, or bulky disease NHL), mantle cell and AIDS-related lymphoma; chronic lymphocytic leukemia; acute lymphoblastic leukemia; Hairy cell leukemia; chronic myeloblastic leukemia; as well as other carcinomas and sarcomas; post-transplant lymphoproliferative disorder (PTLD), as well as abnormal vascular proliferation associated with phakomatoses or edema (such as those that associated with brain tumors). In some embodiments, the cancer is a biliary tract cancer. In some embodiments, the biliary tract cancer is selected from pancreatic cancer, gallbladder cancer, bile duct cancer, and cancer of the ampulla of Vater. In some embodiments, the cancer is liver cancer. In some embodiments, the cancer is colon cancer. In some embodiments, the biliary tract cancer is cholangiocarcinoma and/or an adenocarcinoma. Alternatively, the cancer may be listed among the list of rare diseases, being defined according to the critera of incidence as defined in Europe or USA, and Indicated in regularly updated lists made available in the website of organisations such as the International Rare Cancers Initiative (http://www.irci.info) or RaraCare (http://www.rarecare.eu).

In some embodiments the BO-11X formulation (or a BO-11Xm formulation) and/or immune-modulating agent is used to treat cancers at various stages (e.g. Stage I, or II, or III, or IV). By way of non-limiting example, using the overall stage grouping, Stage I cancers are localized to one part of the body; Stage II cancers are locally advanced, as are Stage III cancers. Whether a cancer is designated as Stage II or Stage III can depend on the specific type of cancer. In one non-limiting example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, or spread to other organs or throughout the body.

In some embodiments, the BO-11X formulations (or BO-11Xm formulations) and/or the immune-modulating agent reduces side effects of the therapies that a patient may experience. For example, the combination therapy of an BO-11X formulation and one or more immune-modulating agent may allow for a lower dose of the BO-11X formulation and/or one or more immune-modulating agent (e.g. as compared to monotherapy) and thereby increase the therapeutic window of either agent. In some embodiments, the lowered dose mitigates one or more side effects without (or minimal) loss of efficacy. In some embodiments, the BO-11X formulation and/or immune-modulating agent is used to treat a subject that has a treatment-refractory cancer. In some embodiments, the BO-11X formulation is used to treat a subject that is refractory to one or more immune-modulating agents, in particular the one that is actually combined with the BO-11X formulation.

In some embodiments (see also Example 3), the subject is refractory to a PD-1 and/or PD-L1 and/or PD-L2 agent, including, for example, nivolumab (ONO-4538/BMS-936558, MDX1106, or OPDIVO), pembrolizumab (KEYTRUDA), pidilizumab (CT-011), MK-3475, BMS-936559, Ibrutinib, and/or MPDL328OA-refractory patients. For instance, in some embodiments, the subject is refractory to an anti-CTLA-4 agent, e.g. ipilimumab (Yervoy)-refractory patients (e.g. melanoma patients). In some embodiments, the subject is refractory to a BO-11X formulation. Accordingly, in some embodiments the present invention provides methods of cancer treatment that rescue patients that are non-responsive to various therapies, including monotherapy of an BO-11X formulation or one or more immune-modulating agents.

In particular, certain types of cancer may be selected for the treatment with a BO-11X formulation (or a BO-11Xm formulation) according to their sensitivity to immunotherapy such as with an anti-PD1, anti-PD-L1 or anti-CTLA4 antibody. These cancers include melanoma, non-small cell lung cancer, cancer of the head and neck, renal cell cancer, bladder cancer, hepatocellular carcinoma and Hodgkin's lymphoma. Alternatively, a BO-11X formulation (or a BO-11Xm formulation) may be administered for treating cancer types which have not previously demonstrated any sensitivity to immunotherapy, such as prostate cancer, breast cancer, colorectal cancer or subtypes of these cancers that for example have a high mutational burden (or microsatellite instability), such as those presenting JAK, POLE, or other mutations detected by gene sequence and/or expression profiling affecting response to interferon, in particular interferon gamma, as reported in literature (Ayers M et al. 2017; Budczies J et al., 2016; Gong J et al. 2017; Shin D S et al., 2017; Zaretsky J M et al. 2016). In general, BO-11X formulation can be also combined with miRNAs, (or other non-coding RNA molecules that act as inhibitors or modulators of the expression of specific genes, such as RNAi shRNA, or siRNA; Ling H, 2016; Larsson M et al., 2017), mRNA (i.e., RNA coding for proteins when into cells), or any other RNA-based drugs, in which a BO-11X formulation such as a BO-112 formulation may improve RNA delivery, activity, and/or stability (e.g. miRNAs to silence IDO, TGFbeta, or NKG2D ligand) by means of this combined or co-administration method. Synergistic combinations of BO-112 formulation with complementary mechanisms of action would include drugs that are designed to reduce the immunosuppression and T cell exhaustion, to potentiate T cell activation or to increase numbers of tumor specific T cells. These drugs can target tumor cells, T cells or other cells in the tumor microenvironment and include molecules such as immunomodulatory mAbs (CTLA4, PD1 or PDL1, LAGS, TIM3, CD137, OX40, GITR, CD40, CD25), activator), cytokines (1L2, IL12), other neutralizing mAbs (TGFbeta, IDO1, IL10, NKG2d ligand), CAR-T cells, or cancer antigen vaccines. Present data also support combination with agents that target Tregs and drugs involved (and targeting) in DNA repair and/or replication. In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey (e.g. baboon) or chimpanzee.

In some embodiments, methods of the invention are useful in treatment a human subject. In some embodiments, the human is a paediatric human. In other embodiments, the human is an adult human. In other embodiments, the human is a geriatric human. In other embodiments, the human may be referred to as a patient or a subject. In some embodiments, the human is a female. In some embodiments, the human is a male.

Treatment Regimens and Combination Therapies

In one embodiment, the present invention relates to a BO-11X composition (or a BO-11Xm composition), preferably a BO-112 composition (or a BO-112m composition), as defined herein, for use in treatment of a cell growth disorder characterized by abnormal growth of human or animal cells, comprising the following steps:
  (i) administering to said subject (patient) according to at least one treatment with said composition or said formulation; followed by
  (ii) a follow-up (analysis) of the medical conditions of said subject (patient) and/or a follow-up of gene expression within tumor, cancer and/or immune cells thereof; together with or followed by
  (iii) evaluation of (a) cell infiltrates within tumor biopsies (e.g. CD8 and/or CD4-positive T cells), (b) necrosis and/or apoptosis of cancer cells in tumor biopsies, or (c) increase/decrease of circulating immune cells in blood.

This approach is useful for evaluating administration of a BO-11X formulation such as BO-112, and can be further developed according to available technologies, for example in connection to imaging for evaluating tumor burden and/or response (see also Example 3).

In other embodiment, such as those summarized in FIGS. 14 and 15, the present invention relates to:
  (i) a BO-11X composition (or a BO-11Xm composition), preferably a BO-112 composition (or a BO-112m composition), as defined herein, or
  (ii) a formulation obtainable by treating a cell or tissue from a subject (patient) ex vivo with a BO-11x composition (or a BO-11Xm composition), preferably a BO-112 composition (or a BO-11Xm composition), as defined herein, for use in treatment of a cell growth disorder characterized by abnormal growth of human or animal cells, wherein said composition is administered to said subject (patient) according to a process comprising the following steps:
  (i) at least one treatment with said composition or said formulation; followed by
  (ii) a follow-up (analysis) of the medical conditions of said subject (patient) and/or a follow-up of gene expression within tumor, cancer and/or immune cells thereof and/or evaluation of (ii,a) cell infiltrates within tumor biopsies (e.g. CD8 and/or CD4-positive T cells), (ii,b) necrosis and/or apoptosis of cancer cells in tumor biopsies, or (ii,c) increase/decrease of circulating immune cells in blood; together with or followed by
  (iii) at least one treatment with said composition, and/or said formulation and/or a standard of care protocol and/or an anti-cancer drug or treatment (already approved or within a clinical study protocol) against which the subject (patient) was resistant, not responding or poorly responding, wherein the treatment with said composition, and/or said formulation in step (i) and step (iii) may be performed using the same or a different dose, means of administration (intratumoral or subcutaneous/intramuscular), or regimen. More preferably, the standard of care treatment, drug in clinical development, or other treatment against which the subject (patient) was resistant, not responding or poorly responding is radiotherapy, chemotherapy, anti-PD-1/PD-L1 therapy (or other immune checkpoint inhibitor), cancer antigen-based vaccination or cell-based therapy (including CAR-T therapy). Preferably, the gene expression involves mRNA and/or protein expression of specific sets of proteins.

In another embodiment, the present invention relates to a BO-11X composition (or a BO-11Xm composition), preferably a BO-112 composition, for use in treatment of a cell growth disorder that is characterized by abnormal growth of human or animal cells, wherein said composition is administered to a subject (patient) according to an administration regime comprising
(I) at least one (or first) intratumoral injection of said composition; and
(II) at least one (or second) subcutaneous or intramuscular injection of said composition, wherein said at least one intratumoral injection is administered prior to said at least one subcutaneous or intramuscular injection.

Analogously, the present invention also relates to a method of treatment in a subject (patient) of a cell growth disorder characterized by abnormal growth of human or animal cells, wherein a BO-11X composition (or a BO-11Xm composition), preferably a BO-112 composition (or a BO-112m composition), is administered to said subject according to an administration regime comprising:
(I) at least one (or first) intratumoral injection of said composition; and
(II) at least one (or second) subcutaneous or intramuscular injection of said composition, wherein said at least one intratumoral injection is administered prior to said at least one subcutaneous or intramuscular injection.

Alternatively, the administration regimen for BO-11X composition (or a BO-11Xm composition) or the corresponding method of treatment in a subject (patient) of a cell growth disorder characterized by abnormal growth of human or animal cells may comprise:
(i) at least a first intratumoral injection in a first lesion; and
(ii) at least a second intratumoral injection in the same lesion or if no longer present, one or more additional lesions.

Preferably, in the composition for use and said method of treatment, said subsequent intratumoral injection is performed at least 24 hours after said at least one intratumoral injection, even more preferably at least 48 hours after having performed two to four intratumoral injections, still more preferably at least one week after having performed four intratumoral injections. Even more preferably, in the composition for use and said method of treatment, the administration of said at least one intratumoral injection is repeated at equal or different time intervals.

These administration regimens (or corresponding methods of treatment) may also involve administering a 30-11X composition (or a BO-11Xm composition):
(a) before or after administering a second therapeutic agent, said second therapeutic agent being administered by intratumoral or peritumoral injection in the same and/or other lesion(s), by sub-cutaneous injection, or by intramuscular injection;
(b) after determining if the subject is resistant, insensitive, or poorly (or not) responding to said second therapeutic agent;
(c) and then a said second therapeutic agent is administered to a subject after determining if, following the administration BO-11X composition (or a BO-11Xm composition), there is a statistically significant increase in number of circulating immune cells and/or change in the expression of any of the genes of Table I (see Example 4).

With respect to the embodiments (b) and (c) above, the second therapeutic agent is preferably selected from anti-CTLA4, anti-PD1, anti-PDL1, CAR-T cells, cancer antigen vaccines, or agents that target regulatory T cells, metabolic enzymes, DNA repair and/or replication, or a protein expressed by any of the genes of Table I.

Alternatively, the administration regimen for BO-11X composition (or a BO-11Xm composition) may involve the ex vivo treatment of cells with such a composition. In this case, the BO-11X composition (or a BO-11Xm composition) for use as a medicament by administering it to a subject according to an administration regimen comprising:
(i) obtaining cells from the subject;
(ii) contacting said cells to said composition ex vivo; and
(iii) Administering such cells to the subject;

Preferably the treatment of a cell growth disorder characterized by abnormal growth of human or animal cells as indicated in all the previous embodiments is a treatment of cancer. More preferably, in the composition for use and said method of treatment, said at least one (or any second or other additional) intratumoral, peritumoral, subcutaneous or intramuscular injection is performed at least 24 hours after said at least one (or first) intratumoral injection, even more preferably at least 48 hours after having performed two to four intratumoral injections, still more preferably at least one week after having performed four intratumoral injections. Even more preferably, in the composition for use and said method of treatment, the administration of said at least one intratumoral injection is repeated at equal or different time intervals. Preferably, the administration of the at least one sub-cutaneous injection is repeated at equal or different time intervals and/or the intramuscular injection is repeated at equal or different time intervals. Much more preferably, in the composition for use and said method of treatment, the composition administered in the at least one sub-cutaneous injection or intramuscular injection comprises the same or a lower amount of polyinosinic-polycytidylic acid [poly(I:C)] than in the at least one intratumoral injection. In some embodiments, present invention provides for specific cancer treatment regimens with BO-11X formulations (or a BO-11Xm composition), and a second, immune-modulating agent (and optionally one or more additional therapeutic agent). For example, in some embodiments, the BO-11X formulation, e.g. BO-112, may be administered to a patient first to normalize tumor vascularization, optionally by reducing or ablating hypoxia. Alternatively, such first administration of the BO-11X formulation, e.g. BO-112, may stimulate and/or increase T lymphocytes (e.g. CD4+ and CD8+ T cells) and/or NK cells tumor and/or inhibit and/or decrease recruitment of immunosuppressive cells (e.g. myeloid-derived suppressor cells (MDSCs), regulatory T cells (Tregs); tumor associated neutrophils (TANs), M2 macrophages, and tumor associated macrophages (TAMs) to the tumor. In some embodiments, the present therapies may alter the ratio of M1 versus M2 macrophages in the tumor site to favor M1 macrophages. the BO-11X formulations, in some embodiments, may induce a long lasting (i.e. greater than transient) vascular normalization. For example, BO-11X formulation-vascular normalization may last greater than 1, or 2, or 3, or 4, or 5, or, or 6, or 7, or 14 days, or 21 days. Accordingly, in some embodiments, this long-lasting BO-11X formulation-vascular normalization (or, in general, the changes in immune cells that infiltrate tumor or circulating in blood stream) may allow for a sustainable permissive tumor microenvironment that is more likely to be responsive to one or more immune-modulating agents. That is, in some embodiments, the BO-11X formulation may potentiate, rescue, or sensitize towards immune-modulating therapy.

Alternatively, the BO-11X formulations (or BO-11Xm compositions, e.g. BO-112 or BO-112m), is administered to a patient before or after starting treatment with one or more immune-modulating agents. For instance, in some embodiments, the immune-modulatory agent targets one or more co-inhibitory molecules and reduces or eliminates immunosuppression. In this favourable context, i.e. upon removal of suppression, the BO-11X formulations (or BO-11Xm compositions, e.g. BO-112 or BO-112m), is administered is administered to stimulate the immune system. Alternatively, the immune-modulatory agent targets one or more co-stimulatory molecules first and the BO-11X formulation (or a BO-11Xm composition, e.g. BO-112 or BO-112m), is administered second to bolster this effect, for example, synergistically.

Further, as described herein, the BO-11X formulation and/or immune-modulating agent can be combined with an additional therapeutic agent in the context of, for example, co-administration, a treatment regimen or a co-formulation.

In some embodiments, the BO-11X formulations (or a BO-11Xm compositions) and/or immune-modulating agent, optionally with an additional therapeutic agent, can be administered sequentially. The term "sequentially" as used herein means that the additional therapeutic agent and the BO-11X formulation and/or immune-modulating agent are administered with a time separation of more than about 60 minutes. For example, the time between the sequential administration of the additional therapeutic agent and the BO-11X formulation and/or immune-modulating agent can be more than about 60 minutes, more than about 2 hours, more than about 5 hours, more than about 10 hours, more than about 1 day, more than about 2 days, more than about 3 days, or more than about 1 week apart. The optimal administration times may depend on the rates of metabolism, excretion, and/or the pharmacodynamic activity of the additional therapeutic agent and the BO-11X formulation and/or immune-modulating agent being administered. Either the additional therapeutic agent or the present agents may be administered first.

In some embodiments, the BO-11X formulations (or BO-11Xm compositions) and/or immune-modulating agent, optionally with an additional therapeutic agent, can be administered simultaneously. The term "simultaneously" as used herein, means that the additional therapeutic agent and the BO-11X formulation and/or immune-modulating agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and BO-11X formulation and/or immune-modulating agent can be by simultaneous administration of a single formulation (e.g. a formulation comprising the additional therapeutic agent and the BO-11X formulation and/or immune-modulating agent) or of separate formulations (e.g., a first formulation including the additional therapeutic agent and a second formulation including the BO-11X formulation and/or immune-modulating agent).

Co-administration also does not require the additional therapeutic agents be administered to the subject by the same route of administration. Rather, each therapeutic agent can be administered by any appropriate route, for example, parenterally or non-parenterally.

Such a combination may lead to synergism and/or additive and/or potent effects at a lower dose of the BO-11X formulation (or a BO-11Xm composition) and/or immune-modulating agent. For example, when the BO-11X formulation is combined with one or more immune-modulating agents the effective amount of the BO-11X formulation may be lower than what it would be in a monotherapy. In some embodiments, the BO-11X formulation is combined with an immune-modulating agent and the effective amount of the BO-11X formulation is a sub-therapeutic dose, for example, when the immune-modulating agent is combined with a BO-11X formulation the effective amount of the immune-modulating agent may be lower than what it would be in a monotherapy. In some embodiments, the immune-modulating agent is combined with a BO-11X formulation and the effective amount of the immune-modulating agent is a sub-therapeutic dose. In some embodiments, the immune-modulating agent is combined with a BO-11X formulation and an additional therapeutic agent and the effective amount of the additional therapeutic agent is a sub-therapeutic dose. The term "sub-therapeutic dose or amount" means that a dose or amount of a pharmacologically active substance is below the dose or amount of that substance that is administered, as the sole substance, to achieve a therapeutic effect. The sub-therapeutic dose of such a substance may vary depending upon the subject and disease condition being treated, the weight and age of the subject, the severity of the disease condition, the manner of administration and the like, which can readily be determined by one of ordinary skill in the art. In one embodiment, the sub-therapeutic dose or amount of the chemotherapeutic agent is less than 90% of the approved full dose of the chemotherapeutic agent, such as that provided in the U.S. Food & Drug Administration-approved label information for the chemotherapeutic agent. In other embodiments, the sub-therapeutic dose or amount of the chemotherapeutic agent is less than 80%, 70%, 60%, 50%, 40%, 30%, 20% or even 10% of the approved full dose, such as from 20% to 90%, 30% to 80%, 40% to 70% or another range within the values provided herein.

In some embodiments, the effective amount of the immune-modulating agent is less than an effective amount used in monotherapy for the same cancer and/or a combination therapy with an agent besides a BO-11X formulation for the same cancer. In some embodiments, the effective amount of the BO-11X formulation is less than an effective amount used in monotherapy for the same cancer or clinical status, and/or a combination therapy with an agent (such as an immune-modulating agent) for the same cancer or clinical status.

In some embodiments, the BO-11X formulation (or a BO-11Xm composition) is combined with one or more immune-modulating agents (e.g. 1, or 2, or 3, or 4, or 5 immune-modulating agents) and, optionally, one or more additional therapeutic agents (e.g. 1, or 2, or 3, or 4, or 5 additional therapeutic agents). Such combinations may lead to synergism and/or additive and/or potent effects at a lower dose of the BO-11X formulation and/or immune-modulating agent and/or the one or more additional therapeutic agents. Co-administration may be simultaneous or sequential. Further the pharmaceutical compositions including the BO-11X formulation and/or immune-modulating agent may comprise the additional therapeutic agent (e.g. via co-formulation). That is, in some embodiments, two or more of any of the agents disclosed herein may be co-formulated. Further, in some embodiments, the BO-11X formulation and/or immune-modulating agent may be administered to a patient that is undergoing treatment with one or more additional therapeutic agent. Further, in some embodiments, the BO-11X formulation and/or immune-modulating agent may supplant a patient's current treatment with one or more additional therapeutic agent.

Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, the agents described herein are used as an adjuvant therapy in the treatment of a cancer. In some embodiments the therapeutic agents described herein are administered as a neo-adjuvant therapy prior to resection. In certain embodiments, neo-adjuvant therapy refers to therapy to shrink and/or downgrade the tumor prior to any surgery. In some embodiments, neo-adjuvant therapy means a therapeutic agent described herein is administered to cancer patients prior to surgery or other technique allowing tumor ablation.

In some embodiments the therapeutic agents described herein are useful as a maintenance therapy after an initial treatment with a first-line therapy, including without limitation any of the additional therapeutic agents of the present disclosure.

In some embodiments, the present invention provides a treatment regimen or a method for treating cancer or tumors in a subject that includes administering simultaneously or sequentially a therapeutically effective amount of a BO-11X formulation and/or an immune-modulating agent and one or more of the additional therapeutic agents described herein. In some embodiments, the present invention provides a treatment regimen or a method for treating cancer or tumors in a subject that includes administering simultaneously or sequentially a therapeutically effective amount of a 80-11X formulation and/or an immune-modulating agent and one or more of the anti-cancer agents described herein, including but not limited to chemotherapeutic agents. Suitable chemotherapeutic agents to be used in the methods of the present invention may include those described herein. In certain embodiments, the chemotherapeutic agent is one or more of 5-fluorouracil (5-FU), doxorubicin, gemcitabine, paclitaxel, and cisplatin. By way of example, in some embodiments, the present invention provides combining a BO-11X formulation and/or an immune-modulating agent with one or more common cancer treatment regimens (by way of non-limiting illustration, FOLFOX, FOLFIRI, IFL, FL (Mayo), QUASAR, Machover schedule, CAF, CMF, ECF, and FEC).

In some embodiments, the additional therapeutic agent is an antihyperproliferative agent. Antihyperproliferative agents include, but are not limited to, doxorubicin, daunorubicin, mitomycin, actinomycin D, bleomycin, cisplatin, VP16, enedyine, taxol, vincristine, vinblastine, carmustine, melphalan, cyclophsophamide, chlorambucil, busulfan, lomustine, 5-fluorouracil, gemcitabin, BCNU, or camptothecin.

In addition, the additional therapeutic agent can further include the use of radiation. In addition, the methods of treatment can further include the use of photodynamic therapy.

Salts, Pharmaceutical Compositions and Doses

In some embodiments, the present invention provides for the formulation, compositions (where formulation and composition is used interchangeably in the present invention), and agents described herein and pharmaceutically acceptable esters, pro-drugs, salts, solvates, enantiomers, stereoisomers, active metabolites, co-crystals, and other physiologically functional derivatives thereof.

In one aspect, the present invention provides agents described herein, and a pharmaceutically acceptable carrier or excipient. The pharmaceutical composition can be in any suitable form appropriate for the desired use and route of administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol mono-stearate, talc, sodium chloride, dried skim milk, glycerol, propylene, glycol, water, ethanol and the like. Other examples of suitable pharmaceutical excipients are described in *Remington's Pharmaceutical Sciences* (edited by Allen, Loyd V., Jr; $22^{nd}$ edition, 2012).

Additionally, the pharmaceutical compositions or formulations of the present invention may contain adjuvants such as preservatives, wetting agents, emulsifying agents, pH buffering agents, and dispersing agents. Further, auxiliary, stabilizing, thickening, lubricating, and colouring agents can be included. Prevention of the action of microorganisms may be ensured by the inclusion of various antibacterial and antifungal agents, for example, paraben, chlorobutanol, phenol acid, and the like. The pharmaceutical compositions may also include isotonic agents such as sugars, sodium chloride, and the like. Where necessary, the pharmaceutical compositions can also include a solubilizing agent. Also, the agents can be delivered with a suitable vehicle or delivery device as known in the art. Compositions for administration can optionally include a local anaesthetic such as, for example, lidocaine to lessen pain at the site of the injection.

The pharmaceutical compositions or formulations of the present invention can take the form of solutions, suspensions, emulsions, drops, tablets, pills, pellets, capsules, capsules containing liquids, powders, sustained-release formulations, suppositories, emulsions, aerosols, sprays, suspensions, or any other form suitable for use. Thus, the composition described herein may be comprised in a capsule, tablet, pill, caplet, bottle, ampoule, sachet, syringe, cartridge, nebulizer or other container. In one embodiment, the pharmaceutical composition is in the form of a capsule. In another embodiment, the pharmaceutical composition is in the form of a tablet.

In some embodiments, the administration of any of the described agents and compositions is any one of oral, intra-venous, and parenteral. In some embodiments, routes of administration include, for example: oral, intra-dermal, intra-muscular, intra-peritoneal, intra-venous, sub-cutaneous, intra-nasal, epidural, sub-lingual, intra-nasal, intra-cerebral, intra-hepatic, intra-pancreatic, intravesicular, intravaginal, transdermal, rectally, by inhalation, or topically, for example, to the ears, nose, eyes, or skin. In some embodiments, the administering is effected orally or by parenteral injection. The mode of administration can be left to the discretion of the practitioner, and depends in part upon the site of the medical condition and/or concurrent treatments (being, for instance, chemotherapy, radiotherapy, or in combination with antibodies, vaccines and other cancer-targeting drugs). In some embodiments, administration results in the release of any agent described herein into the bloodstream.

Any agent, pharmaceutical composition and/or formulation described herein can be administered orally. Such agents and/or pharmaceutical compositions can also be administered by any other convenient route, for example, by intravenous infusion or bolus injection, by absorption through epithelial or muco-cutaneous linings (e.g., oral mucosa, rectal and intestinal mucosa, etc.) and can be administered together with an additional therapeutic agent. Administration can be systemic or local. Various delivery systems are known, e.g., encapsulation in liposomes, microparticles, microcapsules, capsules, etc., and can be used. In specific embodiments, it may be desirable to administer locally to the area in need of treatment.

In one embodiment, an agent described herein and/or pharmaceutical composition and/or formulations described herein is formulated in accordance with routine procedures as a composition adapted for oral administration to humans. Solid dosage forms for oral administration include, for example, capsules, tablets, pills, powders, and granules. In such dosage forms, the active agent is mixed with at least one inert, pharmaceutically acceptable excipient or carrier such as sodium citrate, di-calcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinyl-pyrrolidone, etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium agents, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulphate, glycerylbehenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

Liquid dosage forms for oral administration include pharmaceutically acceptable emulsions, solutions, suspensions, syrups and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Dosage forms suitable for parenteral administration (e.g. intra-venous, intra-muscular, intra-hepatic, intra-pancreatic, intra-peritoneal, sub-cutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Pharmaceutical compositions of this invention for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions, and by the use of surfactants.

Any agent described herein and/or pharmaceutical composition described herein can be administered by controlled-release or sustained-release means or by delivery devices that are known to those of ordinary skill in the art. Such dosage forms can be useful for providing controlled- or sustained-release of one or more active ingredients using, for example, hydropropyl cellulose, hydropropylmethyl cellulose, polyvinylpyrrolidone, Eudragit, other polymer matrices, gels, permeable membranes, osmotic systems, multilayer coatings, microparticles, liposomes, microspheres, or a combination thereof to provide the desired release profile in varying proportions. Suitable controlled- or sustained-release formulations can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Formulations comprising the agents described herein and/or pharmaceutical compositions of the present invention may conveniently be presented in unit dosage forms and may be prepared by any of the methods known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g. wet or dry granulation, powder blends, etc., followed by tableting using conventional methods known in the art).

It will be appreciated that the actual dose of the agents described herein and/or pharmaceutical compositions of the present invention to be administered according to the present invention may vary according to the particular agent, the particular dosage form, and the mode of administration. Many factors that may modify the action of the BO-11X formulations (e.g. body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the agents described herein and/or pharmaceutical compositions of the present invention can be administered in unit dosage forms (e.g., tablets or capsules) containing, for example, from about 0.01 mg to about 1,000 mg of poly(I:C) molecules within the BO-11X formulation or BO-11Xm formulation, e.g. wherein said individual BO-11X formulation is formed by making a complex from about 0.01 mg to about 10 mg of poly(I:C)] preferably about 0.5 mg to about 2.5 mg of poly(I:C), more preferably about 1 mg to about 2 mg of poly(I:C), inclusive of all values and ranges there between. In some embodiments, the agents described herein and/or pharmaceutical compositions of the present invention are administered at an amount of from about 0.01 mg to about 1000 mg of poly(I:C) molecules within the BO-11X formulation daily, or from about 0.1 mg to about 10 mg daily [e.g. wherein said individual daily BO-11X formulation is formed by making a complex from about 0.01 mg to about 1000 mg, preferably about 0.01 mg to 10 mg of poly(I:C)], inclusive of all values and ranges there between.

In some embodiments, a suitable dosage of the agents and/or pharmaceutical compositions of the present invention is in a range of about 0.001 to about 10 mg of poly(I:C) molecules within the BO-11X formulation/kg of body weight of the subject, preferably 0.003 to about 10 mg of poly(I:C) molecules within the BO-11X formulation or BO-11Xm formulation (as calculated with respect to a subject or, if needed, as calculated with respect to the body weight of the subject), more preferably 0.005 to about 10 mg of poly(I:C) molecules within the BO-11X formulation/kg of body weight of the subject and even more preferably 0.01 to about 10 mg of poly(I:C) molecules within the BO-11X formulation per kg of body weight of the subject [e.g. wherein said individual BO-11X formulation administered is formed by making a complex from about 0.005 mg to about 10 mg of poly(I:C)] per kg of body weight of the subject, preferably about 0.003 mg to about 10 mg of poly(I:C)] per kg of body weight of the subject, more preferably about 0.001 mg to about 10 mg of poly(I:C)] per kg of body weight of the subject, inclusive of all values and ranges there between. 01 mg/kg to about 10 mg/kg of body weight of the subject, inclusive of all values and ranges there between. In other embodiments, a suitable dosage of the BO-11X formulation and/or immune-modulating agent and/or additional therapeutic agent is in a range of about 0.01 mg/kg to about 10 mg/kg of body weight, or in a range of about 0.05 mg/kg to about 1 mg/kg of body weight.

In accordance with certain embodiments of the invention, the agents and/or pharmaceutical compositions described herein may be administered, for example, more than once daily, about once per day, about every other day, about every third day, about once a week, about once every two weeks, about once every month, about once every two months, about once every three months, about once every six months, or about once every year. In one embodiment a suitable dosage of the agents and/or pharmaceutical compositions of the present invention is in a range of 0.1 to 10 mg of poly(I:C) molecules within the BO-11X formulation per subject (patient), preferably 0.5 to 2 mg of poly(I:C) molecules within the BO-11X formulation per subject, more preferably 0.6 to 1 mg per subject over a cycle of treatments. In particular, when a composition of the present invention is administered. by intra-cutaneous or intratumoral injection, the total amount of composition can be adapted consequently.

Kits

The invention also provides kits that can simplify the administration of the agents and/or pharmaceutical compositions described herein. The kit is an assemblage of materials or components, including at least one of the agents described herein. The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to affect a desired outcome, such as to treat or prevent, for example, cancer, gynaecological disorders, or infections. Optionally, the kit also contains other useful components, such as, diluents, buffers, pharmaceutically acceptable carriers, syringes, catheters, applicators, filters, (micro)needles, pipetting or measuring tools, bandaging materials or other useful paraphernalia as may be readily recognized by those of skill in the art. In particular, the kit may include a device for more precise (eg image-guided) intratumoral or peritumoral drug delivery, implantable (or not) drug eluting devices in the format of matrices (including porous, biodegradable, and/or polymeric structures and scaffolds), encapsulation system, or other appropriate packaging for clinical use.

Since the BO-11X compositions or BO-11Xm compositions can be used directly, in combination with other compounds (e.g. vaccines, drugs, adjuvants, etc.), using different routes of administration, and/or involving the retrieval and analysis of cells or samples from the patients, the kit may include specific materials such as syringes for intra-tumoral, intra-intra-muscolar, and/or sub-cutaneous injections (pre-filled or not), vehicle for dilution, vials for storing biological materials from the patients, and/or antibodies for detecting specific cell markers.

EXAMPLES

Example 1: Structural Characterization of jetPEI-Based Poly(I:C) Preparations (BO-11X Formulations) and Initial In Vitro Functional Validation Materials & Methods
Poly(I:C) Preparation The single-stranded polyinosinic acid [poly(I)] and polycytidylic acid [polyI] molecules used for generating double-stranded polyinosinic-polycytidylic acid [poly(I:C)] molecules] were obtained from commercial providers such as Tide Group, Carbogen, Hangzhou Fst Pharmaceutical Co, or Invivogen. Depending from the provider and the batch, the size distribution for pI(C) molecules is defined as being: <400 bases, 20-82% (with further tests performed using preparations presenting, for instance, 33%, 43%, 50%, 70%, or 73% s); 400-850 base, 15-40% (with further tests performed using preparations presenting, for instance, 20%, 27%, 30%, 34%, or 37%); 850-5000 bases, 3-50% (with further tests performed using preparations presenting, for instance, 5%, 6%, 13%, 30% 34%, 42%, or 48%); >5000 bases, 1% or less (generally absent). Depending from the provider and the batch, the size distribution for poly(I) molecules is defined as being: <400 bases, 80-99% (with further tests performed using preparations presenting, for instance, 81%, 86%, 91%, 95%, or 98%); 400-850 bases, 1-20% (with further tests performed using preparations presenting, for instance, 6%, 8%, 12%, or 17%); 850-5000 bases, 0-5% (with further tests performed using preparations presenting, for instance, 3%, 1% or below); >5000 bases, 1% or less (generally absent). Acceptance criteria for manufacturing BO-11X formulations that apply to poly(I) anloly (C) powder or solutions also include maximum absorption (at wavelength of 248±1 nm and of 268±1 nm for poly(I)Id poly(C), respectively), endotoxin content (≤10 EU/m–), pH (6.0-8.0), and sedimentation coefficient (≥4S).

Batch poly(I) preparatil and poly(C) preparations were obtained, annealed, and purified as described in PCT/EP2016/078078. Briefly, poly(I) preparlons and poly(C) preparations were obtained separatelyling powder poly(C) in the same manner and at the same concentration. Additional steps of filtration could be implemented to further improve quality of starting solutions using membranes with a 300 kDa cut-off or a 500 kDa cut-off (Pellicon 2 cassette, Millipore). The permeates of these filtration steps are concentrated and freed from small size impurities, such as monomers, over a 30 kDa membrane (Pellicon 2 cassette, Millipore). The resulting retentate for each solution is mixed with a concentrated buffer solution (such as PBS 10X). For both solutions, the optical density was determined to calculate the concentration as a basis for a 1:1 stoichiometry for the following annealing step, adjusting consequently the total volume before annealing step. Poly(I) solution is mixed and stirred with poly(C) solution molecules at 55-62° C. for 30 minutes. The resulting solution is slowly cooled down at room temperature for approx. 3 hours for annealing single-stranded molecules and generating poly(I:C) molecules, and finally filtered over a G3 glass pore filter (pore size of approx. 15-40 µm).

This annealing process generates a solution containing a pool of different double-stranded poly(I:C) molecules that is then applied on a chromatographic GPC column. The chromatography is performed with Omnifit glass column of 5 cm diameter that was filled with a slurry of 700 mLToyopearl HW-65F in 40 mM sodium phosphate buffer. The slurry was allowed to settle slowly, followed by washing with 40 mM sodium phosphate buffer (pH=6.9) at increasing flow rate from 10 mL/min to 60 mL/min. The column was installed in a preparative HPLC device consisting of two feed pumps, a UV detector, sampling valves and a computer. The reaction mixture from the annealing was loaded on the column and eluted with 40 mM sodium phosphate buffer (flow=50 mL/min, pH=6.9). Target fractions were taken when the UV signal was between 100 mV and 1250 mV, and pooled for further work-up using four desalting cycles of dilution and concentration using a tangential flow device (TFF, Millipore Pellicon 2, regenerated cellulose, equipped with three membrane cassettes of 0.1 m$^2$ each, 300 kDa cut-off). Inlet and outlet were connected to the first glass bottle with the pooled chromatography fractions. Final retentate and washing solution were filtered over a membrane to give a clear, colorless solution that was desalted using isopropanol, freeze-dried, and lyophilized at room temperature (at 1 mbar for approx. 5 days). A preparation of poly(I:C) can be obtained by the following exemplary process: poly(C) solution was heated at 61 to 66° C. for 1.5 h before mixing this with the poly(I) solution and stirring at 55 to 58° C. for 70 minutes, after which the mixture was cooled and filtered over a 0.2 µm membrane.

Different commercial In vivo-JetPEI [having an average molecular weight comprised between 8.3 and 22.5 kDa, and a polydispersity index <1.5, as determined from that of PEOX (polyethyleneoxide, precursor to PEI) by Gel Permeation Chromatography (GPC: SOP GPC-0044) and sterile filtered through a 0.2 µm filter] was obtained from PolyPlus (catalog no. 201-50G). Some conditions applicable to the chromatography and/or filtration step, absence or presence of a freezing step, together with buffer and annealing time, were adapted for further reducing solution viscosity or precipitation of complexes. Either Mannitol or Glucose is used as excipient in the final formulation. Solution 1 containing JetPEI is obtained by either using JetPEI in a concentrated liquid preparation or solubilizing solid bulk preparations of JetPEI (having a molecular weight comprised between 17 and 23 kDa) in an amount of sterile water for injection to reach 150 mM, and mixing for obtaining a homogeneous solution. A further dilution step is performed to reach a concentration of 11.25-11.7 mM, before the final dilution to 5.62-5.85 mM in the final vial. Solution 2 contains poly(I:C) molecules and glucose monohydrate in an amount that, after mixing with JetPEI, provides a solution containing 5% glucose (weight/total volume of said composition) and poly(I:C) at 0.5-0.7 mg/mL of the total volume of said composition, whereby said poly(I:C) complexes with said JetPEI. Solution 1 and 2 are independently sterilized using a double filtration through 0.2 µm filters (Sartopore® 2 150 0.2 µm, fully validated as sterilizing grade filters (according to ASTM F-838-05 guidelines) using a pump Watson Marlon (speed 30 rpm). The automated mixing of the two solutions is performed in each vial using a sequential process: (i) Solution 1 is added to the vial using a Watson-Marlow pump to dose 5.95-6.05 g (6 mL; density: 1 g/mL), (ii) Solution 2 is added over the solution 1 using a 1.8 mm internal diameter tube connected to a G20-0.9 µm needle using Flexicon pump at 550 rpm speed to dose 6.08-6.40 g (6 mL). Results can be improved by using a T-piece mixer. In case of aggregates of particles (e.g. with a size in the range of 1-100 µm or larger) that may be still present by visual inspection at the end of the manufacturing process (or during its storage) due to electrostatic interactions, the product can be filtered over a 0.8 µm filter prior to use (for instance, before its injection), without altering neither biological properties nor mono-modal diameter distribution of the particles within the composition. For example, the BO-112 formulation can be filtered through a Minisart Syringe Filter (Sartorious) with an exclusion size of 0.8 µm. Vials (having variable volumes of BO-112 formulations, e.g. 1 mL, 2 mL, 5 mL, 10 mL, or more) are sealed with sterile pyrogen-free rubber stoppers and crimp with aluminum capsules and individually labelled. These vials can be used directly for injections or their content can be diluted in an appropriate vehicle prior to the use.

The size of poly(I:C) molecules within BO-11X preparations was determined and compared by chromatography or by using agarose gels and unlabeled or [$^{32}$P] labeled poly(I) and poly(I:C) preparations. Briefly, 1 µg of poly(I) and poly(I:C) (PBS) are loaded into the agarose gel and electrophoresis was performed for 1 hour at 80 volts in TBE buffer. Depending from the size distribution of initial poly (C) and poly (I) molecules, the size distribution of poly(I:C) molecules that are present in BO-11X preparations was determined also by chromatography as being: <400 bases, 7-57% (with further tests performed using preparations presenting values comprised between 10% and 30%, for instance, 11%, 15%, 17%, 21%, 26%, or 28%); 400-850 bases, 20-45% (with further tests performed using preparations presenting values comprised between 20% and 30%, for instance, 23%, 25%, or 27%); 850-5000 bases, 20-70% (with further tests performed using preparations presenting values comprised between 40% and 60%, for instance, 42%, 45%, 52%, 53%, or 55%); >5000 bases, 0-9% (with further tests performed using preparations presenting values comprised between 0% and 5%, for instance, 3%, 1%, or 0%). The size of different batch poly(I) preparations and poly(C) preparations were evaluated and compared by chromatography.

BO-112 compositions are produced and validated at a concentration and with particle size distribution as described for BO-11X formulations in PCT/EP2016/078078. BO-112 compositions are provided as vials containing poly(I:C) at 0.5-0.8 mg/mL concentration. The stability of BO-112 compositions in these vials was confirmed after 1 year of storage at 2-8° C.

Commercially Available Poly(I:C)-Containing Formulations

Poly-ICLC is a poly(I:C) preparation that is stabilized with polylysine and carboxymethyl-cellulose (Ewel C et al., 1992; WO2005102278). LyoVec-HMW (Cat. No. tlrl-piclv) and LyoVec-LMW (Cat. No. tlrl-picwlv), and corresponding poly(I:C) preparations having high molecular weight (HMW; Cat. Name tlrl-pic) and low molecular weight (LMW; Cat. Name tlrl-picw) are available from Invivogen.

Analytical Technologies

The value for zeta average (z-average) diameter and polydispersity index of JetPEI/poly(I:C) particles in distinct BO-11X preparations (between 0.5-0.8 mg/mL, to be diluted for cell-based and other assays at a poly(I:C) concentration of 1.0 µg/mL) were determined using Zetasizer Nano ZS according to the manufacturer's instructions and in accordance with ISO 22412, based on the assumption that said particles are spherical. In general, dynamic light scattering (Nanosizer technology) is applied using v7.11 software.

In Vitro Characterization of 80-11X Preparations

The different poly(I:C)-based preparations were tested using human melanoma cells, human pancreatic cells, or human melanocytes according to the literature describing the properties of BO-110 complexes on human melanoma cell line SK-MEL-103 and human pancreatic cancer cell line c (Pozuelo-Rubio Metal., 2014; Tormo D et al., 2009; WO2011003883). Briefly, cell viability assays were performed on adherent cells at least 12 hours before treatment. The percentage of cell death at the indicated times and treatment concentrations was estimated by standard trypan blue exclusion assays on floating and adherent cells that were pooled, stained with a 0.4% trypan blue solution (Gibco Laboratories, Grand Island, NY, USA) and scored under a light microscope (a minimum of 100-500 cells per treatment were counted). Each preparation was tested for a period comprised between 12 hours and 48 hours and at concentrations poly(I:C) molecules in the different preparations that were comprised between in a range between 0.3 and 2.5 µg/ml. The death-inducing activity of BO-112 was tested in normal melanocytes and cell lines from melanoma and glioblastoma and compared to isolated components, i.e. poly(I:C) molecules and linear PEI (Jet PEI; Polyplus). Normal melanocytes were isolated from foreskins of asymptomatic donors. Melanoma cells SK-Mel-28, SK-Mel-103, and UACC62 (with mutations in p53, NRAS and BRAF respectively) were obtained from established collections at the ATCC or Memorial Sloan Kettering Cancer Centre (USA) and were subject to short tandem repeat (STR) profiling (GenePrint® 10 System) for cell line authentication. Primary cells from melanoma patients were obtained and maintained using standard protocols. Cells were plated on 96 well plates (6000 cells/well). In triplicate per experiment, with Poly(I:C) only, BO-110 or BO-112 formulations at 0.5 or 1 µg/ml for a 24 hrs or 40 hrs treatment.

Tumor Cell Death Characterization

Mouse cancer cell line B16-F10, skin melanoma, (ATCC code CRL-6475) was obtained from established collections at the ATCC; B16-OVA cells (derived from B16-F10 cells) were obtained from the Centro de InvestigaciOn Medica Aplicada (Navarra, Spain). B16 cell lines that are insensitive to IFNs were obtained from Invivogen (B16-BIue™ IFN-γ cells, Cat.no. bb-ifng; B16-Blue™ IFNα/β cells, Cat. no. bb-ifntl) and maintained as indicated by manufacturer. The characterization of the tumor cell death (apoptosis, necrosis, immunogenic cell death) induced by BO-112 formulation was investigated and compared with isolated poly(I:C) and with other TLR ligand (LPS, specific for TLR4). B16-OVA cells ($10^5$ cells/well) were cultured: alone, with ultrapure LPS (0.25 and 1 µg/mLI, InvivoGen, San Diego, CA), with BO-112 formulation (0.25, 0.5 and 1 µg/ml), or with poly I:C only (0.25, 0.5 and 1 µg/ml) for 48 hours. Cell apoptosis and necrosis rate were analysed by flow cytometry with Annexin V and 7ADD combined staining (Living cells: 7ADD negative, Annexin V negative-; cell necrosis: 7ADD positive, Annexin V negative; early apoptosis 7ADD negative, Annexin V positive; late apoptosis: 7ADD positive, Annexin V positive). The effect of BO-112 on inducing immunogenic cell death was analysed by flow cytometry by detecting the cell surface expression of MHC-1, CD95 and Calreticulin. For flow cytometry, samples were acquired in a Gallios Cytometer (Beckman Coulter) and data analyzed with Kaluza Flow Analysis Software (Beckman Coulter).

PARP Activation

In addition, the effect of BO-112 formulation on the activation of the enzyme Poly ADP ribose polymerase (PARP), which is involved in DNA repair, genomic stability, and programmed cell death, was investigated. MC38 colon adenocarcinoma (Cellosaurus code CVCL_B288, Kerafast cat. no. ENH204), and 4T1 breast cancer cells (ATCC code CRL-2539)aere obtained from established cell collections such as the ATCC. Each cancer cell line ($3\times10^6$) wasstimulated with BO-112 (0.5 µg/mL) and PARP activation was analysed at 0, 16 h and 24 h in the cell lysates by Western Immunoblotting. PARP Monoclonal Antibody (clone C-2-10, ThermoFisher Scientific) was used to identify a 116 kDa protein which corresponds to PARP and the 85 kDa apoptosis-induced cleavage product.

Results

PCT/EP2016/078078 discloses protocols and experimental data about the initial development and characterization of BO-11X formulations, leading to increased cytotoxicity of BO-11X formulations against cancer cells when compared to BO-110 complexes as described in the literature and obtained on a laboratory scale (Pozuelo-Rubio M et al., 2014; Tormo D et al., 2009; WO2011003883). The data on the BO-11X manufacturing process and resulting poly(I:C)-containing preparations in GMP conditions with the processes and preparations were compared to those disclosed in the literature.

Figure 1:
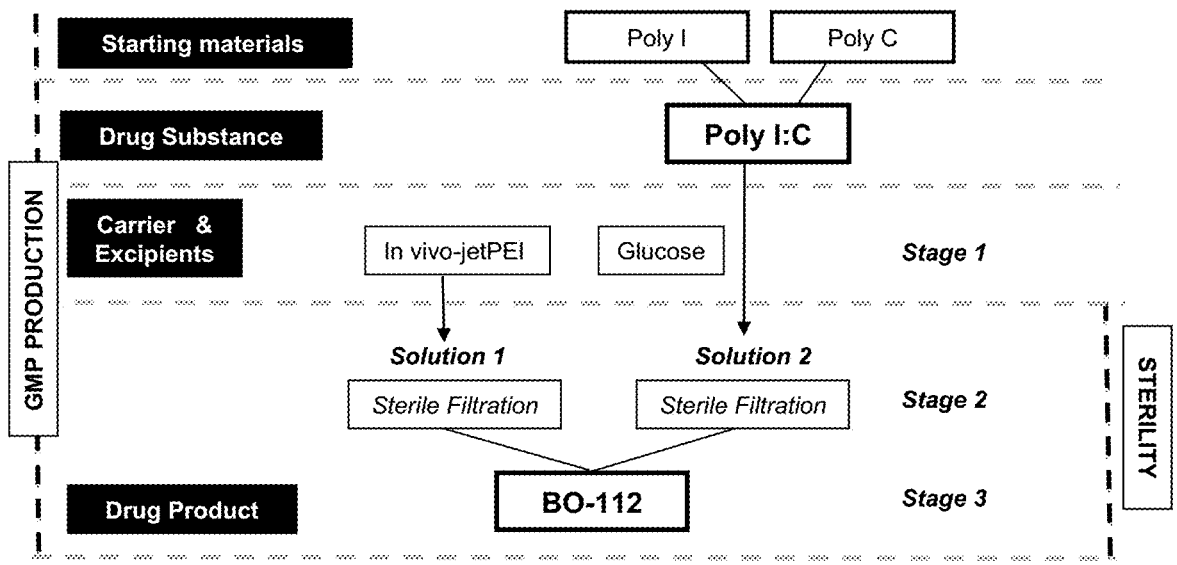
FIG. 1: GMP manufacturing and structural analysis of BO-11X aqueous compositions, as exemplified by BO-112. (A) Flowchart summarizing main steps for manufacturing BO-112 compounds as a GMP-compliant, pharmaceutical preparation comprising poly(I:C) molecules, commercial JetPEI preparations, and glucose. This approach can be applied also by using other types of polyribonucleotides that form double stranded molecules that are formed by Poly (A), poly(U), poly (C), and/or Poly (G) according to their respective pairing properties. Otherwise, this approach may involve adding another compound (being an immune-related adjuvant or therapeutic compound, such as CD40L, IL12, viral or tumor antigens, miRNA, mRNA, or other (non-coding) RNA-/nucleic acid-based drugs, or an anti-cancer drug such as inhibitors of kinases or other enzymes affecting cell replication, metabolism, or biological functions) together with (or as an alternative to) glucose or other excipient in Stage 1. (B) Size distribution of BO-112 complexes is compared to three poly(I:C)-containing commercial products (Poly-ICLC, LyoVec-HMW, and LyoVec-LMW); particle size is defined considering particle diameter in nanometers (d.nm) by Dynamic Light Scattering (zeta sizer nano ZS technology). These commercial preparations also present substantial changes in the size distribution following storage at −20° C., that BO-112 preparations do not present.
Figure 1:
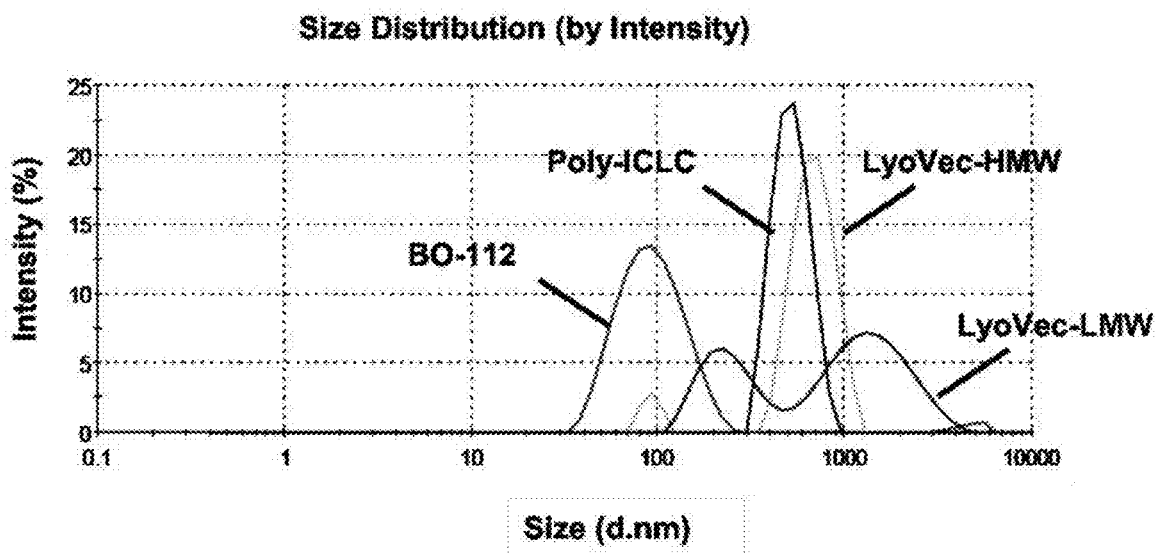

FIG. 1A provides an overview of such process for generating a first type of BO-11X preparations that are named BO-112 formulations wherein the drug substance (i.e. double stranded poly(I:C) molecules that are generated, annealing of poly(I) and poly(C) single-stranded molecules) is first mixed with an excipient like glucose in a solution that is sterilized by filtration, separately from the solution containing a polymer having the function of carrier (i.e. JetPEI). Then, these two bulk preparations are appropriately mixed into each vial to generate a large number of structurally and functionally comparable pharmaceutical formulations that are required for pharmaco-toxicological studies and clinical applications. This process may also provide poly(I:C) formulations in which a further compound (such as an immune-related adjuvant or other therapeutic compound) is present in the particles (and then in the final formulation) that are formed in Stage 1, in particular by adding such therapeutically relevant compound together with (or as an alternative to) an excipient like glucose, providing an example of BO-11Xm formulation that can be named BO-112m.

At least some of such reproducibility and acceptance criteria can be compared to the ones of other poly(I:C)-containing formulations for which anticancer activity are known. At the level of poly(I:C) molecules size, the poly(I:C) molecules that are included in the commercial Lyovec-HMW and Lyovec-LMW are covering size ranges that are clearly distinct from those provided by the BO-11X manufacturing process (with HMW almost entirely above 0.85 kb and LMW almost entirely below 0.85 kb). This size difference in poly(I:C) molecules may be dependent from the different manufacturing process and/or carrier that are associated in the complexes with poly(I:C) molecules. The Z-average values of complexes within poly(I:C)-based complexes within poly-ICLC (comprising polylysine and carboxymethylcellulose) and LyoVec-HMW/LyoVec-LMW (according to the manufacturer, comprising the cationic lipid-based transfection reagents Di-tetradecylphoshoryl-N,N,N-trimethylmethanaminium chloride, or DTCPTA and the neutral lipid 1,2-Diphytanoyl-sn-Glycero-3-Phosphoethanolamine, or DiPPE) were compared to the one of BO-112 formulations, showing that these commercial formulations contain complexes that are much bigger (in large majority larger than 200 nm) and, at least for Lyovec-LMW, with a bi-modal distribution (FIG. 1B). If this analysis is performed after a freeze/thaw cycle, these commercial preparations appear also as less stable, with a variability not observed for BO-112. Indeed, if BO-112 formulation a Z-average diameter (d. nm) of 100+/−50 nm (e.g. 82.5 nm), and without exceeding 400 nm, LyoVec-based and Poly-ICLC formulations having a Z-average value well above 300 nm, thus confirming that commercially available poly(I:C) are provided as preparations that are either heterogeneous in composition or include large particles that are poorly characterized functionally and whose size is modified during a freeze/thaw cycle.

This approach can be automated for providing BO-11X formulations (such as BO-112 preparations) with even more uniform features. This manufacturing procedure allows not only to preventing having free JetPEI, or poly(I:C) molecules in solution and not complexed within BO-112 preparations but also obtaining a controlled average diameter and the mono-modal diameter distribution of the complexes within BO-112 preparations, so that the Z-average can be modulated between 30 and 150 nm. Moreover, this approach can be adapted to include poly(I:C) molecules of different size distribution, as well as other polyribonucleotides (Poly (A), Poly(G),and/or Poly (U)) having different size, distribution of size, and/or presenting single and double-stranded regions. PCT/EP2016/078078 also discloses that commercially available poly(I:C) are provided as preparations that are either heterogeneous in composition or include large particles that are poorly characterized functionally and whose size is modified during a freeze/thaw cycle. Indeed, hyperchromicity can be also used to evaluate BO-112 formulation, and in particular the stability of double-stranded poly(I:C) molecules within the particles as a consequence of changes in temperature (or other condition) determining the separation between poly(I) strands and poly(C) strands. BO-112 formulation shown a very low hyperchromatic effect with differences in transmittance at 260 nm lower than 0.2 or 0.1. Stability of frozen BO-11X vials at −20° C. for different time has been also assessed and confirmed, at least up to one month.

Filtration and freezing of BO-112 formulation prior to administration does not promote substantial modifications to the cytotoxic properties or stability on the particles within the composition with respect to the original BO-112 formulation. For instance, compositions maintain D90% below 250 nm, zeta potential superior to 30 mV (e.g. between 40 mV and 50 mV), hydrodynamic diameter with a Z-average between 30 and 150 nm, compatibility with the use of glucose as excipient, polydispersity values comprised between 0.1 and 0.6, and other applicable criteria from European Pharmacopoeia).

Thus, BO-11X preparations, such as BO-112 preparations, are formulations that present the high level of stability and reproducibility for particles formed by poly(I:C)-JetPEI complexes having Z-average diameter (d.nm) below 200 nm (when not below 100 nm) that are not observed for commercial poly(I:C) formulations that are based on other carriers and manufacturing methods. The resulting BO-112 preparations present BO-112 complexes having a mono-modal diameter distribution, without visible particles (i.e. without a number of particles above the limit required by Eur. Pharm. 2.9.20), even if the final solution is not filtered through 5 μm after mixing the bulk solutions 1 and 2. BO-112 preparations can be filtered over a 0.8 μm filter prior to use (for instance, before its injection), therewith altering neither biological properties nor mono-modal diameter distribution of the particles within the composition. For example, the BO-112 formulation can be filtered through a Minisart Syringe Filter (Sartorious) with an exclusion size of 0.8 μm. The mixing conditions can be adapted, in particular by modifying the mixing speed between 50 rpm and 600 rpm and/or the flow speed for either poly(I:C) or JetPEI Solution between 1 mL/min and 50 mL/min. In general, BO-11X preparations (and in particular BO-112 preparations) present the following main features: colorless, no visible particles an osmolality comprised between 220 and 340 mOsm/kg, a pH comprised between pH 2 and pH 4 (e.g. between 2.7 and 3.4), an optical rotation between +1500 and +3750, a zeta potential equal or superior to 30 mV, a mono-modal diameter distribution of particle with Z-average diameter (nm) between 30 and 250 nm (for instance, between 30 and 150 nm), but preferably between 60 nm and 130 nm, and comprising poly(I:C) molecules, wherein at least 40%, 50%, or 60% of such double-stranded polyribonucleotides having a size higher than 0.85 Kb and at least 70% of such double-stranded polyribonucleotides have a size comprised between 0.4 and 5 Kb. Features such as diameter distribution of the particles can be modified by using T-piece mixer in combination with different flow speed for both Solution 1 and Solution 2. When such speed is above 20 mL/min (e.g. 30 mL/min), the turbidity of the resulting BO-112 preparation is reduced in parallel with the reduction of Z-average particle diameter and diameter distribution around this value, while maintaining mono-modality, possibly due to the change in the flow regime.

The exemplary BO-112 preparation is provided as vials comprising particles having a Z-average diameter of between 45+/−5 nm and 81+/−5 nm (e.g. 73+/−5 nm), with at least 50% of particle smaller than 85+/−20 nm, polydispersity of 0.25, the zeta potential of 38 mV, and pH 3.1. These structural properties that are maintained after freeze/thaw cycle at −20° C. or extensive exposure at room temperature can be modified in distinct batches, maintaining the acceptance criteria within specific ranges of values. In particular, when GMP and non-GMP batches are compared for physicochemical and functional properties and more reproducible and effective criteria for evaluating BO-112 formulation (and BO-11X formulations in general), more preferred ranges are defined. For instance, terapeuticallly and biological effective BO-112 formulations can present particles having an Z-average diameter of 100+/−50 nm or of 80+/−20 nm (e.g. 76 nm, 89 nm, or 96 nm), with a potential z comprised between about 35 (or 40) and 50 mV (e.g. 39 mV, 46 mV, or 50 mV) or about 40 and 45 mV (e.g. 43 mV), at least 90% of particle has a diameter below 250 nm or of 200+/−50 nm (e.g. 170 nm, 172 nm, 174 nm, 216 nm, 218 nm, 220 nm), and polydispersity between 0.2 and 0.3 (e.g. 0.21, 0.23, or 0.25). Additional criteria can be associated to features that are measured in the aqueous composition such as presence of monomeric inosinic acid below detection or irrelevant (e.g. below 1, 0.5, 0.2, or 0.1 µg/mL), osmolality comprised between 300 and 310 mOsm/kg, ionic strength below 5 mM or, preferably, below 1 mM (e.g. 0.7, 0.76, 0.78, or 0.80). These values may be modified following preservation at low temperatures (e.g. 5° C.-14-3° C.) but they should still remain within these ranges.

The Poly(I:C) and particle concentration in the vial can be adapted according to the final use. However, in order to maintain the stability of Poly(I:C)- and PEI-based complexes in the compositions, the vial should comprise BO-11X with a concentration superior to 0.1 mg/mL of Poly(I:C), possibly superior to 0.5 mg/mL of Poly(I:C) molecules, so that zeta-potential and aggregation features are stable and allow a uniform and effective use of the BO-11X preparation. The vials can be prepared for single use (containing a volume of 4 mL, 2 mL, 1 mL of BO-11X composition or less) as in larger batch preparations (containing 5 mL, 10 mL, 15 mL or more of BO-11X composition or more) that can be fractionated in 2, 3, 5 or more aliquots for single use that are administered over the period of treatment (3 days, 5 days, 7 days, 10, days, 15 days, 30 days or more).

Figure 2:
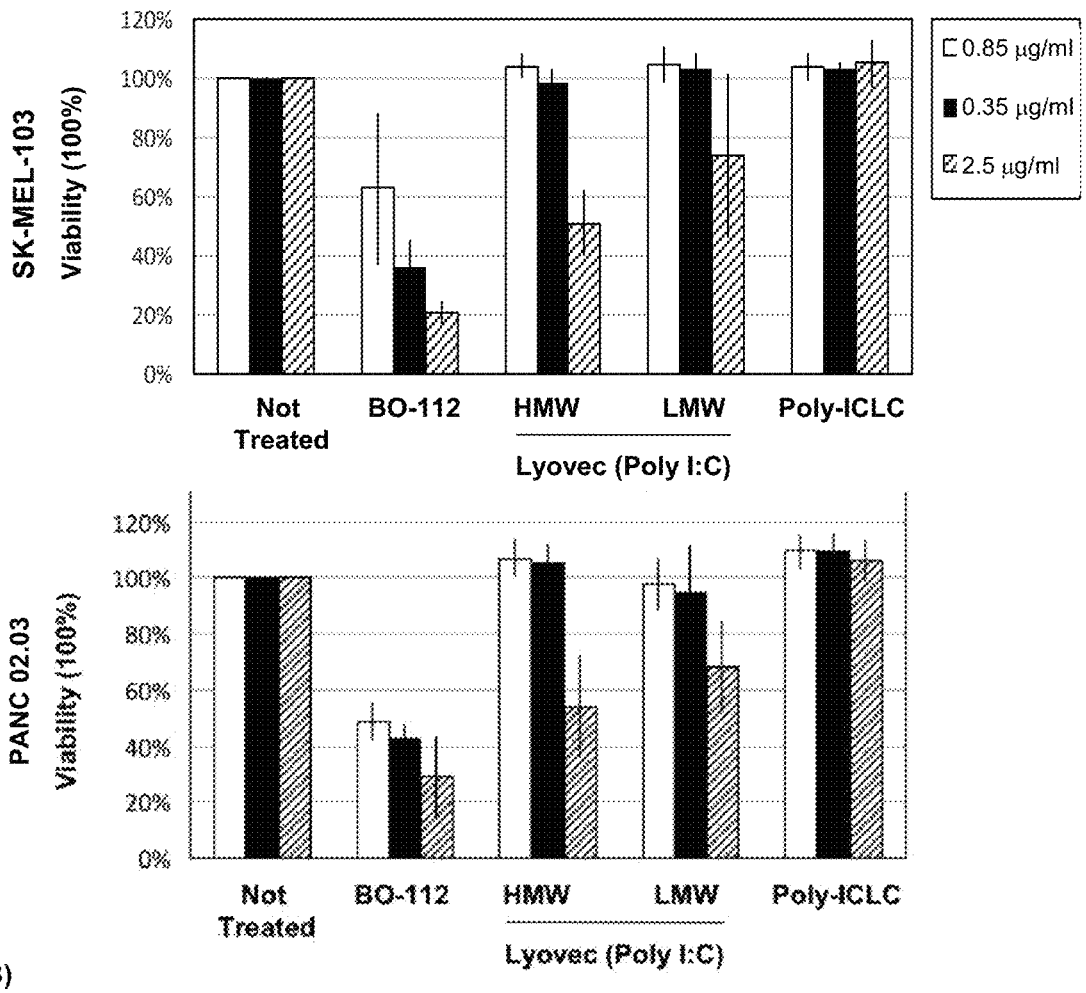
FIG. 2: Effect of different poly(I:C) formulations on cell viability in distinct cancer cell models. (A) BO-112 is compared to untreated cells and to cells treated with Poly-ICLC, LyoVec-LMW, or LyoVec-HMW, each formulation being tested at the indicated concentrations that were determined according to complex weight but with a similar content of poly(I:C) molecules in either a melanoma (SK-MEL-103) or pancreatic cancer (PANC 02.03) cell model. The cell viability data were generated using crystal violet assay method after 24 hours. This in vitro cytotoxicity assay was performed in other mouse (4T1 breast cancer, MC38 colon cancer, and B16-F10-OVA) melanoma cell lines) and human (PAN02.03 pancreatic cancer cell line) models by incubating the cells with 0.25-1.0 µg/mL of BO-112 for 24 or 48 hours, confirming the direct cytotoxic effect on such cell lines. (B) The effect of different poly(I:C) formulations on signaling molecules of therapeutic interest such as Interferon-beta (IFN-beta) expression was evaluated by RT-qPCR method in SK-MEL-103 cells that were exposed to BO-112, Poly-ICLC (or untreated, NT) for 8, 16 and 24 hours. BO-112 and Poly-ICLC formulations were used at a concentration providing a similar content of poly(I:C) molecules.
Figure 2:
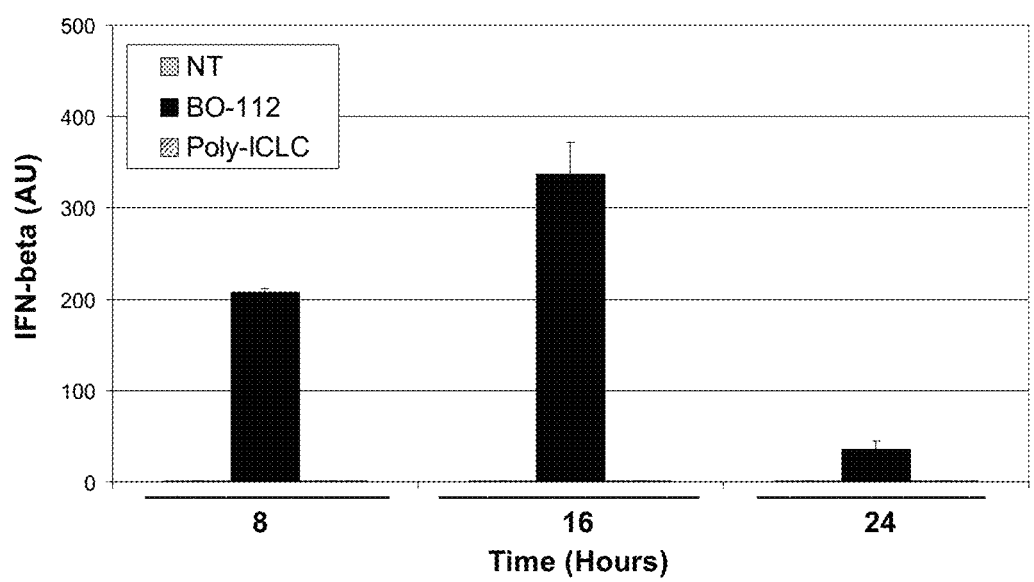

If the cytotoxic activity of BO-112 formulation is compared with commercial formulations, the latter ones appear much less effective in killing cancer cells in at least two in vitro models (FIGS. 2A and B). The cytotoxic activity of BO-11X preparations can be measured and validated for further uses in different types of cancer cell lines, representative of different cancer indications. These effects may be also studied by measuring the expression and/or secretion of proteins that are known to modify, and possibly improve, the cellular response against cancer cells. For instance, a BO-112 formulation induces, much more efficiently that Poly-ICLC, Interferon-beta expression in a melanoma cell line over a period of at least 24 hours (FIG. 2C). This in vitro evidence can be used for evaluating not only which types of cancer can be more efficiently treated by administering a BO-11X formulation but also for evaluating which other cancer treatments (such as cell-based or antigen-based vaccines, adjuvants, antibodies, chemotherapeutic drugs, radiotherapy, cell-based therapies, immunotherapy, epigenetic therapy, or inhibitors of enzymatic activities such as kinases or metabolic enzymes) may act in a more effective manner when administered in combination with a BO-11X formulation (e.g. by reducing the dosage, the frequency, and/or the period of treatment with this other approach).

Figure 3:
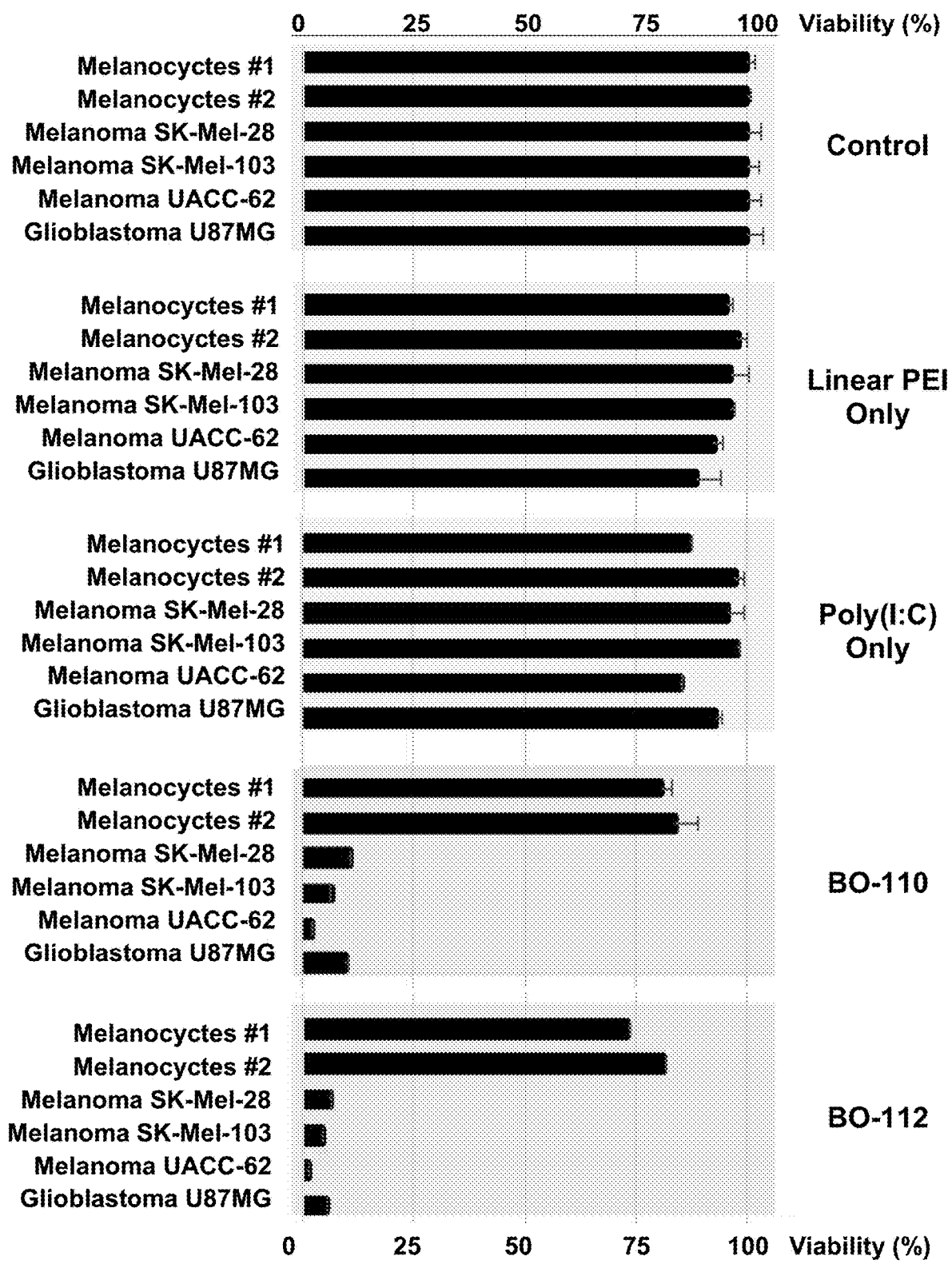
FIG. 3: Effect of linear PEI alone, poly(I:C), and two different PEI/poly(I:C) formulations (BO-110 and BO-112) on the viability of normal, primary melanocytes (preparations #1 and #2) and four cancer cell lines, demonstrating the specific cytotoxicity of such PEI/poly(I:C) formulations against cancer cell lines. Poly(I:C) content used in preparation of the Poly(I:C) only, BO-110, and BO-112 treatments administered is identical (1 µg/mL per 40 hours of treatment).

Indeed, the specificity of such cytotoxic effects against cancer cell lines, and not against normal primary cells, by BO-11X formulations (as previously described for lab-scale BO-110 formulations; Tormo D et al., 2009) was confirmed in vitro by comparing the activities with appropriate compounds and cell controls (FIG. 3). Neither linear PEI L nor poly(I:C) molecules alone affect in a significant manner the viability of tumor cells (melanoma or glioma. Only when linear PEI and poly(I:C) molecules are complexed as provided in BO-112 formulation, a significant killing of tumor cells, without affecting viability of normal melanocytes, is observed. Cell-based assays for in vitro cytotoxicity may be part of the validation and ranking of batches of BO-112 formulation prior to further (pre-)clinical uses. Such assays can be based on the effect on human melanoma cell lines (such as SK-Mel-19, SK-Mel-28, SK-Mel-103 and SK-Mel-147 cells) after 24, 36, or 48 hour exposure to a batch of BO-112 formulation at 1, 2 or more standard concentrations (e.g. 0.35, 0.5, 0.85, 1.0, or 1.5 µg/mL, with or without prior filtration using a 0.8 µm filter) in culture medium, using vehicle or other particle-free solution having comparable criteria (such as osmolality, pH, or ionic strength) as negative control and SDS or other biological or chemical cytotoxic agent.

As a whole, the poly(I:C)-based, particle-based, composition-based, and cytotoxicity-based criteria that are applied for producing and validating BO-11X formulations (and in particular BO-112 formulations) make this formulation of poly(I:C) a structurally different and functionally improved formulation with respect to previous poly(I:C)-based formulation either commercially available (see figures) and/or described in the literature (Schaffert D et al., 2011; WO2011003883; WO2015173824). With respect to these latter publications, these non-GMP, poly(I:C)-based formulations require the addition of groups such as PEG (with shielding activity) and/or EGF peptides (for cell targeting) in order to achieve the desired level of cytotoxicity using particles-containing solutions having substantially higher size, at an higher N/P ratio, with additional chemical complexity in production, and with a specificity for cancer cells limited to those expressing a cell surface antigen such as EGFR.

Figure 4:
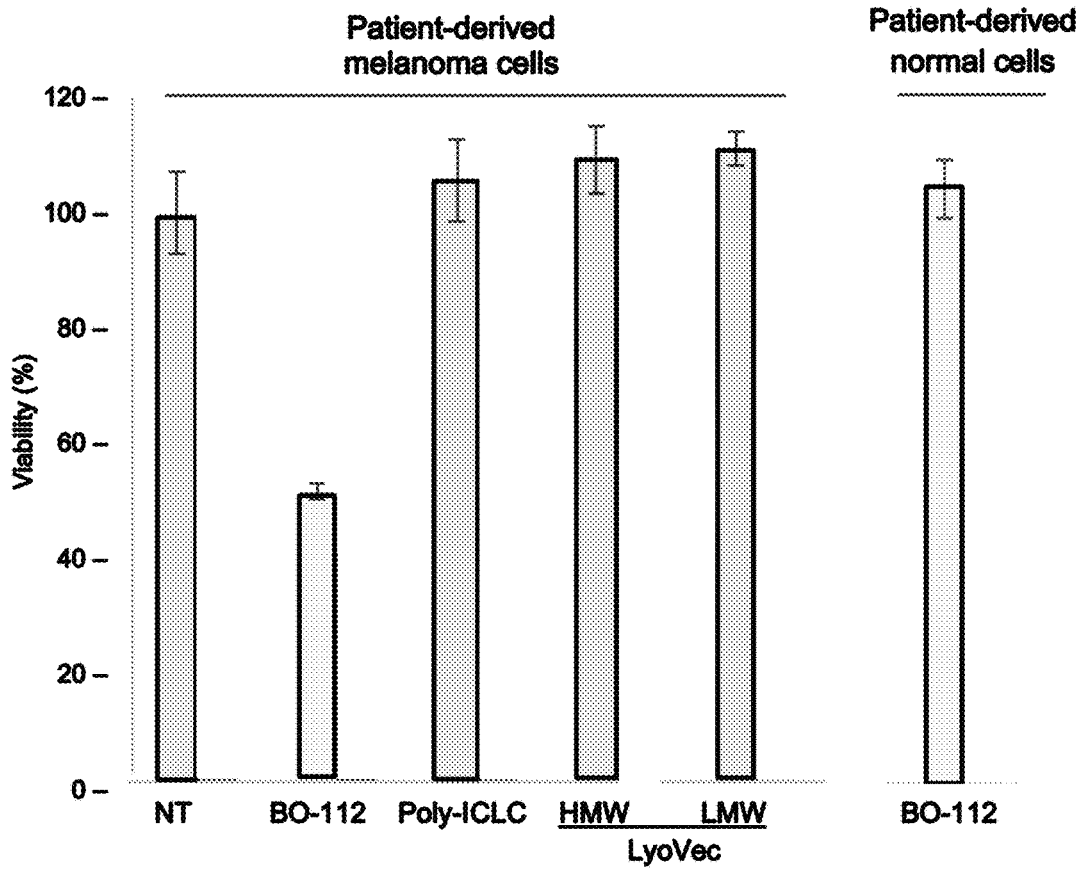
FIG. 4: Effect of BO-112 different poly(I:C) formulations on patient-derived melanoma cells (SK-Mel 103 cell line). BO-112 is compared ex vivo to untreated cells (NT) and to cells treated with Poly-ICLC, LyoVec-LMW, or LyoVec-HMW, each formulation being tested at the concentrations that were determined according to complex weight but with a similar content of poly(I:C) molecules. (A) The cell viability data were generated using crystal violet assay method after a 48 hour treatment with each poly(I:C) formulation at 0.35 µg/ml concentration. (B) The expression of Interferon-alpha/beta (IFNa/b, in Arbitrary Units) was evaluated at 16 and 24 hours after treatment with each poly(I:C) formulation at 0.5 µg/ml concentration.
Figure 4:
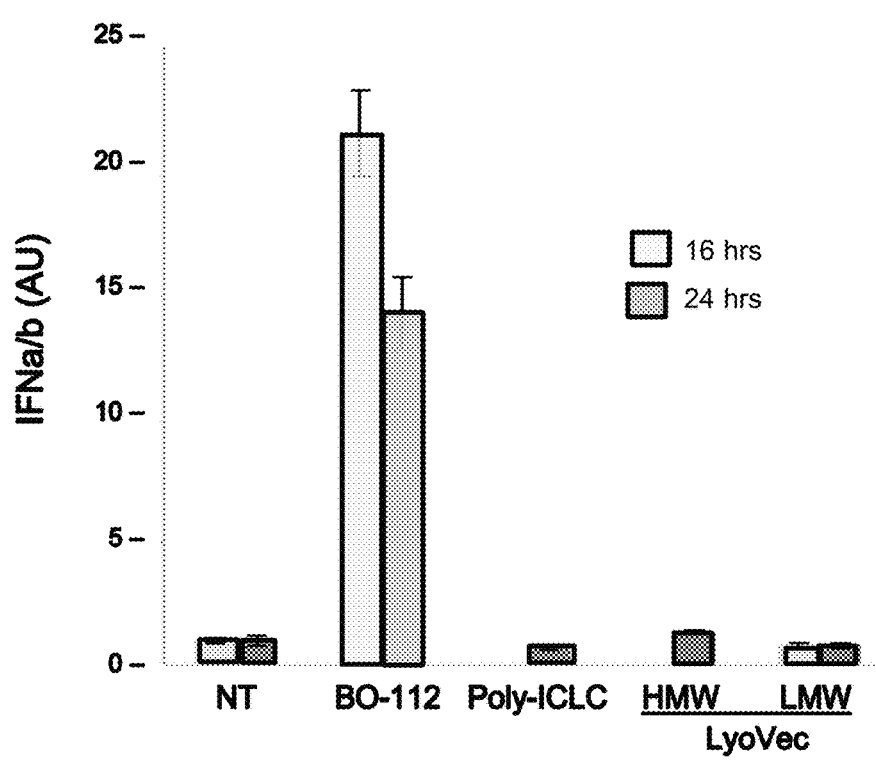
Figure 5:
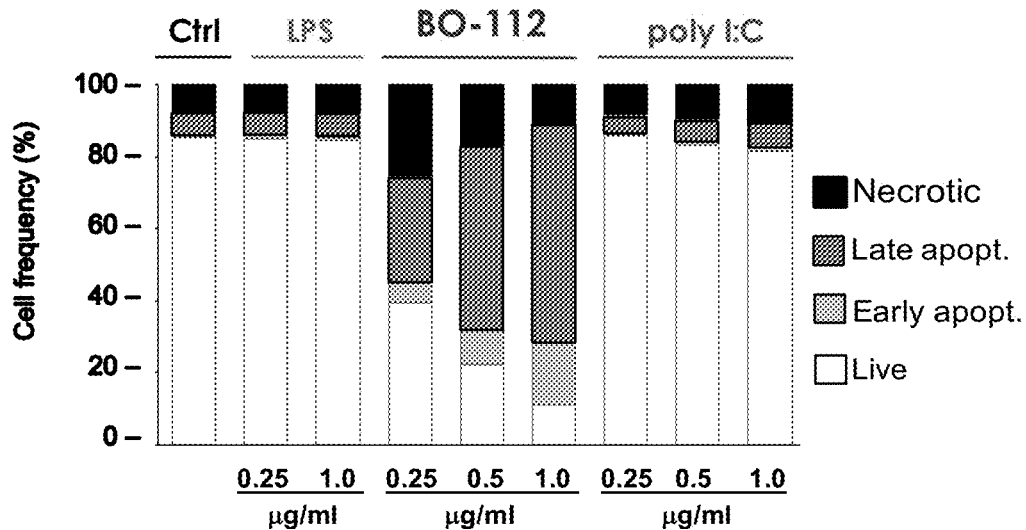
FIG. 5: Effect of BO-112, lipopolysaccaharides (LPS), and poly(I:C) preparation for producing BO-112 on different type of cell death and the expression of related markers. B16-F10-OVA (cells $10^5$ cells/well) were cultured alone (control) or with LPS, BO-112 or poly(I:C) molecules only (having the same size distribution of those incorporated in BO-112 formulations), at the indicated concentrations for 48 hours, measuring by flow cytometry the percentage of cells still viable or presenting combinations of markers related to early/late apoptosis, or necrosis (annexin V and 7ADD staining; A), or expressing specific markers of immunogenic cell death such as MHC-I, CD95 or Caireticulin, (B).
Figure 5:
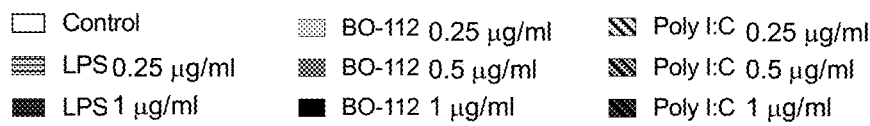
Figure 5:
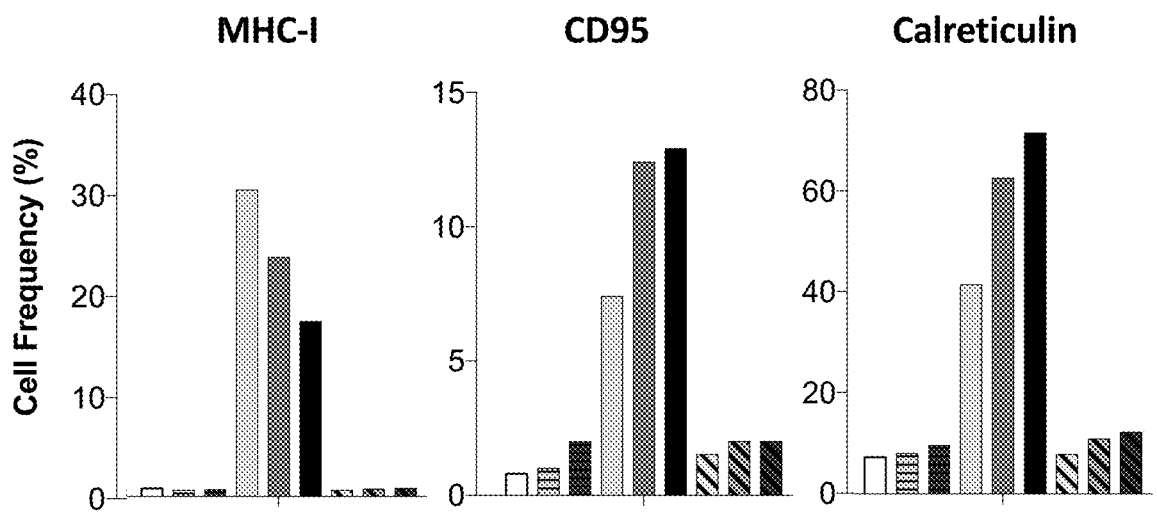

The observations described above were confirmed in a cell lins from a melanoma patient that have been exposed to BO-112 composition (when compared to other poly(I:C)-based formulations) not only specifically and more strongly reduced the viability of cancer cells but also induced Interferon alpha/beta production by such cells (FIG. 4). Moreover, the BO-112 composition promotes tumor cell death (apoptosis and necrosis) and enhances immunogenic cell death (ICD) to a much greater extent than LPS (a TLR4 agonist) or the corresponding poly(I:C) molecules (generally defined as TLR3 agonist) at comparable concentration (FIGS. 5A and B). This stronger, pro-apoptotic potency of BO-112 formulation, when compared to these TLR-specific agonists, has major implications for eliminating cancer cells but also for activating an effective anti-tumor immune response. Indeed, a significant increase in the expression levels of ICD markers, such as MHC-I, CD95 or Calreticulin, is observed after BO-112 stimulation (compared to untreated cells, LPS- or poly I:C-treated cells) confirming the strong potency of BO-112 formulation to induce anti-tumor immunity. Similar in vitro studies can be performed using tumor mouse models for in vivo studies and for guiding clinical development.

Figure 6:
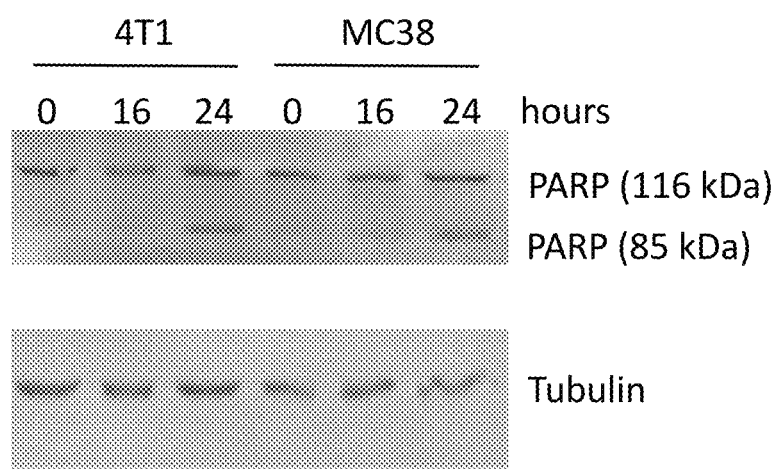
FIG. 6: Effect of BO-112 on activation of the enzyme Poly ADP ribose polymerase (PARP). 4T1 breast or MC38 colon cancer cells ($3 \times 10^6$) were cultured with BO-112 (0.5 µg/mL). Activation of PARP, an enzyme which is involved in DNA repair, genomic stability, and programmed cell death was evaluated at 0, 16 h and 24 h after BO-112 stimulation by Western Blotting analysis. It was analyzed the presence in the cell lysates of the complete 116 kDa PARP protein and the 85 kDa apoptosis-induced cleavage product; tubulin was included as control for loading equal protein amounts. Results show that BO-112 formulation promotes the activation of PARP enzyme in both MC38 and 4T1 cancer cells, providing evidence for use of BO-112 composition in combination with PARP inhibitor in patients where this latter type of drugs is poorly or not effective and may require being sensitized to (see also FIGS. 14B and 15B).

Similar cell-based approaches have been used for validating BO-11X, and BO-112 formulation in particular, that have been exposed to filtration and/or freezing, confirming that the cytotoxic effects are not only qualitatively and quantitatively maintained in BO-112 preparations after such processes but also for evaluating the enhanced expression of cell death markers and/or cancer antigens or targets specifically recognized by immune cells or cancer drugs. For instance, this approach can be used also for measuring the reduced or decreased expression (or degradation) of biological targets for cancer drugs such as cell surface markers and receptors, kinases, enzymes. For example, aside from immune checkpoint, the activity of enzymes that control DNA repair such as Poly [ADP-ribose] polymerases may be affected by the exposure of cells to BO-11X compositions, as it has been observed for PARP1 in cell lines and fresh tumor specimens, derived from autologous primary and metastatic head and neck squamous cell carcinoma where the role of TLR3 signaling in metastatic progression has been evaluated, observing significant apoptosis as measured by cleaved PARP in primary and metastatic tumor samples, as well as in related cell lines, after the exposure to poly(I:C) molecules (Umemura N. et al., 2012). FIG. 6 shows that PARR cleavage is also observed when BO-112 formulation is administered to 4T1 breast and MC38 colon cancer cell lines, indicating that BO-112 formulation can be used for improving the use of PARP inhibitors, whose clinical use Is limited by resistance mechanisms in patients (Lim J and Tan D, 2017). in combination therapies for expanding the therapeutic utility of PARP Inhibitors, as shown in previous figures for anti-PD1 or antiPD-L1.

More in depth analysis of these in vitro data for guiding clinical development can be performed using different preclinical models involving the production and the comparison of different BO-11X formulations, different administration regimens, and/or conditions associated to a disease such as cancer. In particular, additional studies may involve the determination on effect of the BO-11X formulations over the activity, expression, and/or concentration of mRNA and/or corresponding proteins in biological materials (such as blood or biopsies) and cells obtained from patients (being cancer cells, immune cells, or other cell type). The properties of BO-11X formulations may be evaluated in human cells (being primary tumor cells, cell lines, or genetically modified cells) when cultured in vitro, tested ex vivo, and/or when injected in mice, where more complex immunological mechanisms can be studied. The characterization of such activities, as well as of associated change in gene expression and potential mechanisms of actions, may allow defining optimized administration routes and regimens, combinations with other drugs, follow-up treatments, and/or patient populations applicable to BO-11X formulations, as summarized in Example 3.

Example 2: Functional Characterization of BO-11X Preparations in Animal Models

Materials & methods
BO-11X Formulations and Other Compounds
BO-112 formulations have been obtained as described in Example 1, and diluted with a 5% glucose PBS solution (vehicle; ref: BE14-516F, Lonza, France) into three different concentrations in accordance with a dosing amount per kilo bodyweight of the animal of respectively 0.05 mg/Kg, 0.5 mg/Kg and 2.5 mg/Kg.

Murine anti-PD-L1 antibody (InVivoPlus, clone 10F.9G2) was chosen as combination immunotherapy compound. Rat-IgG2b antibody (clone LTF-2, BioXCell) was used as isotype control. Each day of injection to mice, anti-PD-L1 and Rat-IgG2b (RIgG) antibodies were diluted with vehicle at final concentrations of 1.5 mg/ml.

Murine anti-CD4 (clone GK1.5) and anti-CD8α (clone 2.43), and rat-lgG2b (clone LTF-2) antibodies (all from BioXCell) were used for T cell depletion. Mice received three initial doses of anti-CD4 or anti-CD8α (300 µg/mouse), or Rat-IgG2b (100 µg/dose) antibodies, followed by maintenance doses of 100 µg/mouse.

Mouse Cell Lines
(B16-F10, skin melanoma, ATCC code CRL-6475, and B16-OVA derived from them; MC38, colon adenocarcinoma, Cellosaurus code CVCL_B288, Kerafast cat. no. ENH2O4; 4T1, breast cancer, ATCC code CRL-2539; were obtained from established collections at the ATCC or from the Centro de Investigación Médica Aplicada (Navarra, Spain) and, where possible, were subject to short tandem repeat (STR) profiling (GenePrint® 10 System) for cell line authentication. B16 cell lines that are insensitive to IFNs were obtained from Invivogen (B16-Blue™ IFN-γ cells, Cat.no. bb-ifng; B16-Blue™ IFNα/β cells, Cat. no. bb-ifntl) and maintained as indicated by manufacturer.

Animal Models for Human Cancers
Above-indicated cell lines were injected subcutaneously (s.c.) in the RIGHT flank ($5\times10^5$-$1\times10^{6^5}$ cells) of 8- to 10-week-old female C57BL/6 mice. For abscopal studies, a second s.c. injection ($3\times10^5$ cells) was performed in the LEFT flank (directly following the primary injection of tumor cells in the right flank, concomitant injection model). For re-challenge studies a second s.c. injection ($2.5$-$5\times10^5$ cells) was performed in the LEFT flank of mice that responded to BO-112 treatment and were free of tumors. Tumors were measured by caliper weekly until sacrificed and volume calculated (length×width2/2). Survival was evaluated by Kaplan-Meier analysis.

BO-112 Administration and Other Compounds
BO-112 treatment started when tumor volume was 80-100 mm³. BO-112 administration and vehicle was performed intratumorally via a single direct injection into the tumor mass of the RIGHT flank. BO-112 dose schedule (2 doses/week, 3 weeks). Anti-PD-L1 and Rat-IgG2b antibodies administration was performed intraperitoneally, started at the second dose of BO-11X and continued the same schedule as BO-112. Anti-CD4, anti-CD8α and Rat-IgG2b mAbs were administered intraperitoneally; an initial dose was injected one day before starting BO-112 administration, and continued along the experiment. The exact schedule of administration (BO-112 and other compounds) of every experiment is indicated in the figures.

Immune Response Studies
The implication of different T cell subsets in the BO-112 anti-tumor effect was investigated by T cell depletion experiments in the MC38 mouse tumor model. Anti-CD4 or anti-CD8α antibodies were administered systemically in MC38-tumor bearing mice starting before BO-112 treatment; dosage, administration and schedule of BO-112, anti-CD4 or anti-CD8α antibodies is described previously. Tumors were measured by caliper weekly until sacrificed and volume calculated (length×width2/2). T cell activation and priming induced by BO-112 therapy in vivo was evaluated 24 h after the second administration of BO-112. Tumors and draining lymph nodes were excised, tumors were digested (Collagenase/Dispase digestion medium) and filtered, all samples were processed to obtain a single cell suspension. A standard protocol for flow cytometry surface and intracellular stainings was performed, fluorochrome-labeled antibodies used: anti-CD4, -CD8, -CD45, -PD-I, -IFNγ, -CD137 (Biolegend). Antigen specific CD8+ T cells against OVA or Trp2 were analyzed (iTAg Tetramer/PE-H-2 Kb, BML international Corporation). Samples were acquired using a Gallios Cytometer (Beckman Coulter) and data were analyzed with Kaluza Flow Analysis Software (Beckman Coulter).

The death-inducing activity of BO-112 was tested in mouse cancer cells that do not respond to IFNs by an MTS assay (CellTiter 96® AQueous Non-Radioactive Cell Proliferation Assay, Promega). B16, B16-IFN-α/β (do not respond to IFN-γ) and B16-IFN-γ (do not respond to IFN-α/β) cells (5000 cells/well; 96 flat-well plates, 8 replicates per condition) were cultured with Poly(I:C) only (0.5 μg/mL), BO-112 formulation (0.5 μg/mL), or 2',3'-Cyclic GMP Sting Agonist (7 μg/mL; InvivoGen, San Diego, CA) for 24 hrs, 48 hrs, 72 hrs depending on the experiment, as described in the Figures. Absorbance (OD 492 nm) was measured in an ELISA reader. Dead cell % is referred to untreated cells (0%).

Results

The anti-cancer, in vivo efficacy of BO-112 formulations was investigated for in vivo in an immune competent mouse strain, implanted with mouse melanoma cells. Mice were treated either with a PBS solution or a BO-112 formulation at three different concentrations (0.05, 0.5, or 2.5 mg/kg, preferably administered intratumorally), in combination with a murine anti-PD-L1 antibody (preferably administered systemically) and compared to vehicle alone throughout 3 weeks (FIG. 7A). Anti-PD-L1 antibody in combination with the vehicle did not significantly increase survival when compared to vehicle alone. All three BO-112 formulations combinations tested with anti-PD-L1 (and possibly independently form such antibody) significantly increased survival of the mice compared to vehicle or anti-PD-L1 alone. Moreover, survival significantly increased in the combination of 2.5 mg/kg BO-112 formulation+anti-PD-L1 compared to the lower doses of BO-112 formulation (FIG. 7B). Indeed, BO-112 formulation administered alone clearly reduces tumor growth in this model (FIG. 7C-D). The effect of this combination was also tested in model for abscopal effects of intratumoral injections in a similar melanoma mouse model, in which the BO-112 formulation not only reduced the size of injected tumor mass but also the non-injected tumor mass, thus confirming both local and systemic anti-tumor effect of BO-112 formulation (FIG. 8). Anti-PD-L1 antibody is an important and validated anti-cancer drug, and mediator of an effective immune response against the cancer cells. Our experiment demonstrates that BO-11X complexes can be used in combination with other anti-cancer agents, and that the combination of BO-11X compounds with other anti-cancer agents such as anti-PD1 has superior potency to the anti-cancer agent alone, leading to significant increases in survival and anti-tumor efficacy. Moreover, the improvement in survival (or in immune memory cells, and more general systemic therapeutic responses) correlates with an increase in dose of BO-11X formulation to the combination, supporting that the added benefit in survival is mediated through the BO-11X formulation. This anti-cancer, in vivo efficacy of BO-112 formulation was confirmed, also in absence of anti-PD-L1 or of any other treatment, in both 4T1-based (FIG. 9) and MC38-based (FIG. 10) models for breast cancer and colorectal cancers, respectively. BO-112 reduced not only tumor growth in 4T1 breast carcinoma model but also improved mice survival in MC38 colon carcinoma model, in the latter case also by using two different approaches (with or without a re-challenge with cancer cells; FIGS. 10 and 11).

Thus, BO-11X formulations can be used (alone or in combination with other anti-cancer agents, such as antibodies, immunotherapy, or chemotherapy, that can be administered using the same or a different route) in treating melanoma and other cancer indications, in particular those allowing peritumoral or intratumoral injection such as in pancreatic, endometrial, ovarian, renal, hepatocellular or colorectal cancer. Moreover, B0112 induces systemic immunity by promoting immune cell memory allowing its use as single therapeutic agent.

At this scope, the identification of specific biological pathways and mechanisms of action may guide the most appropriate dosages, regimens, combination with other drugs or therapies, and indications for BO-11X formulations, as shown for combined effects of immunomodulatory monoclonal antibodies targeting PD-1, CTLA4, PD-L1, or CD137 and poly(I:C) preparations that enhance the activities of dendritic cells (Sanchez-Paulete A R et al., 2015). To this end, Duewell P et al., 2015 discloses an alternative animal model of disease that may be used for testing the composition of the present invention for the immunotherapy of pancreatic carcinoma.

The therapeutic effect on tumor growth (locally and/or in distal locations) and the anti-tumor immune response of BO-11X formulations can be measured by performing In vivo studies on Intratumoral (i.t.) administration across at a range of concentration for poly(I:C) molecules (such as 0.5, 1, 2, 2.5, or 5 mg/kg) to evaluate how such treatment improves mouse survival in a relevant model (such as a mouse melanoma, breast cancer, ovarian cancer, leiomyosarcoma, endometrial cancer, or pancreatic cancer models), with or without co-administering a further drug or a vaccine. At the same time, dose-response studies about specific biological activities induced by BO-11X treatment can be evaluated in parallel ex vivo, using human or animal samples at the level of apoptosis induction (by Caspase-related Glow), immunogenic cell death induction (for example MHC-I, calreticulin, CD95, or HMGB1 expression), chemokine/cytokine secretion in biological fluid (for example, secretion of IL-6 and IP-10), in vitro cellular activation and/or proliferation (for example, associated to CD40, CD86, CD69 upregulation on relevant cell types). These studies can be performed using cells that are directly involved in disease (e.g. tumor cell, epithelial cell, endothelial or epithelial cells) or cells indirectly involved since performing some immune or immunoregulatory activities (e.g. human peripheral blood mononuclear cells, NK cells, B cells, CD4+/CD8+ T cells, dendritic cells) either within tumors, in lymphoid organs or in blood. These studies may also involve the effect of BO-11X treatment using different routes of administration, such as sub-cutaneous or intra-muscular administration, in order to establish different schedules for BO-11X clinical uses, as well BO-11X suitability as adjuvant in cancer-related and/or infection-related vaccinations.

These studies can be further associated to the identification to molecules that may be used as biomarkers to predict response to BO-11X (or lack thereof) in order to stratify disease stages and/or patients' populations for BO-11X treatment. In particular, the analysis of BO-11X activities may be performed by comparing the qualitative and/or quantitative feature of immune cells (such as NK cells, B cells, CD4+/CD8+ T cells) and the tumor growth kinetics in animal models where changes in specific cell markers and (sub-)populations can be measured also when specific cell types are either depleted or activated in combination with BO-11X administration (for example, by co-administering T cell depleting or activating antibodies, viral, bacterial or cancer antigens, cell-based treatments such as adoptive T-cell therapies, or compounds with adjuvant properties).

The involvement of specific immune cells can be explored in cancer animal models similar to those previously described, where the treatment with BO-112 formulation is evaluated with respect to the depletion of immune cells or presence of specific immune cell populations within tumors following the administration of BO-112 formulation. Depletion of CD4positive T cells improves the effect of BO-112 formulation, suggesting the clinical potential for combination therapies of BO-112 with drugs that target CD4 Tregs (FIGS. 12 A and B). Depletion of CD8positive T cells appears as decreasing the anti-tumor effect of BO-112 formulation on mouse tumor models confirming the implication of the adaptive immune response in the BO-112 anti-tumor mediated effect/. Moreover, the representation of specific cell populations among Tumor Infiltrating Lymphocytes is modified by intratumoral injection of BO-112 formulation, with the significant increase not only of CD45/CD8positive T cells, but also of positivity for CD137, OVA and Trp2 tetramers, PD-1, and interferon gamma expression in CD8positive cells, these effects partially confirmed in CD4positive cells; in the same model specific CD8+ T cells against the endogenous tumor antigen Trp2 are also increased in the tumor draining lymph node (FIGS. 12 C and D).

These data confirm that BO-112 formulation promotes the adaptive immune response against the tumor and is able to induce systemic immunity. The potent effect of BO-112 to induce tumor cell death and promote T cell infiltration and activation provides evidence for clinical combination with drugs that target complementary mechanisms of tumor progression such as immune suppression (Chen D S and Mellman I, 2013). Activation of CD4+ and CD8+ T cells in the tumor after BO-112 therapy demonstrate the activation of IFN signaling pathway. IFNγ plays a pivotal role in anti-tumor systemic and local immunity but also induces PD-L1 expression in cancer cells, a mechanism described to impair local tumor immunity and drive immunosuppression (Abiko K et al., 2015). BO-112 intratumoral administration in different mouse tumor models induces PD-L1 expression in tumor cells, what supports the rational for combination therapy of BO-112 with PD-1/PD-L1 targeted drugs. Promising combinations include drugs that target other immune check point inhibitors, in order to unblock the immune suppression induced by the tumor cells and/or the tumor microenvironment such as CTLA4, Tim-3, LAG3 or IDO.

The potent and direct cytotoxic effect of BO-112 formulation on tumor cells is also detected in cells that do not respond to IFNs (having relevant clinical implications for patient selection and BO-112 treatment. BO-112 formulation appears triggering tumor cell death also independently from the capability of cancer cells to respond to interferons (FIG. 13). Loss of function mutations in IFN-gamma receptor signaling or antigen presenting machinery mediate some cases of primary resistance and acquired resistance to PD-1 blockade therapy (Zaretsky J et al., 2016). Activation of the RIGI/MDA5 pathway by BO-112 in tumor cells represents an strategy to overcome the IFN-γ resistance and might resensitize tumors to autologous CD8+ T cells therapies. Early chromosomal aberrations could predispose to acquired IFNγ resistance and T cell resistance in certain tumor types, therefore screening of patient metastases for chromosomal aberration and gene mutations prior to immunotherapy to define the risk of resistance development may be useful for the selection of patients that will benefit from BO-112 therapy.

The literature provides several evidences human tissue specimens on cells within tumors (including melanoma, breast invasive carcinoma, prostate adenocarcinoma, lung adenocarcinoma, and colorectal adenocarcinoma) harbour alterations in JAK1 and JAK2, including loss-of-function alterations in either JAK1 or JAK2 that would putatively diminish JAK1 or JAK2 signaling (homodeletions, truncating mutations, or gene or protein downregulation). These evidences may be useful for the selection of patients that, in view of their mutational burden with tumor, would particularly benefit from BO-112 therapy.

Example 3: Clinical Studies Using BO-112 Formulations

The pre-clinical studies involving the administration of BO-112 in animal models can be used as basis for establishing clinical studies in which BO-112 is administered (for example, through intratumoral delivery) seeking a safer and more focused enhancement of local and systemic antitumor effects. The potential of BO-112 intratumoral administration as an immune-modulatory treatment, as well as its toxicity/safety profile, is being analysed in this first in human, proof of concept, clinical trial (NCT02828098). Patients with cancer lesions which are accessible for intratumoral injection, such as malignant solid tumors and palpable cutaneous/sub-cutaneous or lymph node metastases (>1 cm) and from whom biopsies can be obtained, are treated with BO-112 using intra-tumoral injections at different dose levels (0.6 mg-1 mg of poly(I:C) content in each dose, 1-3 doses with one dose/week) starting from BO-112 preparations containing poly(I:C) molecules at a concentration of at least >0.5-mg/mL. The injected lesions are biopsied before treatment is started and at 7-14 days after the last dose, or alternatively after 6 weeks, for example. The patients are evaluated in parallel with respect to signs of clinical relevance and innate or adaptive immune system response and signaling pathways. BO-112 pharmacokinetics and circulating cytokines such type I Interferon, TNF-alpha, and IL-6 are also evaluated in plasma. Preliminary results show that patients did not experience relevant toxicity with the exception of two episodes of thrombocytopenia, that were recovered without treatment. BO-112 was not detectable in bloodstream following intratumoral delivery. BO-112 has determined both statistically and therapeutically relevant changes in all patients for at least one of the following tumor-relevant criteria: size of injected tumor, appearance or not of metastasis, apoptosis and necrosis of cancer cells (demonstrating immunogenic cell death triggered in tumors by BO-112 formulations), increase of CD4-positive tumor infiltrating T cells, increase of CD8-positive tumor infiltrating T cells, increase in circulating immune cells (including NK cells, dendritic cells, monocytes, and/or T regulatory cells, total or specific sub-populations presenting specific markers such as CD16 or PD-1).

When the BO-11X formulation (or a BO-11Xm formulation) is clinically administered by intratumoral injection, apoptosis and/or necrosis is observed in the tumor, possibly as a results of the direct antitumoral effects combined with activation of anti-tumor responses by other cells resident in the tumor (e.g. by promoting the presentation of tumor antigens to dendritic cells). and cascade may also lead to recruitment and/or activation of immune cells, in particular CD4+ and CD8+ T cells into the tumor mass promoting an immune effect against the tumor, contributing to the cytotoxic effect of BO-11X. Systemic changes in immune cell populations such as CD8, CD4, CD4 Treg, NK T, NK, CD16+ monocytes, or DCs, are also triggered that could be capable of mounting both primary and memory anti-tumoral responses.

The BO-11X formulations (or a BO-11Xm formulation) can be also administered as a single agent or in combination with other anti-cancer therapies such as checkpoint inhibitors or other immuno-oncology agents (in addition or not to chemotherapy and radiotherapy) given via other routes of administration and with different frequency in regimens that involve not only subsequent intra-tumoral injections but also by including alternative administration routes such as by sub-cutaneous or intramuscular administration, within one or more cycles of treatments (FIGS. 14A and 14B, also including anti-CTLA4, anti-PD-1 or anti-PD-L1 concurrent therapies). A cycle of BO-11X treatment can be established as a pre-defined number of intra-tumoral injections in the same or in different tumor lesions (from one up to four or more consecutive ones over one, two, three, four or more weeks), In a second part of the first-in-human clinical trial referred to above, patients who are not responding to treatment with an anti-PD1 antibody are given multiple dose fo BO-112 in addton to continued treatment with the anti-PD1 antibody (see FIG. 14B). Clinical response to treatment, as measured by overall tumor burden based on imaging techniques, as well as biological activity as assessed in tumor tissue and circulating immune cells are evaluated in the trial (see FIG. 15). that can be followed by a number of intra-muscular or sub-cutaneous injections (from one up to seven or more consecutive ones over one, four, seven, fifteen or more weeks), repeating such cycle with the same regimen (or by extending the interval between injections) depending of patient responses. The BO-11X formulations in these intra-muscular or sub-cutaneous injections will possibly be diluted before administration in order to provide lower doses of poly(I:C) molecules, when compared to intra-tumoral injections (e.g. 50%, 25%, 10%, 5%, 1% of the dose that is intra-tumorally injected) but they may still allow sustaining the initial therapeutic and/or immunomodulating effect of intra-tumoral injections. In addition to the parameters mentioned above, clinical response may also be evaluated through physical examination, CT-scan, MRI-scan or other imaging techniques for evaluating tumor burden.

Alternatively, the BO-11X formulations (or BO-11Xm formulations) may be administered ex vivo, using cells that are isolated from a patient, in particular for improving maturation, efficacy, and/or activation of specific immune cells, such as Dendritic Cells (FIG. 14C). This approach may be applied for in vitro maturation of dendritic cells, as described in the literature for neoantigen-, adoptive T cell-, cell lysate-, cancer-, gynaecological diseases, and/or infection-related uses (Vanderlocht J et al., 2010; Gallois A and Bhardwaj N, 2013; Da Silva D M et al., 2015; Fritsch E F et al., 2014; Gonzalez F E et al., 2014; Tai L H et al. 2013; Hammerich L et al., 2015; Hervas-Stubbs S et al., 2012; Ochoa M C et al., 2017; Osada T et al., 2015; Perica K et al, 2015). Also in this case, the BO-11X formulations in these in vitro/ex vivo methods will be possibly diluted before administration in order to provide lower doses of poly(I:C) molecules, when compared to intra-tumoral injections (e.g. 50%, 25%, 10%, 5%, 1% of the dose that is intra-tumorally injected, but possibly within the range of doses and concentration that are used for validating BO-11X formulation in cell-based models, as disclosed in Example 1). These dosages may still allow providing the therapeutic and/or immunomodulating effect that is appropriate for such therapeutic approaches, with or without later applying a cycle of BO-11X treatments in the same patient.

By using any of the routes of administrations and regimen listed above, BO-11X formulations (or BO-11Xm formulations, such as BO-112 formulations) can be validated taking into account one or more combined criteria that are measured in the patients using biopsies, blood samples, and/or other clinical criteria (see above and FIG. 15A). Thus, aside from direct evaluation of tumor size and metastasis, the therapeutic efficacy of BO-11X formulations can be determined in methods wherein at least one of the following three general criteria are evaluated: direct cytotoxicity on cancer cells (apoptosis and necrosis of cancer cells), increase of tumor infiltrating, immune cells (such as CD4-positive and/or CD8-positive tumor infiltrating T cells), increase in immune cells that circulates in blood (total populations or specific sub-populations of lymphocytes, NK cells, monocytes, dendritic cells, macrophages, B cells, etc.), and/or presenting some differential expression pre-versus post-treatment only in either responding or non-responding patients (as determined by RNA sequencing or other mass sequencing approach).

This validation process may also involve follow-up at the molecular level by, for example, screening the mRNA and/or protein expression of specific sets of proteins such that not only the efficacy of the treatment can be confirmed but also whether other treatment (previously found ineffective) can be applied since BO-11X (or BO-11Xm) administration has enhanced the patient responsiveness. Examples of such signatures and alternative regimes that can be identified in BO-11X or BO-11Xm treated patients, are available in the literature for instance with respect to Interferon expression and/or other markers to be identified and acquired resistance to PD-1-based therapies for potential rescue of patients (Zaretsky J et al., 2016; Masucci G et al., 2016). Thus, safety, efficacy, and immune-biological data will provide the rationale for choosing the BO-11X (or BO-11Xm) dosage for future clinical trials, using BO-11X formulations such as BO-112 alone and/or in combination with other drugs, standard-of-care protocols, or immunotherapies that can provide further therapeutic benefits (FIG. 15B).

The therapeutic efficacy of BO-112 formulation is under clinical evaluation, with two initial examples that further illustrate the relevant clinical effect (FIGS. 16 and 17). Thesepreliminary results confirms the efficacy of BO-112 in reducing cancer lesions, demonstrating safety and the intended biological effect, with or without concurrent administration of anti-CTLA4, anti-PD1, and/or anti-PD-L1 antibodies, with the potential effect to address cancer patients refractory to checkpoint therapy and inducing immunogenic cell death and anti-tumor immunity. Moreover, these preliminary results show that patients did not experience clinically relevant toxicity with the exception of two cases of thrombocytopenia, both of which recovered (one with transfusion of platelets the other without treatment). BO-112 was not detectable in the bloodstream following intratumoral delivery. BO-112 has demonstrated therapeutically relevant changes in all patients for at least one of the following tumor-relevant criteria: size of injected tumor, apoptosis and necrosis of cancer cells, increase of CD4-positive tumor infiltrating T cells, increase of CD8-positive tumor infiltrating T cells, increase in circulating immune cells (including NK cells, dendritic cells, monocytes, and/or T regulatory cells, total or specific sub-populations presenting specific markers such as CD16 or PD-1).

Example 4: Evaluation of Biological Effects Due to the Administration of BO-112 Formulations in Patients Materials & Methods The pre- and post-treatment biopsies from the injected metastatic lesion are obtained, in order to analyse apoptosis, necrosis, immune infiltrate and inflammatory gene RNA expression signatures (for example, using the Nanostring platform and specific panels of human genes such as those listed by the manufacturer as PanCancer Pathways, PanCancer immune Profiling, or PanCancer Progression Panels). Pharmacokinetics, serum cytokines and circulating immune cells are sequentially studied in pre- and post-treatment blood samples.

Using the nSolver Analysis Software (NanoString, Inc.), counts were first normalized to the geometric mean of the negative control spiked into the assay to correct for experimental variability. Then, the geometric mean was used to compute the normalization factor of the positive control and, finally, normalized to housekeeping genes built into the Human Immunology panel. The detailed normalization analysis guidelines can be found on the NanoString Technologies website [http://www.NanoStrinq.com]. The normalized data were measured as counts. Normalized data of the nSolver procedure were log-transformed (with base 2) for the 750 endogenous genes. nCounter chips data for the 12 patients were obtained pre- and post-treatment. The differential expressions were evaluated using a paired t-test for each gene. The design matrix used was:

$$\begin{pmatrix} pre_1 \\ post_1 \\ pre_2 \\ post_2 \\ pre_3 \\ post_3 \\ \ldots \\ \ldots \\ \ldots \\ pre_{12} \\ post_{12} \end{pmatrix} = \begin{pmatrix} -1 & 1 & 0 & 0 & \ldots & 0 \\ 1 & 1 & 0 & 0 & \ldots & 0 \\ -1 & 0 & 1 & 0 & \ldots & 0 \\ 1 & 0 & 1 & 0 & \ldots & 0 \\ -1 & 0 & 0 & 1 & \ldots & 0 \\ 1 & 0 & 0 & 1 & \ldots & 0 \\ \ldots & \ldots & \ldots & \ldots & & \ldots \\ -1 & 0 & 0 & 0 & \ldots & 1 \\ 1 & 0 & 0 & 0 & \ldots & 1 \end{pmatrix} \begin{pmatrix} \beta_0 \\ \beta_1 \\ \beta_2 \\ \beta_3 \\ \ldots \\ \beta_{12} \end{pmatrix}$$

Where $\beta_0$ is the differential expression between pre- and post-treatment, and $\beta_1$ to $\beta_{13}$.Gene modified to higher expression after treatment showed positive values of fold change. A linear model for nCounter data was constructed using the limma package. The p-values were corrected for multiple comparisons using the Benjamini and Hochberg's method. The genes with a significance value of p<0.05 were clustered. All gene expression analyses were performed in R.

Results

Initially, the gene expression studies using cells obtained from BO-112 treated patients has allowed identifiing the down- or up-regulation of a limited number of genes, as summarized in table I.

TABLE I

| Gene Symbol | Uniprot code | Gene Description (regulation after BO-112 treatment) |
|---|---|---|
| CYFIP2 | Q96F07 | cytoplasmic FMR1 interacting protein 2 (down-regulated) |
| LRRN3 | Q9H3W5 | leucine rich repeat neuronal 3 (down-regulated) |
| IL8_2 | ???? | interleukin 8 (up-regulated) |
| IRAK2 | O43187 | interleukin-1 receptor-associated kinase 2(up-regulated) |
| SLC11A1 | P49279 | Solute carrier family 11 (proton-coupled divalent metal ion transporters), member 1, natural resistance-associated macrophage protein 1 (up-regulated) |
| CD36 | P16671 | CD36 molecule (thrombospondin receptor) (up-regulated) |
| BTK | Q06187 | Bruton agammaglobulinemia tyrosine kinase (up-regulated) |
| LY96 | Q9Y6Y9 | Lymphocyte antigen 96 (up-regulated) |
| CD163 | Q86VB7 | CD163 molecule (up-regulated) |
| CCL7 | P80098 | Chemokine (C-C motif) ligand 7 (up-regulated) |
| IFI35 | P80217 | Interferon-induced protein 35 (up-regulated) |
| CXCL1 | P09341 | Chemokine (C-X-C motif) ligand 1 (melanoma growth stimulating activity, alpha) (up-regulated) |
| CTSL | P07711 | cathepsin L1 (up-regulated) |
| TLR2 | O60603 | toll-like receptor 2, CD282 (up-regulated) |
| CCL3 | P10147 | chemokine (C-C motif) ligand 3 (up-regulated) |
| IL8 | P10145 | interleukin 8 (up-regulated) |
| LAIR2 | Q6ISS4 | Leukocyte-associated immunoglobulin-like receptor 2, CD306 (up-regulated) |
| OAS3 | Q9Y6K5 | 2'-5'-oligoadenylate synthetase 3, 100 kDa (up-regulated) |
| IL1R2 | P27930 | interleukin 1 receptor, type II, CD121b (up-regulated) |
| IL10 | P22301 | interleukin 10 (up-regulated) |
| CREB5 | Q02930 | cAMP responsive element binding protein 5 (up-regulated) |
| MARCO | Q9UEW3 | macrophage receptor with collagenous structure (up-regulated) |
| MSR1 | P21757 | macrophage scavenger receptor 1, CD205 (up-regulated) |

The genes are selected present (log 2) fold change, p-value and adjusted p-value. From this analysis, 23 genes were found differentially expressed between pre- and post-treatment (p-value<0.05) within tumors (thus incuding potentially both cancer cells and infiltrating immune cells). The genes listed in the above Table I may associated to one or more of the GO (Gene Ontology) classes that are associated to the modulation (but preferably activation or increase) of the frequency, rate or extent of an immune response or defense (against a present or potential internal and/or invasive threat), general immunological and/or inflammatory processes, or other response to a organic, inorganic, or biological agent. Such GO classes include those having the systematic names: M14329, M11976, M10574, M13496, M12904, M13657, M12866, M10700, M16728, and M16306. In particular, three genes (CCL7, MARCO, MSR1) are related specifically to macrophages, one (OAS3) to activated DC, and one (LAIR2) to Th2 T cells. Two further genes (CD163, CD36) correspond to receptors involved in phagocytosis.

Alternatively, these genes may be analyzed on the basis of their protein localization and/or enzymatic activity. In a first group of up-regulated genes, the corresponding protein is an enzyme whose action can be inhibited by small molecules, these chemical having in many cases therapeutic properties by altering an immune response and/or response against cancer, associated or not to TLR3. For example, IRAK2 is a mediator of TLR3 signaling (Jain A et al., 2014), OAS3 is an interferon-induced dsRNA-activated enzyme which plays a critical role in cellular innate response, while cathepsin L1 and BTK are both target of anticancer and/or immunomodulatory compounds (Feng M et al., 2015; Molina-Cerrillo J et al., 2017; Ping L et al., 2017; Li Y Y et al., 2017; Sudhan D and Siemann D, 2015). In a second group of up-regulated genes (MSR1, MARCO, LAIR2, TLR2, CD163, CD36, SLC11A1, LRRN3), the corresponding protein is a cell surface receptor whose action can be activated (or inhibited) by various agents (antibodies or small molecules), these compounds having, in many cases, therapeutic properties. In a third group of up-regulated genes (IL10, IL8, CCL3, CCL7, CXCL1, LY96), the corresponding protein is a secreted protein whose action or interaction with a cell surface receptor can be inhibited, by various agents (antibodies or small molecules), also these compounds having, in many cases, therapeutic properties.

Using these categorization schemes and then testing appropriate antibodies, inhibitors or other commercially available products on cell lines, tissue samples or other biological materials, it is possible to define how BO-11X administration may affect by immune response and/or response against cancer by affecting set(s) of genes, associated or not to TLR3-related activities, immune cells, and/or response against cancer. The approach described above may lead to a series of further embodiments of the inventions wherein a BO-11X formulation (including a BO-11Xm formulation) is used in methods for treating a patient suffering from a disease (such as cancer) and/or preventing a disease (such as cancer or an infection) after determining the combined presence (and/or absence) of expression at the RNA and/or protein level for one or more genes in cells or tissues of the patient (such as a tumor, a blood sample, or a blood fraction), post- or pre-treatment with such a formulation. These methods may allow therefore defining a gene expression signature that is associated to:

(i) the therapeutically effective amount of a BO-11X formulation (or a BO-11Xm formulation);

(ii) the therapeutically relevant biomarker(s) that predicts that a subject may have an anti-tumor or anti-infective response after the treatment with a BO-11X formulation (or a BO-11Xm formulation):

(iii) the therapeutically effective amount of a BO-11X formulation (or BO-11Xm formulation) that may allow a subject responding to the treatment with a compound after the treatment with BO-11X formulation (or BO-11Xm formulation); and/or (iv) The therapeutically relevant biomarker(s) that predicts that a subject may respond to the treatment with a compound after the treatment with a BO-11X formulation (or a BO-11Xm formulation).

Thus, any of the genes of Table I can be used for the uses and methods as summarized in (i)-(iv) above, using the means for detecting/measuring the RNA and/or protein expression of any of these genes that are commercially available and applicable in common technologies such as RT-PCR or antibody-based methods). In particular, the coordinated up- and down regulation of selected (sets of) genes of Table I can be used for defining the biological response to BO-11X (and in particular BO-112) when therapeutically administered, and associated to the modulation of TLR3-mediated activities, interferon induction, and/or immune response, in patients presenting a specific disease, and in particular specific cancer-related indications, clinical stages, and/or combination with other drugs. In addition to the products applicable to the technologies listed above (such as nucleic acid probes or antibodies), the biological activity of such genes is often well defined, with a variety of commercially and technically agents that are available for testing appropriately the potential interaction with the administration of a BO-11X formulation, such as BO-112.

Moreover, further therapeutic agents that are available for targeting proteins whose expression is affected by the treatment with a BO-11X formulation (or BO-11Xm formulation). Drugs targeting any of the aforementioned genes might be advantageously used in combination with BO-11X formulations by administering them either within the same composition or in distinct compositions.

REFERENCES

Abiko K et al., 2015. Br J Cancer; 112:1501-9.
Ammi R et al., 2015. Pharmacol. Ther.; 146:1 20-31.
Amos S M et al., 2011. Cancer Immunol. Immunother.; 60: 671-83.
Ayers M et al. 2017. J Clin lnvest.; 127(8):2930-2940.
Bald T et al., 2014. Cancer Discov.; 4: 674-87.
Bhoopathi P et al., 2014. Cancer Res.; 74: 6224-35.
Bilensoy E, 2010. Expert Opin. Drug Deilv.; 7: 795-809.
Budczies J et al., 2017. Genes Chromosomes Cancer; 56(8): 651-659.
Chen D S and Meliman I, 2013. Immunity; 25; 39:1-10
Chen L et al., 2013. Int. J. Nanomed.; 8:137-145.
Chiba Y et al., 2013. PLoSOne.; 8: e76159.
Cho K. et al., 2016, Immunobiology. 222(2):394-398 (Epub 2016 Aug. 31).
Cobaleda-Siles M et al., 2014. Small.; 10: 5054-67.
Da Silva D M et al., 2015. Papillomavirus Res. 1; 1:12-21
Duewell P et al., 2015., Oncolmmunol.; 4(10): e1029698.
Ewel C et al., 1992. Cancer Res.; 52: 3005-10.
Feng M et al., 2015. Proc Natl Acad Sci USA.; 112(7):2145-50
Fritsch E F et al., 2014. Oncoimmunology. 25; 3:e29311
Fujimura T et al., 2006. Eur. J. Immunol.; 36: 3371-80.
Gallois A and Bhardwaj N, 2013. Front Immunol. 10; 4:436.
Galluzzi L et al., 2014. Oncotarget; 5: 12472-508.
Garcia-Pascual C and Gomez R, 2013. J. Endometr.; 5(suppl. 1):S13 (SP-04).
Germershaus 0 and Nultsch K, 2015. Asi J Pharm Sci. 10: 159-175.
Gong J et al. 2017. J Natl Compr Canc Netw.; 15(2):142-147.
Gonzalez F E et al., 2014. Hum Vaccin Immunother. 10(11): 3261-9.
Gupta S et al. 2016. Tumor Biol. 37: 12089-12102.
Hafner A et al., 2013. Advanced Drug Delivery Rev.; 65 (10): 1386-1399.
Hammerich L et al., 2015. Mol Oncol. 9(10):1966-81.
Hervas-Stubbs S et al., 2012. J. Immunol. 189(7):3299-310
Ho V et al., 2015. Oncotarget. 6: 27252-27266).
Islam Metal., 2014. Journal of Controlled Release; 193: 74-89.
Jain A et al., 2014. Front Immunol.; 17; 5:553.
Kabilova T et al., 2014. BMC Cancer.; 14: 338.
Keir M et al., 2008. Annu. Rev. Immunol.; 26: 677-704.
Kübler K et al., 2011. Eur. J. Immunol.; 41: 3028-39.
Kurosaki T et al., 2009. Biomaterials, 30: 2846-2853.
Le U et al., 2008. Canc. Biol. Ther.; 7: 440-447.
Le U et al., 2009. Radiother. Oncol.; 90: 273-279.
Levitzki A, 2012. Front. Oncol.; 2: 4.
Li Y Y et al., 2017. Expert Opin Ther Pat.; 27: 643-656.
Lim J and Tan D, 2017. Cancers (Basel; 9(8). pii:E109.
Ling H, 2016. Adv Exp Med Biol.; 937:229-37.

Masucci G et al., 2016. J Immunother Cancer. 4: 76.
Matijević T et al., 2011. Chemotherapy; 57: 460-7.
McBain S et al., 2007. J. Mater. Chem.; 17: 2561-2565.
Molina-Cerrillo J et al., 2017. Cancer Treat Rev.; 58:41-50.
Nagato T and Cells E, 2014. Oncoimmunology; 3: e28440.
Ochoa M C et al., 2017. Immunol Cell Biol. 95(4):347-355.
Ohashi T et al., 2013. Int. J. Cancer; 133: 1107-18.
Osada T et al., 2015. J Immunother. 38(4):155-64
Palchetti S et al., 2013. RSC Adv.; 3: 24597-24604.
Perica K et al, 2015. Rambam Maimonides Med J. 6(1): e0004.
Perrot I et al., 2010. J. Immunol. 185:2080-2088.
Ping L et al., 2017. Oncotarget; 8(24):39218-39229.
Pozuelo-Rubio M et al., 2014. Nano-Oncologicals in Adv. Del. Sci. Tech., Springer, pp. 453-470.
Saheki A et al., 2011. Int. J. Pharm.; 406: 117-21.
Sajadian A et al., 2014. Arch. Virol.; 159: 1951-1960.
Sanchez-Paulete A R et al., 2015. Cancer Discov.; pii: CD-15-0510.
Schaffert D et al., 2011. Pharm. Res., 28: 731-741.
Shabani M et al., 2010. Avicenna J. Med. Biotech.; 2: 123-130.
Shin D S et al., 2017. Cancer Discov.; 7(2):188-201.
Storz U, 2011. MAbs. 3: 310-7.
Sudhan D and Siemann D, 2015. Pharmacol Ther.; 155:105-16.
Szabo A et al., 2012. Melanoma Res.; 22: 351-361.
Tai L H et al. 2013, Clin Cancer Res. 19:5104-15.
Tan S et al. 2016. Protein Cell; 7(12):866-877.
Taura M et al., 2010. Cancer Sci.; 101: 1610-7.
Tormo D et al., 2009. Cancer Cell; 16: 103-114.
Tutin-Moeavin I et al., 2015. Org & Biomol Chem. 13: 9005-9011.
Umemura N. et al., 2012. Cancer Res. 72: 45-55.
Vacchelli E et al., 2013. Oncoimmunology; 2: e25396, e23510, e25595.
Van der Jeught K et al., 2015. Oncotarget; 6: 1359-81.
Vanderlocht J et al., 2010. Int J Immunopathol Pharmacol.; 23(1):35-50.
Vega-Letter A et al., 2016. Stem Cell Res. & Ther. 7:150
Yoshino H and Kashiwakura I, 2013. Blood; 122: 4721.
Yu L et al., 2016. Immunol Cell Biol. 94:875-885.
Zaretsky J et al., 2016. N Engl J Med. 375:819-829
Zhang Y et al., 2014.Cancer Lett. 355: 76-84.
Zhou Y et al., 2013. Innate lmmun.; 19: 184-192.

The invention claimed is:

1. A method for preparing an aqueous composition comprising one or more particles wherein:
(a) each particle comprises a complex of at least one double-stranded polyribonucleotide, or a salt or solvate thereof, and at least one water-soluble, linear polyethyleneimine, or a salt and/or solvate thereof, wherein
(i) the double-stranded polyribonucleotide is polyinosinic-polycytidylic acid [poly(I:C)], or a salt or solvate thereof, wherein
at least 40% of the poly(I:C) have at least 850 base pairs, and
at least 50% of poly(I:C) have between 400 and 5000 base pairs; and
between 5% and 60% of poly(I:C) have less than 400 base pairs;
between 15% and 30% of poly(I:C) have between 400 and 850 base pairs,
between 10% and 70% of poly(I:C) have between 850 and 5000 base pairs;
between 0% and 10% of poly(I:C) have more than 5000 base pairs, and
(ii) the average molecular weight of the water-soluble, linear polyethyleneimine is between 17 and 23 kDa and has a polydispersity index of <1.5;
(b) at least 90% of the particles have a mono-modal diameter distribution of below 300 nm;
(c) the one or more particles each have a z-average diameter of 80+/−20 nm measured according to ISO standard 22412:2017, and each particle diameter has a polydispersity index between 0.1 and 0.6;
(d) the poly(I:C) concentration is at least 0.5 mg/mL;
(e) the composition has a pH of between 3.0+/−0.2 and an osmolality of between 300 and 310 mOsm/kg; and
(f) the composition has a zeta potential between 35 mV and 50 mV measured according to ISO standard 13099-2:2012,
wherein the method comprises:
(i) preparing a first aqueous solution of poly(I:C) or a salt or solvate thereof, and a second aqueous solution of linear polyethyleneimine or a salt or solvate thereof;
(ii) independently filtering each respective first and second aqueous solution through a filter having a pore diameter of less than or equal to 500 nm thereby forming a corresponding first and second sterilized solution; and
(iii) mixing each resulting first and second sterilized solution in a mixing chamber thereby forming the aqueous composition.

2. The method according to claim 1, wherein each particle has a median diameter (D50%) of 85+/−20 nm.

3. The method according to claim 1, wherein the polydispersity index of each particle diameter is between 0.2 and 0.3.

4. The method according to claim 1, wherein each particle further comprises at least one pharmaceutically acceptable carrier, organic solvent, excipient and/or adjuvant.

5. The method according to claim 1, wherein each particle further comprises glucose or mannitol at a concentration of between 1 and 10% (weight/volume).

6. The method according to claim 1, wherein the aqueous composition has a pH of between 3.0+/−0.2 and an osmolality of between 300 and 310 mOsm/kg.

7. The method according to claim 1, wherein one of the respective first and second sterilized solutions is introduced into the other respective sterilized solution in the mixing chamber at a rate of greater than or equal to 1 mU/min.

8. The method according to claim 1, wherein each respective first and second sterilized solutions is introduced into the mixing chamber simultaneously at a rate of greater than or equal to 1 ml/min.

9. The method according to claim 1, wherein each respective first and second sterilized solution is introduced individually into the mixing chamber by injection.

10. The method according to claim 1, wherein the respective first and second sterilized solutions are simultaneously introduced in the mixing chamber by injection.

11. The method according to claim 1, wherein each respective first and second sterilized solution is introduced into the mixing chamber at a rate of between 20 ml/min and 100 ml/min.

12. The method according to claim 1, wherein either or both of the respective first and second sterilized solutions further comprise a pharmaceutically acceptable carrier, organic solvent, excipient and/or adjuvant.

13. The method according to claim 1, wherein the mixing chamber has a volume of between 0.2 ml and 10 ml.

14. The method according to claim 1,
wherein an adjuvant or therapeutic compound is added during or after step (i) to the first aqueous solution or the second aqueous solution, or
wherein an adjuvant or therapeutic compound is added during or after step (ii) to the first sterilized solution or the sterilized solution, or
wherein an adjuvant or therapeutic compound is added to the mixing chamber during or after step (iii).

15. The method according to claim 14, wherein the therapeutic compound is CD40L, IL-12, one or more viral or tumor antigens, miRNA, mRNA, or a nucleic acid-based drug.

16. The method according to claim 1, wherein the therapeutic compound is an anti-cancer drug.

17. The method according to claim 1, wherein the aqueous composition formed in step (iii) is filtered through a filter having a pore diameter of less than or equal to 600 nm to thereby form a filtrate.

18. The method according to claim 17, wherein the aqueous composition formed in step (iii) is lyophilised.

19. The method according to claim 1, wherein the aqueous composition formed in step (iii) is prepared in aliquots in a single-use vial, a syringe, or a storage container.

* * * * *